(12) United States Patent
Miller et al.

(10) Patent No.: US 11,439,673 B2
(45) Date of Patent: Sep. 13, 2022

(54) BACTERIA ENGINEERED TO TREAT LIVER DISEASE

(71) Applicant: Synlogic Operating Company, Inc., Cambridge, MA (US)

(72) Inventors: Paul F. Miller, Salem, CT (US); Vincent M. Isabella, Medford, MA (US); Dean Falb, Sherborn, MA (US); Jonathan W. Kotula, Berkeley, CA (US); Yossi Dagon, Ashland, MA (US)

(73) Assignee: Synlogic Operating Company, Inc., Cambridge, MA (US)

( * ) Notice: Subject to any disclaimer, the term of this patent is extended or adjusted under 35 U.S.C. 154(b) by 0 days.

(21) Appl. No.: 17/058,172

(22) PCT Filed: May 31, 2019

(86) PCT No.: PCT/US2019/034969
§ 371 (c)(1),
(2) Date: Nov. 24, 2020

(87) PCT Pub. No.: WO2019/232415
PCT Pub. Date: Dec. 5, 2019

(65) Prior Publication Data
US 2021/0154243 A1    May 27, 2021

Related U.S. Application Data

(60) Provisional application No. 62/679,772, filed on Jun. 2, 2018.

(51) Int. Cl.
| | | |
|---|---|---|
| *A61K 35/742* | (2015.01) | |
| *A61P 1/16* | (2006.01) | |
| *A61K 35/745* | (2015.01) | |

(52) U.S. Cl.
CPC .......... *A61K 35/742* (2013.01); *A61K 35/745* (2013.01); *A61P 1/16* (2018.01)

(58) Field of Classification Search
None
See application file for complete search history.

(56) References Cited

U.S. PATENT DOCUMENTS

| 5,807,708 A | 9/1998 | Falb et al. |
|---|---|---|
| 2006/0115493 A1 | 6/2006 | Hone et al. |
| 2013/0158097 A1 | 6/2013 | Hinkle et al. |
| 2016/0333326 A1* | 11/2016 | Falb ................. A61K 35/74 |
| 2019/0017050 A1 | 1/2019 | Thanos et al. |

FOREIGN PATENT DOCUMENTS

| EP | 3227440 A1 | 10/2017 |
|---|---|---|
| WO | 2016/090343 A1 | 6/2016 |
| WO | 2017/123418 A1 | 7/2017 |
| WO | 2017/123675 A1 | 7/2017 |

OTHER PUBLICATIONS

International Search Report and Written Opinion for Application No. PCT/US2019/034969, dated Sep. 26, 2019, 10 pages.
International Preliminary Report on Patentability for Application No. PCT/US2019/034969, dated Dec. 17, 2020, 7 pages.
Riordan et al., Treatment of hepatic encephalopathy. N Engl J Med. Aug. 14, 1997;337(7):473-9.

* cited by examiner

*Primary Examiner* — Brian Gangle
(74) *Attorney, Agent, or Firm* — McCarter & English, LLP; Marcie B. Clarke

(57) ABSTRACT

The disclosure provides genetically engineered bacteria that are capable of reducing excess ammonia and converting ammonia and/or nitrogen into alternate byproducts. The invention also provides pharmaceutical compositions comprising the genetically engineered bacteria, and methods of modulating and treating disorders associated with excess ammonia and inflammation in the gut and the liver, including, for example, hepatic encephalopathy, NASH/NAFLD, HCV, and Huntington's disease, in a subject, comprising administering the engineered bacterium to the subject.

22 Claims, 7 Drawing Sheets

Specification includes a Sequence Listing.

*P<0.05*

SEQUENCE LISTING

<160> NUMBER OF SEQ ID NOS: 3

<210> SEQ ID NO 1
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
atggtaaagg aacgtaaaac cgagttggtc gagggattcc gccattcggt tccctgtatc      60
aatacccacc ggggaaaaac gtttgtcatc atgctcggcg gtgaagccat tgagcatgag     120
aatttctcca gtatcgttaa tgatatcggg ttgttgcaca gcctcggcat ccgtctggtg     180
gtggtctatg gcgcacgtcc gcagatcgac gcaaatctgg ctgcgcatca ccacgaaccg     240
ctgtatcaca agaatatacg tgtgaccgac gccaaaacac tggaactggt gaagcaggct     300
gcgggaacat tgcaactgga tattactgct cgcctgtcga tgagtctcaa taacacgccg     360
ctgcagggcg cgcatatcaa cgtcgtcagt ggcaatttta ttattgccca gccgctgggc     420
gtcgatgacg gcgtggatta ctgccatagc gggcgtatcc ggcggattga tgaagacgcg     480
atccatcgtc aactggacag cggtgcaata gtgctaatgg ggccggtcgc tgtttcagtc     540
```

```
actggcgaga gctttaacct gacctcggaa gagattgcca ctcaactggc catcaaactg    600
aaagctgaaa agatgattgg ttttgctct tcccagggcg tcactaatga cgacggtgat    660
attgtctccg aacttttccc taacgaagcg caagcgcggg tagaagccca ggaagagaaa    720
ggcgattaca actccggtac ggtgcgcttt ttgcgtggcg cagtgaaagc ctgccgcagc    780
ggcgtgcgtc gctgtcattt aatcagttat caggaagatg gcgcgctgtt gcaagagttg    840
ttctcacgcg acggtatcgg tacgcagatt gtgatgaaa gcgccgagca gattcgtcgc    900
gcaacaatca acgatattgg cggtattctg gagttgattc gcccactgga gcagcaaggt    960
attctggtac gccgttctcg cgagcagctg gagatgaaa tcgacaaatt caccattatt   1020
cagcgcgata acacgactat tgcctgcgcc gcgctctatc cgttcccgga agagaagatt   1080
ggggaaatgg cctgtgtggc agttcacccg gattaccgca gttcatcaag gggtgaagtt   1140
ctgctggaac gcattgccgc tcaggctaag cagagcggct taagcaaatt gtttgtgctg   1200
accacgcgca gtattcactg gttccaggaa cgtggattta ccccagtgga tattgattta   1260
ctgcccgaga gcaaaaagca gttgtacaac taccagcgta aatccaaagt gttgatggcg   1320
gatttagggt aa                                                      1332

<210> SEQ ID NO 2
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Val Lys Glu Arg Lys Thr Glu Leu Val Glu Gly Phe Arg His Ser
1               5                   10                  15

Val Pro Cys Ile Asn Thr His Arg Gly Lys Thr Phe Val Ile Met Leu
            20                  25                  30

Gly Gly Glu Ala Ile Glu His Glu Asn Phe Ser Ser Ile Val Asn Asp
        35                  40                  45

Ile Gly Leu Leu His Ser Leu Gly Ile Arg Leu Val Val Val Tyr Gly
    50                  55                  60

Ala Arg Pro Gln Ile Asp Ala Asn Leu Ala Ala His His Glu Pro
65                  70                  75                  80

Leu Tyr His Lys Asn Ile Arg Val Thr Asp Ala Lys Thr Leu Glu Leu
                85                  90                  95

Val Lys Gln Ala Ala Gly Thr Leu Gln Leu Asp Ile Thr Ala Arg Leu
            100                 105                 110

Ser Met Ser Leu Asn Asn Thr Pro Leu Gln Gly Ala His Ile Asn Val
        115                 120                 125

Val Ser Gly Asn Phe Ile Ile Ala Gln Pro Leu Gly Val Asp Asp Gly
    130                 135                 140

Val Asp Tyr Cys His Ser Gly Arg Ile Arg Arg Ile Asp Glu Asp Ala
145                 150                 155                 160

Ile His Arg Gln Leu Asp Ser Gly Ala Ile Val Leu Met Gly Pro Val
                165                 170                 175

Ala Val Ser Val Thr Gly Glu Ser Phe Asn Leu Thr Ser Glu Glu Ile
            180                 185                 190

Ala Thr Gln Leu Ala Ile Lys Leu Lys Ala Glu Lys Met Ile Gly Phe
        195                 200                 205
```

```
Cys Ser Ser Gln Gly Val Thr Asn Asp Asp Gly Asp Ile Val Ser Glu
    210             215                 220

Leu Phe Pro Asn Glu Ala Gln Ala Arg Val Glu Ala Gln Glu Glu Lys
225             230                 235                 240

Gly Asp Tyr Asn Ser Gly Thr Val Arg Phe Leu Arg Gly Ala Val Lys
                245                 250                 255

Ala Cys Arg Ser Gly Val Arg Arg Cys His Leu Ile Ser Tyr Gln Glu
                260                 265             270

Asp Gly Ala Leu Leu Gln Glu Leu Phe Ser Arg Asp Gly Ile Gly Thr
            275                 280                 285

Gln Ile Val Met Glu Ser Ala Glu Gln Ile Arg Arg Ala Thr Ile Asn
290                 295                 300

Asp Ile Gly Gly Ile Leu Glu Leu Ile Arg Pro Leu Glu Gln Gln Gly
305             310                 315                 320

Ile Leu Val Arg Arg Ser Arg Glu Gln Leu Glu Met Glu Ile Asp Lys
                325                 330                 335

Phe Thr Ile Ile Gln Arg Asp Asn Thr Thr Ile Ala Cys Ala Ala Leu
                340                 345                 350

Tyr Pro Phe Pro Glu Glu Lys Ile Gly Glu Met Ala Cys Val Ala Val
                355                 360                 365

His Pro Asp Tyr Arg Ser Ser Arg Gly Glu Val Leu Leu Glu Arg
                370                 375             380

Ile Ala Ala Gln Ala Lys Gln Ser Gly Leu Ser Lys Leu Phe Val Leu
385                 390                 395                 400

Thr Thr Arg Ser Ile His Trp Phe Gln Glu Arg Gly Phe Thr Pro Val
                405                 410                 415

Asp Ile Asp Leu Leu Pro Glu Ser Lys Lys Gln Leu Tyr Asn Tyr Gln
                420                 425                 430

Arg Lys Ser Lys Val Leu Met Ala Asp Leu Gly
                435                 440

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 3
wntgaatwww wattcanw                                              18
```

BACTERIA ENGINEERED TO TREAT LIVER DISEASE

RELATED APPLICATIONS

The instant application is a 35 U.S.C. § 371 national stage filing of International Application No. PCT/US2019/034969, filed on May 31, 2019, which claims priority to U.S. Provisional Application No. 62/679,772, filed on Jun. 2, 2018. The entire contents of each of the aforementioned applications are expressly incorporated herein by reference.

SEQUENCE LISTING

The instant application contains a Sequence Listing which has been submitted electronically in ASCII format and is hereby incorporated by reference in its entirety. Said ASCII copy, created on Jul. 12, 2019, is named 126046-03920 SL.txt and is 6,567 bytes in size.

BACKGROUND

The liver plays a central role in amino acid metabolism and protein synthesis and breakdown, as well as in several detoxification processes, notably those of end-products of intestinal metabolism, like ammonia. Liver dysfunction, resulting in inflammation, hyperammonemia, and liver damage and fibrosis may cause hepatic encephalopathy (HE), which disorder encompasses a spectrum of potentially reversible neuropsychiatric abnormalities observed in patients with liver dysfunction (after exclusion of unrelated neurologic and/or metabolic abnormalities). In HE, severe liver failure (e.g., cirrhosis) and/or portosystemic shunting of blood around the liver permit elevated arterial levels of ammonia to permeate the blood-brain barrier (Williams, 2006), resulting in altered brain function.

Ammonia dysmetabolism cannot solely explain all the neurological changes that are seen in patients with HE. Sepsis is a well-known precipitating factor for HE. The systemic inflammatory response syndrome (SIRS) results from the release and circulation of proinflammatory cytokines and mediators. In patients with cirrhosis, SIRS may exacerbate the symptoms of HE, both in patients with minimal and overt HE in a process likely mediated by tumor necrosis factor (TNF) and interleukin-6 (IL6). Notably, enhanced production of reactive nitrogen species (RNS) and reactive oxygen species (ROS) occurs in cultured astrocytes that are exposed to ammonia, inflammatory cytokines, hyponatremia or benzodiazepines.

Non-alcoholic fatty liver disease (NAFLD) describes a range of conditions caused by a build-up of fat within liver cells. The first stage of NAFLD is simple fatty liver—also called hepatic steatosis, which often does not cause severe symptoms in the liver; however hepatic steatosis in some patients can progress to more severe forms of NAFLD.

Non-alcoholic steatohepatitis (NASH) is a severe form of NAFLD, where excess fat accumulation in the liver results in chronic inflammation and damage. NASH affects approximately 3-5% of the population in America, especially in those identified as obese. NASH is characterized by such abnormalities as advanced lipotoxic metabolites, proinflammatory substrate, fibrosis, and increased hepatic lipid deposition. If left untreated, NASH can lead to cirrhosis, liver failure, and hepatocellular carcinoma (HCC). Although patients diagnosed with alcoholic steatohepatitis demonstrate similar symptoms and liver damage, NASH develops in individuals who do not consume alcohol, and the underlying causes of NASH are unknown. Possible factors include insulin resistance, cytokine imbalance (specifically, an increase in the tumor necrosis factor-alpha (TNF-α)/adiponectin ratio), and oxidative stress resulting from mitochondrial abnormalities.

Intestinal microbiota plays an important role in health and disease, including liver disease. The liver's function to remove toxins, such as ammonia, is connected to the gut through the portal vein. Under pathological condition, such as disrupted gut barrier and inflammation, bacterial components are released into so-called the liver-gut axis, which results in inflammatory responses in the liver; these responses can initiate direct damage to liver cells. Probiotics have been shown to have beneficial effects in the treatment of several liver diseases by counteracting the production of bacterial toxins and by improving gut barrier function, reducing intestinal permeability, and dampening the inflammatory response (Chavez-Tapia, et al., Current evidence on the use of probiotics in liver diseases; Journal of Functional Foods; Volume 17, August 2015, Pages 137-151).

Current therapies for hepatic encephalopathy, NASH/NAFLD and other liver diseases associated with elevated liver inflammation and hyperammonemia are insufficient. Thus, there is significant unmet need for effective, reliable, and/or long-term treatment for hepatic encephalopathy and Huntington's disease.

SUMMARY

The disclosure provides genetically engineered bacteria that are capable of reducing excess ammonia and converting ammonia and/or nitrogen into alternate byproducts. The disclosure further provides genetically engineered bacteria that are capable of reducing inflammation in the subject. In certain embodiments, the genetically engineered bacteria reduce excess ammonia and convert ammonia and/or nitrogen into alternate byproducts, including but not limited to, arginine. In certain embodiments, the genetically engineered bacteria are non-pathogenic and may be introduced into the gut in order to reduce toxic ammonia and/or inflammation in the gut and the liver. The invention also provides pharmaceutical compositions comprising the genetically engineered bacteria, and methods of modulating and treating disorders associated with hyperammonemia, e.g., urea cycle disorders and hepatic encephalopathy and other liver disorders.

The invention also provides pharmaceutical compositions comprising the genetically engineered bacteria, and methods of modulating and treating disorders associated with excess ammonia and inflammation in the gut and the liver, including, for example, hepatic encephalopathy, NASH/NAFLD, HCV, and Huntington's disease. In some embodiments, methods of treating a subject with liver disease are provided, in which the engineered bacterium or a pharmaceutical composition comprising the engineered bacterium is administered to the subject, wherein the bacterium is capable of reducing inflammation, and thereby treating the subject. In some embodiments, the methods of administering the engineered bacterium are able to reduce inflammation in the colon observed prior to treatment with the bacterium. In some embodiments, the methods of administering the engineered bacterium are able to reduce inflammation in the liver observed prior to treatment with the bacterium. In some embodiments, the methods of administering the engineered bacterium are able to reduce liver damage or fibrosis in the liver observed prior to treatment with the bacterium. In some embodiments, the methods of administering the engineered bacterium are able to reduce hyperammonemia as measured by ammonia levels in the blood observed prior to treatment with the bacterium.

In some of the methods provided herein, the bacterium comprises one or more gene sequences encoding an ammonia consumption circuit. In some of the methods provided herein, the bacterium comprises one or more gene sequences encoding an arginine production circuit. In some of the methods provided herein, the genetically engineered bacteria comprise one or more gene(s) or gene cassette(s) or circuit(s), containing one or more native or non-native component(s), which mediate one or more mechanisms of action. Additionally, one or more endogenous genes or regulatory regions within the bacterial chromosome may be mutated or deleted. The genetically engineered bacteria harbor these genes or gene cassettes or circuits on a plasmid or, alternatively, the genes/gene cassettes have been inserted into the chromosome at certain regions, where they do not interfere with essential gene expression.

In some of the methods provided herein, the genetically engineered bacteria comprise one or more gene sequences encoding a feedback resistant N-acetylglutamate synthetase (ArgA), and further comprise a mutation or deletion in the endogenous feedback repressor of arginine synthesis ArgR. In some embodiments, the genetically engineered bacteria comprise a deletion or mutation in the ThyA gene. These gene(s)/gene cassette(s) may be under the control of constitutive or inducible promoters. Exemplary inducible promoters described herein include oxygen level-dependent promoters (e.g., FNR-inducible promoter), promoters induced by HE-specific molecules or metabolites indicative of liver damage (e.g., bilirubin), promoters induced by inflammation or an inflammatory response (RNS, ROS promoters), and promoters induced by a metabolite that may or may not be naturally present (e.g., can be exogenously added) in the gut, e.g., arabinose and tetracycline.

In addition, the engineered bacteria may further comprise one or more of more of the following: (1) one or more auxotrophies, such as any auxotrophies known in the art and provided herein, e.g., thyA auxotrophy, (2) one or more kill switch circuits, such as any of the kill-switches described herein or otherwise known in the art, (3) one or more antibiotic resistance circuits, (4) one or more transporters for importing biological molecules or substrates, such any of the transporters described herein or otherwise known in the art, (5) one or more secretion circuits, such as any of the secretion circuits described herein and otherwise known in the art, and (6) combinations of one or more of such additional circuits.

In one aspect, the disclosure provides a method for treating a subject having liver disease, the method comprising: administering an engineered bacterium, or a pharmaceutical composition comprising the engineered bacterium, to the subject, wherein the administering: reduces IL-6 gene expression in the liver by at least 10% as compared to IL-6 gene expression in the liver before the administering; reduces TNFα gene expression in the liver by at least 10% as compared to TNFα gene expression in the liver before the administering; reduces TGFβ gene expression in the liver by at least 10% as compared TGFβ gene expression in the liver before the administering; reduces αSMA gene expression in the liver by at least 10% as compared αSMA gene expression in the liver before the administering; reduces IL-6 gene expression in the colon by at least 10% as compared IL-6 gene expression in the colon before the administering; and/or wherein blood ammonia levels are decreased by at least 5% after administering as compared to blood ammonia levels before the administering.

In one embodiment, the administering reduces IL-6 gene expression in the liver by at least 15% as compared to IL-6 gene expression in the liver before the administering.

In one embodiment, the administering reduces IL-6 gene expression in the liver by at least 20% as compared to IL-6 gene expression in the liver before the administering.

In one embodiment, the administering reduces IL-6 gene expression in the liver by at least 25% as compared to IL-6 gene expression in the liver before the administering.

In one embodiment, the administering reduces IL-6 gene expression in the liver by at least 30% as compared to IL-6 gene expression in the liver before the administering.

In one embodiment, the administering reduces IL-6 gene expression in the liver by at least 35% as compared to IL-6 gene expression in the liver before the administering.

In one embodiment, the administering reduces IL-6 gene expression in the liver by at least 40% as compared to IL-6 gene expression in the liver before the administering.

In one embodiment, the administering reduces IL-6 gene expression in the liver by at least 45% as compared to IL-6 gene expression in the liver before the administering.

In one embodiment, the administering reduces IL-6 gene expression in the liver by at least 50% as compared to IL-6 gene expression in the liver before the administering.

In one embodiment, the administering reduces TGFβ gene expression in the liver by at least 15% as compared TGFβ gene expression in the liver before the administering.

In one embodiment, the administering reduces TGFβ gene expression in the liver by at least 20% as compared TGFβ gene expression in the liver before the administering.

In one embodiment, the administering reduces αSMA gene expression in the liver by at least 15% as compared αSMA gene expression in the liver before the administering.

In one embodiment, the administering reduces αSMA gene expression in the liver by at least 20% as compared αSMA gene expression in the liver before the administering.

In one embodiment, the administering reduces αSMA gene expression in the liver by at least 25% as compared αSMA gene expression in the liver before the administering.

In one embodiment, the administering reduces αSMA gene expression in the liver by at least 30% as compared αSMA gene expression in the liver before the administering.

In one embodiment, the administering reduces αSMA gene expression in the liver by at least 35% as compared αSMA gene expression in the liver before the administering.

In one embodiment, the administering reduces αSMA gene expression in the liver by at least 40% as compared αSMA gene expression in the liver before the administering.

In one embodiment, the administering reduces αSMA gene expression in the liver by at least 45% as compared αSMA gene expression in the liver before the administering.

In one embodiment, the administering reduces αSMA gene expression in the liver by at least 50% as compared αSMA gene expression in the liver before the administering.

In one embodiment, the administering reduces IL-6 gene expression in the colon by at least 15% as compared IL-6 gene expression in the colon before the administering.

In one embodiment, the administering reduces IL-6 gene expression in the colon by at least 20% as compared IL-6 gene expression in the colon before the administering.

In one embodiment, blood ammonia levels are decreased by at least 10% as compared to blood ammonia levels before the administering.

In one embodiment, blood ammonia levels are decreased by at least 15% as compared to blood ammonia levels before the administering.

In one embodiment, blood ammonia levels are decreased by at least 20% as compared to blood ammonia levels before the administering.

In one embodiment, blood ammonia levels are decreased by at least 25% as compared to blood ammonia levels before the administering.

In one embodiment, blood ammonia levels are decreased by at least 30% as compared to blood ammonia levels before the administering.

In one embodiment, blood ammonia levels are decreased by at least 35% as compared to blood ammonia levels before the administering.

In one embodiment, blood ammonia levels are decreased by at least 40% as compared to blood ammonia levels before the administering.

In one embodiment, blood ammonia levels are decreased by at least 45% as compared to blood ammonia levels before the administering.

In one embodiment, blood ammonia levels are decreased by at least 50% as compared to blood ammonia levels before the administering.

In one embodiment, the method further comprises measuring blood ammonia levels before the administering and/or further comprising measuring blood ammonia levels after the administering.

In one embodiment, the method further comprises measuring gene expression in the colon before the administering and/or further comprising measuring gene expression in the colon after administering.

In one embodiment, the method further comprises measuring gene expression in the liver before the administering and/or further comprising measuring gene expression in the liver after administering.

In one embodiment, the engineered bacterium reduces inflammation in the colon of the subject.

In one embodiment, the engineered bacterium reduces inflammation in the liver of the subject.

In one embodiment, the bacterium comprises one or more gene sequences encoding an ammonia consumption circuit.

In one embodiment, the bacterium comprises one or more gene sequences encoding an arginine production circuit.

In one embodiment, the bacterium comprises a gene encoding an arginine feedback resistant N-acetylglutamate synthetase (ArgAfbr), wherein the ArgAfbr has reduced arginine feedback inhibition as compared to a wild-type N-acetylglutamate synthetase from the same bacterial subtype under the same conditions and wherein expression of the gene encoding ArgAfbr is controlled by a promoter that is induced by low-oxygen or anaerobic conditions; and wherein the bacterium has been genetically engineered to lack a functional ArgR.

In one embodiment, each copy of a functional argR gene normally present in a corresponding wild-type bacterium has been deleted.

In one embodiment, under low-oxygen or anaerobic conditions, the transcription of each gene in the engineered bacterium that is present in an operon comprising a functional ARG box and which encodes an arginine biosynthesis enzyme is increased as compared to a corresponding gene in a wild-type bacterium under the same conditions.

In one embodiment, the bacterium comprises a gene sequence encoding a biosynthetic pathway for producing butyrate.

In one embodiment, the promoter that is induced under low-oxygen or anaerobic conditions is an FNR promoter.

In one embodiment, the bacterium is a non-pathogenic bacterium.

In one embodiment, the bacterium is a probiotic bacterium.

In one embodiment, the bacterium is selected from the group consisting of *Bacteroides*, *Bifidobacterium*, *Clostridium*, *Escherichia*, *Lactobacillus*, and *Lactococcus*.

In one embodiment, the bacterium is *Escherichia coli* strain Nissle.

In one embodiment, the bacterium is an auxotroph in a gene that is complemented when the bacterium is present in a mammalian gut.

In one embodiment, the bacterium is a thyA or dapB auxotroph.

In one embodiment, the liver disease is selected from NASH, NAFLD, and hepatic encephalopathy.

In another embodiment, the liver disease is hepatic encephalopathy.

DESCRIPTION OF EMBODIMENTS

Figure 1A:
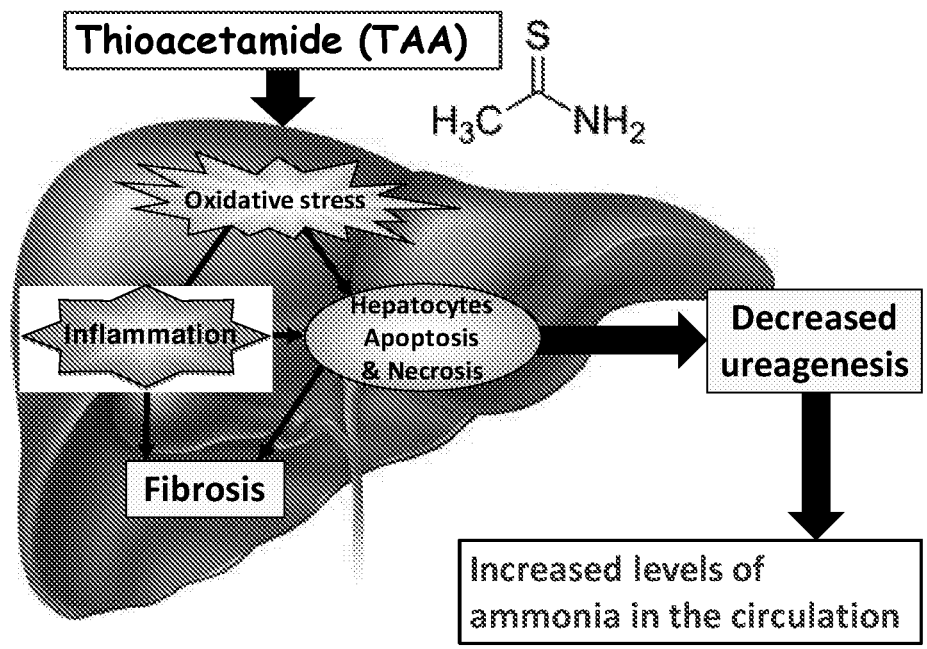
FIG. 1A depicts a schematic representation of thioacetamide-induced hepatic encephalopathy model in BALB/c mice.
Figure 1B:
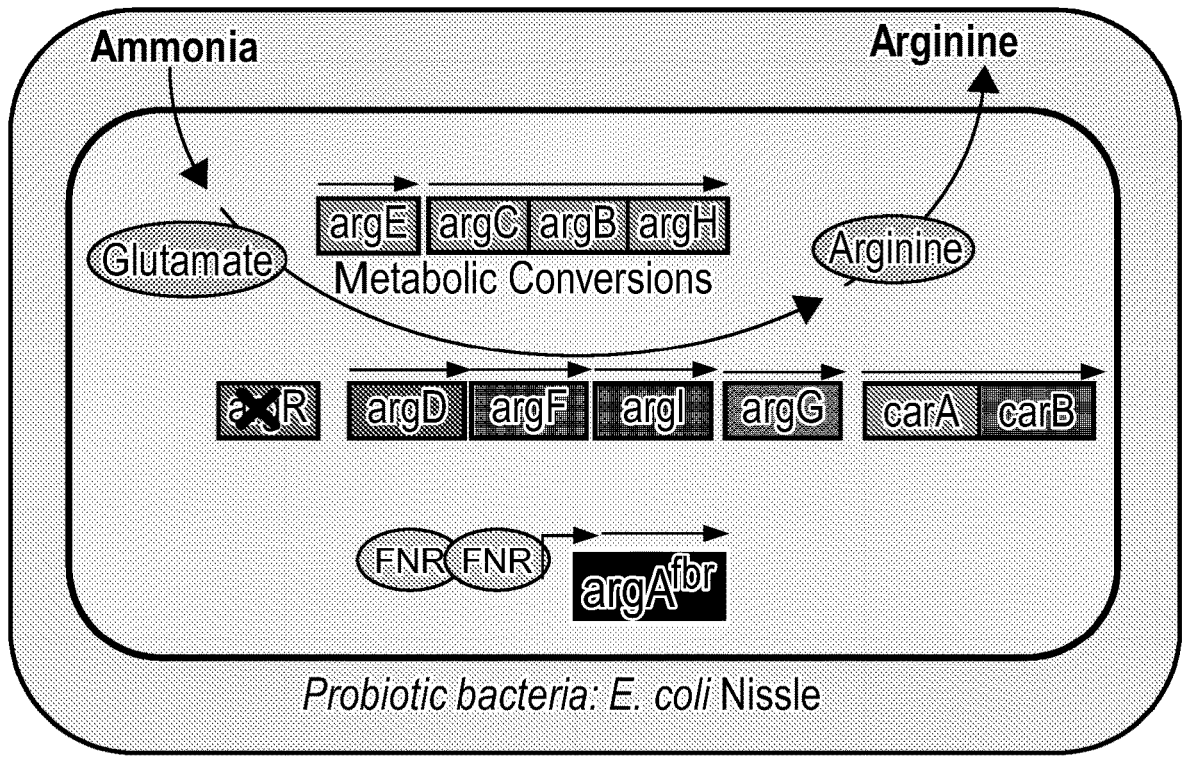
FIG. 1B depicts a schematic of a genetically engineered *E. coli* Nissle SYN-UCD305 which converts Ammonia into Arginine.
Figure 1C:
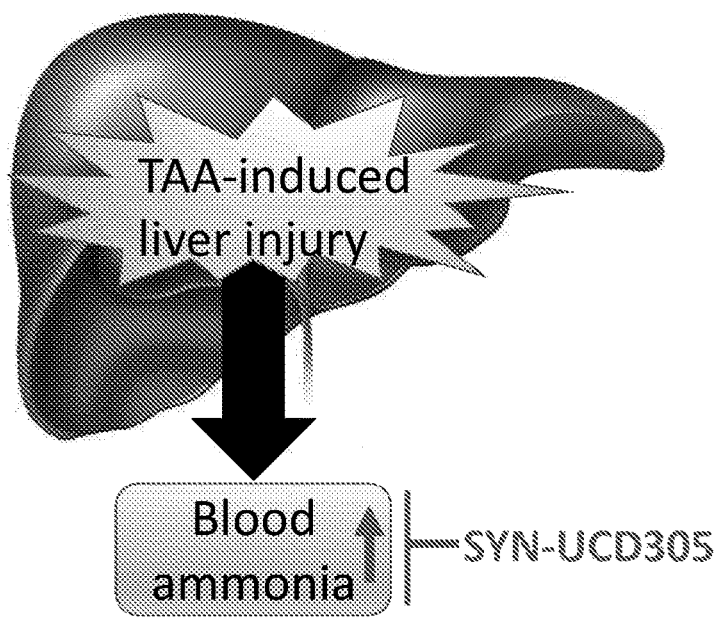
FIG. 1C depicts a schematic illustrating that SYN-UCD305 prevents the elevation of blood ammonia caused by hepatic injury in the TAA model.
Figure 2A:
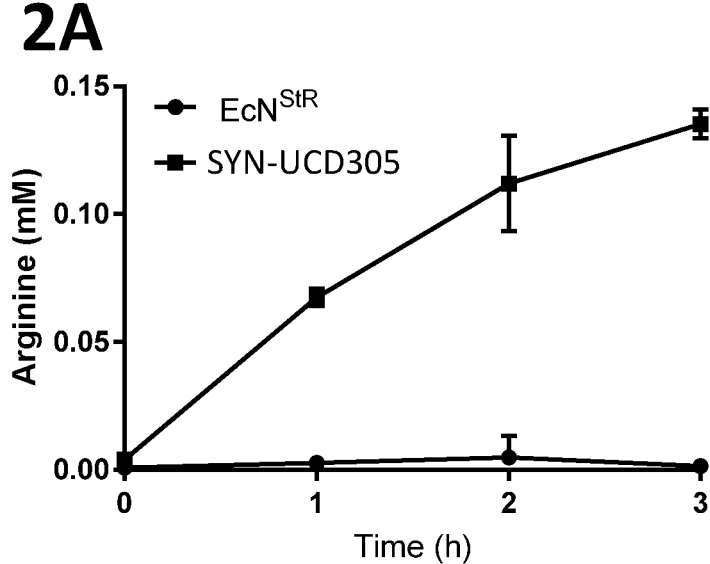
FIG. 2A depicts a graph showing in vitro arginine Production by SYN-UCD305.
Figure 2B:
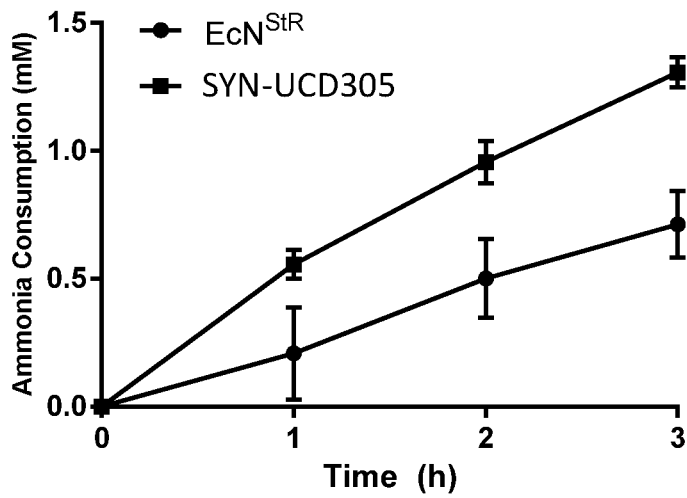
FIG. 2B depicts a graph showing in vitro ammonia consumption by SYN-UCD305. Mean Arg production rate=650 nmoles/$10^9$ cells/hr. Methods for these measurements are known in t the art, e.g., see U.S. Pat. No. 9,688,967, the contents of which is herein incorporated by reference in its entirety.
Figure 3:
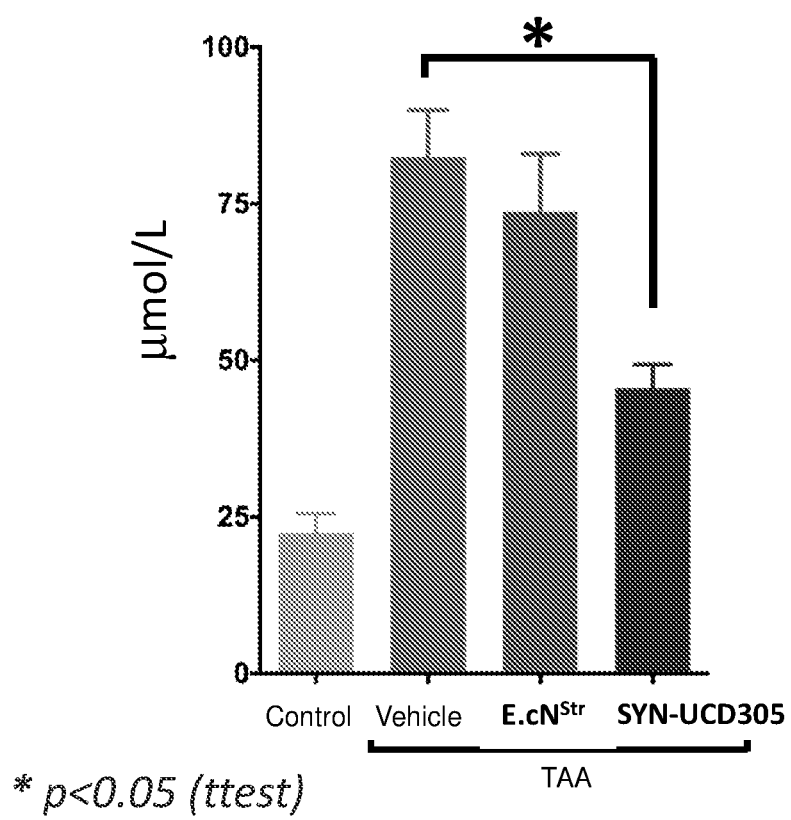
FIG. 3 depicts a graph showing the reduction of blood ammonia observed in a liver fibrosis study in which the mice were treated with TAA three times weekly for three weeks prior to the study and throughout the 21-day study. During the study, mice (n=10) were either gavaged with vehicle control, streptomycin resistant *E. coli* Nissle (1e10 CFU) or SYN-UCD305 (1e10 CFU) twice daily (BID) for 21 days.
Figure 4A:
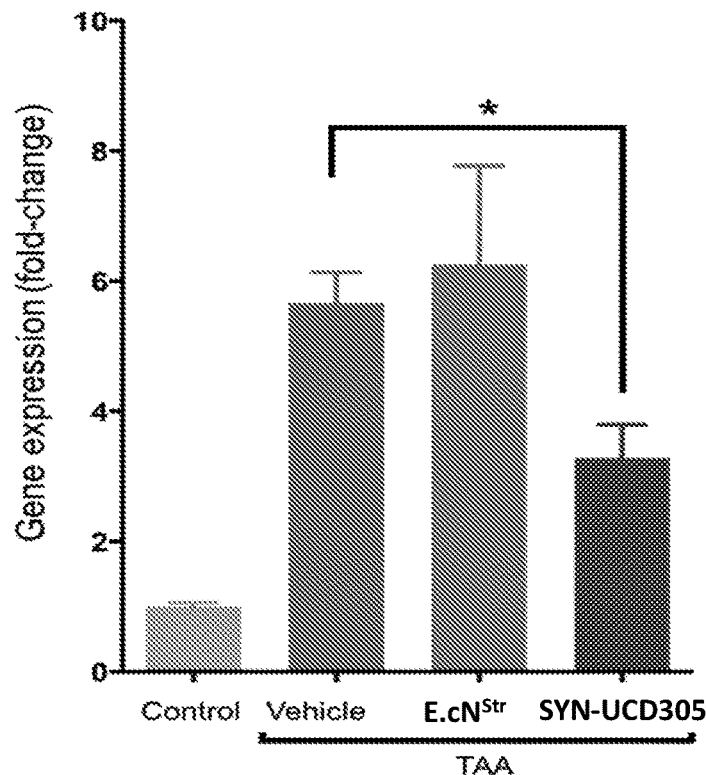
FIGS. 4A, 4B, 4C, and 4D depict graphs showing liver IL-6 (FIG. 4A), TNF-alpha (FIG. 4B), TGF-beta (FIG. 4C), and αSMA (smooth muscle specific actin) (FIG. 4D) mRNA levels observed upon oral gavage with vehicle control, streptomycin resistant *E. coli* Nissle or SYN-UCD305 in the liver fibrosis study described in FIG. 3.
Figure 4B:
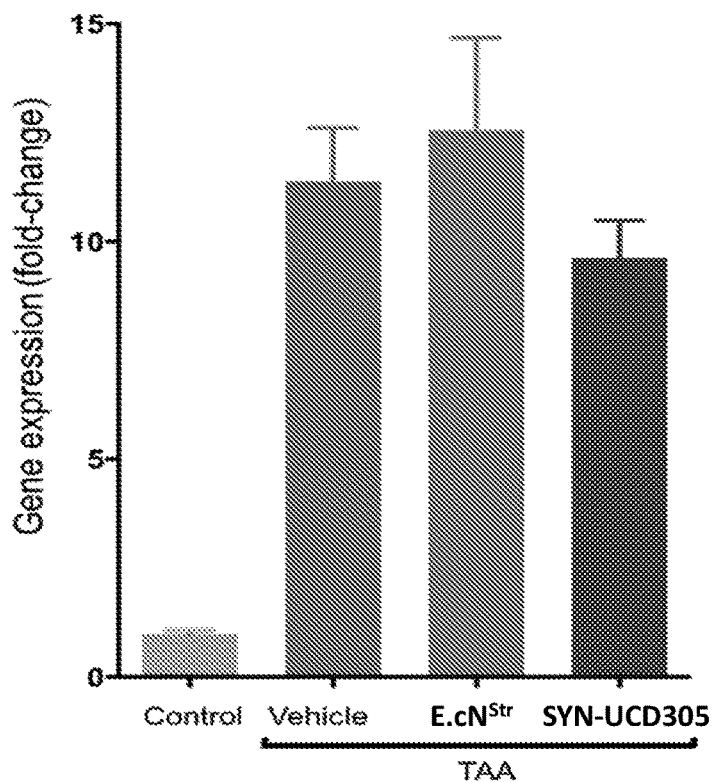
Figure 4C:
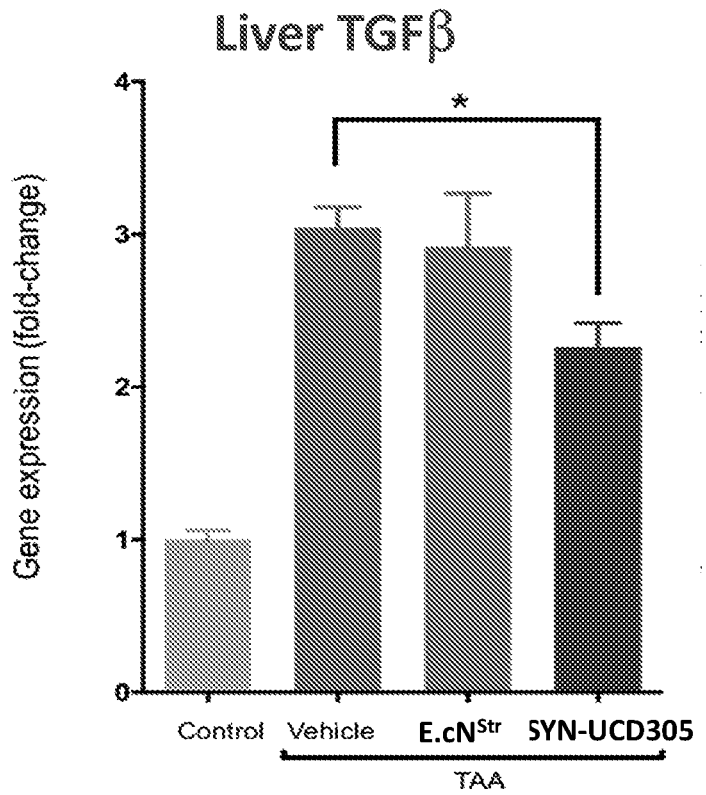
Figure 4D:
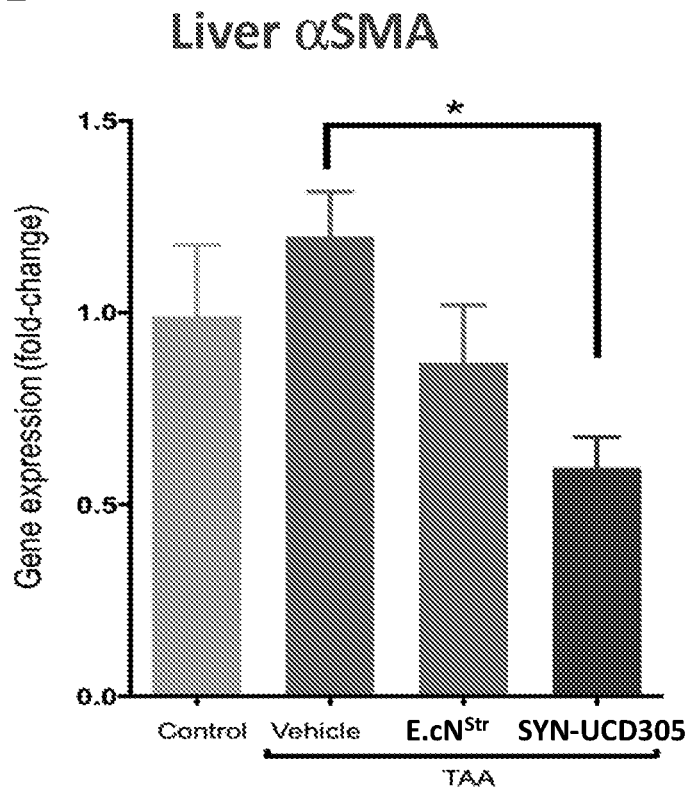

The invention includes genetically engineered bacteria, pharmaceutical compositions thereof, and methods of modulating or treating disorders of the liver e.g., hepatic encephalopathy and other liver disorders which are associated with liver and gut inflammation and in certain instances, excess ammonia or elevated ammonia levels. Methods of treating a subject with liver disease, including but not limited to, hepatic encephalitis and NAFDL and NASH, and HCV, are provided, which comprise administering engineered bacteria described herein, or a pharmaceutical composition comprising the engineered bacteria. In some embodiments, the bacteria are capable of reducing inflammation in the subject to be treated. In some embodiments, engineered bacterium reduces inflammation in the colon of the subject. In some embodiments, engineered bacterium reduces inflammation in the liver of the subject. In some embodiments, engineered bacterium reduces inflammation in the colon and the liver of the subject. In some embodiments, the reduction of inflammation in the colon can be measured using pro- or anti-inflammatory markers known in the art. In some embodiments, the reduction of inflammation in the colon can be measured using markers of gut barrier known in the art. In some embodiments, pro-inflammatory markers are reduced in the colon upon administration of the genetically engineered bacteria of the disclosure. Non-limiting examples of such inflammatory markers include IL-6 and TNF-alpha. In some embodiments, the reduction of inflammation in the liver can be measured using pro- or anti-inflammatory markers known in the art. In some embodiments, pro-inflammatory markers are reduced in the liver upon administration of the genetically engineered bacteria of the disclosure. Non-limiting examples of such inflammatory markers include IL-6, TNF-alpha, TGF-beta and others. In some embodiments, markers linked to human fibrosis in chronic liver disease can be measured and are reduced upon administration of the genetically engineered bacteria of the disclosure. A non-limiting example of such a fibrosis marker is the alpha isotype of actin (alpha-SMA). In some embodiments, engineered bacterium reduces hyperammonemia as measured in the blood of the subject. In some embodiments, the methods provided for treating a subject with liver disease include the administration of a genetically engineered bacterium which comprises one or more gene sequences encoding an ammonia consumption circuit. In some embodiments, the methods provided for treating a subject with liver disease include the administration of a genetically engineered bacterium which comprises one or more gene sequences encoding arginine production circuit. In some embodiments, the genetically engineered bacterium comprises a gene encoding an arginine feedback resistant N-acetylglutamate synthetase (ArgAfbr), wherein the ArgAfbr has reduced arginine feedback inhibition as compared to a wild-type N-acetylglutamate synthetase from the same bacterial subtype under the same conditions. In some embodiments, expression of the gene encoding ArgAfbr is controlled by a promoter that is induced by low-oxygen or anaerobic conditions. A non-limiting example of such a promoter is the FNR promoter. In some embodiments, the bacterium has been genetically engineered to lack a functional ArgR. In some embodiments, each copy of a functional argR gene normally present in a corresponding wild-type bacterium has been deleted. In some embodiments, under low-oxygen or anaerobic conditions, the transcription of each gene in the engineered bacterium that is present in an operon comprising a functional ARG box and which encodes an arginine biosynthesis enzyme is increased as compared to a corresponding gene in a wild-type bacterium under the same conditions. In some embodiments, the bacterium further comprises a gene sequence encoding a biosynthetic pathway for producing butyrate. In some embodiments, the bacterium is a non-pathogenic bacterium. In some embodiments, the bacterium is a probiotic bacterium, e.g., selected from *Bacteroides*, *Bifidobacterium*, *Clostridium*, *Escherichia*, *Lactobacillus*, and *Lactococcus*. In some embodiments, the bacterium is *Escherichia coli* strain Nissle. In some embodiments, the bacterium is an auxotroph in a gene that is complemented when the bacterium is present in a mammalian gut. In some embodiments, the bacterium is a thyA or dapB auxotroph.

"Hyperammonemia," "hyperammonemic," or "excess ammonia" is used to refer to increased concentrations of ammonia in the body. Hyperammonemia is caused by decreased detoxification and/or increased production of ammonia. Decreased detoxification may result from urea cycle disorders (UCDs), such as argininosuccinic aciduria, arginase deficiency, carbamoylphosphate synthetase deficiency, citrullinemia, N-acetylglutamate synthetase deficiency, and ornithine transcarbamylase deficiency; or from bypass of the liver, e.g., open *ductus hepaticus*; and/or deficiencies in glutamine synthetase (Hoffman et al., 2013; Haberle et al., 2013). Decreased detoxification may also result from liver disorders such as hepatic encephalopathy, acute liver failure, or chronic liver failure; and neurodegenerative disorders such as Huntington's disease (Chen et al., 2015; Chiang et al., 2007). Increased production of ammonia may result from infections, drugs, neurogenic bladder, and intestinal bacterial overgrowth (Haberle et al., 2013). Other disorders and conditions associated with hyperammonemia include, but are not limited to, liver disorders such as hepatic encephalopathy, acute liver failure, or chronic liver failure; organic acid disorders; isovaleric aciduria; 3-methylcrotonylglycinuria; methylmalonic acidemia; propionic aciduria; fatty acid oxidation defects; carnitine cycle defects; carnitine deficiency; β-oxidation deficiency; lysinuric protein intolerance; pyrroline-5-carboxylate synthetase deficiency; pyruvate carboxylase deficiency; ornithine aminotransferase deficiency; carbonic anhydrase deficiency; hyperinsulinism-hyperammonemia syndrome; mitochondrial disorders; valproate therapy; asparaginase therapy; total parenteral nutrition; cystoscopy with glycine-containing solutions; post-lung/bone marrow transplantation; portosystemic shunting; urinary tract infections; ureter dilation; multiple myeloma; and chemotherapy (Hoffman et al., 2013; Haberle et al., 2013; Pham et al., 2013; Lazier et al., 2014). In healthy subjects, plasma ammonia concentrations are typically less than about 50 µmol/L (Leonard, 2006). In some embodiments, a diagnostic signal of hyperammonemia is a plasma ammonia concentration of at least about 50 µmon, at least about 80 µmol/L, at least about 150 µmol/L, at least about 180 µmol/L, or at least about 200 µmol/L (Leonard, 2006; Hoffman et al., 2013; Haberle et al., 2013).

"Gut-liver axis" refers to the interconnectivity between the liver and the gut. The gut liver axis plays a critical role in liver disease, including HE, NAFLD and NASH. The microbiome, providing large amounts of diverse bacterial metabolites, is at the center of the gut-liver-axis. In conditions of increased intestinal permeability, potentially harmful bacterial products can cross the epithelial barrier to a greater extent than in intact epithelium, causing the release pro-inflammatory cytokines (TNF, IL1, IL6 etc.) from lymphocytes. This leads to portal-venous pathogen/microbe-associated molecular patterns (P/MAMPs)- and immune system activation. Moreover, harmful bacterial metabolites increasingly are able to penetrate the epithelial barrier and then can—upon passing the gut vascular barrier—reach the portal-venous circulation. In the liver, the portal-venous inflow of stimulants, and hepatic stellate cells, promotes inflammation, liver injury and fibrosis (reviewed in Wiest et al., Targeting the gut-liver axis in liver disease; Journal of Hepatology; Volume 67, Issue 5, November 2017, Pages 1084-1103). As such, strategy in the treatment, prevention, and/or management of liver disease may include approaches to help maintain and/or reestablish gut barrier function, e.g. through the prevention, treatment and/or management of inflammatory events at the root of increased permeability, e.g. through the administration of anti-inflammatory effectors and/or gut barrier effectors.

In some embodiments, the genetically engineered bacteria described herein are useful in the treatment, prevention and/or management of HE. Hepatic encephalopathy (HE) is a syndrome observed in patients with cirrhosis. Hepatic encephalopathy is defined as a spectrum of neuropsychiatric abnormalities in patients with liver dysfunction. Hepatic encephalopathy is characterized by personality changes, intellectual impairment, and a depressed level of consciousness. The pathogenesis of HE is thought to be related to high ammonia levels as a result of liver failure and/or due to the presence of porto-systemic shunts in patients with cirrhosis. The liver, which receives 70% of its blood supply from the gut through the portal venous system, is significantly affected by the gut and its contents. Intestinal barrier dysfunction and systemic inflammation, altered gut flora and their by-products play an important role in the pathogenesis of HE. Impaired intestinal barrier integrity, results in increased bacterial translocation and release of endotoxins (lipopolysaccharides, flagellin, peptidoglycan, and microbial nucleic acids) in circulation, and systemic inflammation. In cirrhosis, changes in intestinal tight junctional proteins have been described; though the pathophysiology is not clear, alcohol metabolites and proinflammatory cytokines have been postulated to result in leaky intestine (Quigley E. M., Stanton C., Murphy E. F. The gut microbiota and the liver. Pathophysiological and clinical implications. J Hepatol. 2013; 58:1020-1027). In some embodiments, the genetically engineered bacteria described herein provide a method of treatment, prevention, and/or management of HE through reduction in inflammation in the gut.

Nonalcoholic fatty liver disease (NAFLD) is one of the most common liver diseases. Nonalcoholic fatty liver disease is a component of metabolic syndrome and a spectrum of liver disorders ranging from simple steatosis to nonalcoholic steatohepatitis (NASH). Simple liver steatosis is defined as a benign form of NAFLD with minimal risk of progression, in contrast to NASH, which tends to progress to cirrhosis in up to 20% of patients and can subsequently lead to liver failure or hepatocellular carcinoma. Hepatic steatosis occurs when the amount of imported and synthesized lipids exceeds the export or catabolism in hepatocytes. An excess intake of fat or carbohydrate is the main cause of hepatic steatosis. NAFLD patients exhibit signs of liver inflammation and increased hepatic lipid accumulation. In addition, the development of NAFLD in obese individuals is closely associated with insulin resistance and other metabolic disorders and thus might be of clinical relevance). Evidence is increasing that the gut and liver have multiple levels of associated interdependence, and disturbance of the gut-liver axis has been implicated in a number of conditions linked to obesity, including NAFLD and NASH. The liver has both an arterial and venous blood supply, with the majority of hepatic blood flow coming from the gut via the portal vein. In NASH the liver is exposed to potentially harmful substances derived from the gut (thought increased gut permeability and reduced intestinal integrity), including translocated bacteria, LPS and endotoxins, food antigens, as well as secreted cytokines. Tight junction proteins, such as zonula occludens, normally seal the junction between intestinal endothelial cells at their apical aspect and thus have a vital role in preventing translocation of harmful substances from the gut into the portal system. In NAFLD/NASH, these tight junctions are disrupted, increasing mucosal permeability and exposing both the gut mucosal cells and the liver to potentially pro-inflammatory bacterial products. Translocated microbial products might contribute to the pathogenesis of fatty liver disease by several mechanisms, including stimulating pro-inflammatory and profibrotic pathways via a range of cytokines. As such, one strategy in the treatment, prevention, and/or management of NASH may include approaches to help maintain and/or reestablish gut barrier function, e.g. through the prevention, treatment and/or management of inflammatory events at the root of increased permeability. In some embodiments, the genetically engineered bacteria described herein are useful in the treatment, prevention and/or management of NAFLD and/or NASH.

Worldwide, chronic viral hepatitis C (VHC) prevalence is around 3% of the population. The prognosis of hepatitis C virus (HCV) infected patients is correlated with liver fibrosis progression towards cirrhosis and the development of hepatocellular carcinoma (HCC). In early stage of HCV infection, the immune system generates antibodies to eradicate the virus and, once the infection becomes chronic, it inflicts hepatocyte damage through direct cellular toxicity and local stimulation of inflammatory cytokine expression, which triggers liver fibrosis by activating hepatic stellate cells (HSCs). In some embodiments, the genetically engineered bacteria described herein are useful in the treatment, prevention and/or management of VHC.

The effect of the genetically engineered bacteria on the inflammatory and fibrotic status can be measured by methods known in the art, e.g., plasma can be drawn before and after administration of the genetically engineered bacteria. The erythrocyte sedimentation rate (ESR), C-reactive protein (CRP) and plasma viscosity (PV) blood tests are commonly used to detect this increase in inflammation. In some embodiments the genetically engineered bacteria modulate, e.g. decrease or increase, levels of inflammatory markers, eg. C-reactive protein (CRP). Liver fibrosis can also be measured, in some cases by scoring non-invasive markers. Examples of non-invasive markers which may be modulated by the genetically engineered bacteria are for example described in Chin et al., Non-invasive Markers of Liver Fibrosis: Adjuncts or Alternatives to Liver Biopsy?; Front Pharmacol. 2016; 7: 159, incorporated herein by reference in its entirety).

Inflammatory markers in the gut which can be modulated by the engineered bacteria according to the methods described herein, are well-known in the art. Non-limiting examples are described in Derikx et al., Non-invasive markers of gut wall integrity in health and disease; World J Gastroenterol. 2010 Nov. 14; 16(42): 5272-5279, the contents of which is herein incorporated by reference in its entirety.

Inflammatory markers in the liver which can be modulated by the engineered bacteria according to the methods described herein, are well-known in the art and for example include NF-kappaB a, IL-6, IL-8, AST and ALT.

In some embodiments, the genetically engineered bacteria modulate, e.g. decrease, levels of inflammatory growth factors and cytokines, e.g., IL-1$\beta$, IL-6, and/or TNF-$\alpha$ and proinflammatory signaling, e.g. NF-kappaB signaling, e.g., in the gut or the liver. In some embodiments the genetically engineered bacteria modulate, e.g. increase, levels of anti-inflammatory growth factors and cytokines, e.g., IL4, IL-10, IL-13, IFN-alpha and/or transforming growth factor-beta, e.g., in the gut or the liver.

"Ammonia" is used to refer to gaseous ammonia ($NH_3$), ionic ammonia ($NH_4^+$), or a mixture thereof. In bodily fluids, gaseous ammonia and ionic ammonium exist in equilibrium: $NH_3 + H^+ \leftrightarrow NH_4^+$ Some clinical laboratory tests analyze total ammonia ($NH_3 + NH_4^+$) (Walker, 2012). In any embodiment of the invention, unless otherwise indicated, "ammonia" may refer to gaseous ammonia, ionic ammonia, and/or total ammonia.

"Detoxification" of ammonia is used to refer to the process or processes, natural or synthetic, by which toxic ammonia is removed and/or converted into one or more non-toxic molecules, including but not limited to: arginine, citrulline, methionine, histidine, lysine, asparagine, glutamine, tryptophan, or urea. The urea cycle, for example, enzymatically converts ammonia into urea for removal from the body in the urine. Because ammonia is a source of nitrogen for many amino acids, which are synthesized via numerous biochemical pathways, enhancement of one or more of those amino acid biosynthesis pathways may be used to incorporate excess nitrogen into non-toxic molecules. For example, arginine biosynthesis converts glutamate, which comprises one nitrogen atom, to arginine, which comprises four nitrogen atoms, thereby incorporating excess nitrogen into non-toxic molecules. In humans, arginine is not reabsorbed from the large intestine, and as a result, excess arginine in the large intestine is not considered to be harmful. Likewise, citrulline is not reabsorbed from the large intestine, and as a result, excess citrulline in the large intestine is not considered to be harmful. Arginine biosynthesis may also be modified to produce citrulline as an end product; citrulline comprises three nitrogen atoms and thus the modified pathway is also capable of incorporating excess nitrogen into non-toxic molecules.

"Arginine regulon," "arginine biosynthesis regulon," and "arg regulon" are used interchangeably to refer to the collection of operons in a given bacterial species that comprise the genes encoding the enzymes responsible for converting glutamate to arginine and/or intermediate metabolites, e.g., citrulline, in the arginine biosynthesis pathway. The arginine regulon also comprises operators, promoters, ARG boxes, and/or regulatory regions associated with those operons. The arginine regulon includes, but is not limited to, the operons encoding the arginine biosynthesis enzymes N-acetylglutamate synthetase, N-acetylglutamate kinase, N-acetylglutamylphosphate reductase, acetylornithine aminotransferase, N-acetylornithinase, ornithine transcarbamylase, argininosuccinate synthase, argininosuccinate lyase, carbamoylphosphate synthase, operators thereof, promoters thereof, ARG boxes thereof, and/or regulatory regions thereof. In some embodiments, the arginine regulon comprises an operon encoding ornithine acetyltransferase and associated operators, promoters, ARG boxes, and/or regulatory regions, either in addition to or in lieu of N-acetylglutamate synthetase and/or N-acetylornithinase. In some embodiments, one or more operons or genes of the arginine regulon may be present on a plasmid in the bacterium. In some embodiments, a bacterium may comprise multiple copies of any gene or operon in the arginine regulon, wherein one or more copies may be mutated or otherwise altered as described herein.

One gene may encode one enzyme, e.g., N-acetylglutamate synthetase (argA). Two or more genes may encode distinct subunits of one enzyme, e.g., subunit A and subunit B of carbamoylphosphate synthase (carA and carB). In some bacteria, two or more genes may each independently encode the same enzyme, e.g., ornithine transcarbamylase (argF and argI). In some bacteria, the arginine regulon includes, but is not limited to, argA, encoding N-acetylglutamate synthetase; argB, encoding N-acetylglutamate kinase; argC, encoding N-acetylglutamylphosphate reductase; argD, encoding acetylornithine aminotransferase; argE, encoding N-acetylornithinase; argG, encoding argininosuccinate synthase; argH, encoding argininosuccinate lyase; one or both of argF and argI, each of which independently encodes ornithine transcarbamylase; carA, encoding the small subunit of carbamoylphosphate synthase; carB, encoding the large subunit of carbamoylphosphate synthase; operons thereof; operators thereof; promoters thereof; ARG boxes thereof; and/or regulatory regions thereof. In some embodiments, the arginine regulon comprises argJ, encoding ornithine acetyltransferase (either in addition to or in lieu of N-acetylglutamate synthetase and/or N-acetylornithinase), operons thereof, operators thereof, promoters thereof, ARG boxes thereof, and/or regulatory regions thereof.

"Arginine operon," "arginine biosynthesis operon," and "arg operon" are used interchangeably to refer to a cluster of one or more of the genes encoding arginine biosynthesis enzymes under the control of a shared regulatory region comprising at least one promoter and at least one ARG box. In some embodiments, the one or more genes are co-transcribed and/or co-translated. Any combination of the genes encoding the enzymes responsible for arginine biosynthesis may be organized, naturally or synthetically, into an operon. For example, in B. subtilis, the genes encoding N-acetylglutamylphosphate reductase, N-acetylglutamate kinase, N-acetylornithinase, N-acetylglutamate kinase, acetylornithine aminotransferase, carbamoylphosphate synthase, and ornithine transcarbamylase are organized in a single operon, argCAEBD-carAB-argF (see, e.g., Table 2), under the control of a shared regulatory region comprising a promoter and ARG boxes. In E. coli K12 and Nissle, the genes encoding N-acetylornithinase, N-acetylglutamylphosphate reductase, N-acetylglutamate kinase, and argininosuccinate lyase are organized in two bipolar operons, argECBH. The operons encoding the enzymes responsible for arginine biosynthesis may be distributed at different loci across the chromosome. In unmodified bacteria, each operon may be repressed by arginine via ArgR. In some embodiments, arginine and/or intermediate byproduct production may be altered in the genetically engineered bacteria of the invention by modifying the expression of the enzymes encoded by the arginine biosynthesis operons as provided herein. Each arginine operon may be present on a plasmid or bacterial chromosome. In addition, multiple copies of any arginine operon, or a gene or regulatory region within an arginine operon, may be present in the bacterium, wherein one or more copies of the operon or gene or regulatory region may be mutated or otherwise altered as described herein. In some embodiments, the genetically engineered bacteria are engineered to comprise multiple copies of the same product (e.g., operon or gene or regulatory region) to enhance copy number or to comprise multiple different components of an operon performing multiple different functions.

"ARG box consensus sequence" refers to an ARG box nucleic acid sequence, the nucleic acids of which are known to occur with high frequency in one or more of the regulatory regions of argR, argA, argB, argC, argD, argE, argF, argG, argH, argI, argJ, carA, and/or carB. As described above, each arg operon comprises a regulatory region comprising at least one 18-nucleotide imperfect palindromic sequence, called an ARG box, that overlaps with the promoter and to which the repressor protein binds (Tian et al., 1992). The nucleotide sequences of the ARG boxes may vary for each operon, and the consensus ARG box sequence is $^{A}/_{T}$ nTGAAT $^{A}/_{T}$ $^{A}/_{T}$ $^{T}/_{A}$ $^{T}/_{A}$ ATTCAn $^{T}/_{A}$ (Maas, 1994). The arginine repressor binds to one or more ARG boxes to actively inhibit the transcription of the arginine biosynthesis enzyme(s) that are operably linked to that one or more ARG boxes.

"Mutant arginine regulon" or "mutated arginine regulon" is used to refer to an arginine regulon comprising one or more nucleic acid mutations that reduce or eliminate arginine-mediated repression of each of the operons that encode the enzymes responsible for converting glutamate to arginine and/or an intermediate byproduct, e.g., citrulline, in the arginine biosynthesis pathway, such that the mutant arginine regulon produces more arginine and/or intermediate byproduct than an unmodified regulon from the same bacterial subtype under the same conditions. In some embodiments, the genetically engineered bacteria comprise an arginine feedback resistant N-acetylglutamate synthase mutant, e.g., argA$^{fbr}$, and a mutant arginine regulon comprising one or more nucleic acid mutations in at least one ARG box for one or more of the operons that encode the arginine biosynthesis enzymes N-acetylglutamate kinase, N-acetylglutamylphosphate reductase, acetylornithine aminotransferase, N-acetylornithinase, ornithine transcarbamylase, argininosuccinate synthase, argininosuccinate lyase, and carbamoylphosphate synthase, thereby derepressing the regulon and enhancing arginine and/or intermediate byproduct biosynthesis. In some embodiments, the genetically engineered bacteria comprise a mutant arginine repressor comprising one or more nucleic acid mutations such that arginine repressor function is decreased or inactive, or the genetically engineered bacteria do not have an arginine repressor (e.g., the arginine repressor gene has been deleted), resulting in derepression of the regulon and enhancement of arginine and/or intermediate byproduct biosynthesis. In some embodiments, the genetically engineered bacteria comprise an arginine feedback resistant N-acetylglutamate synthase mutant, e.g., argA$^{fbr}$, a mutant arginine regulon comprising one or more nucleic acid mutations in at least one ARG box for each of the operons that encode the arginine biosynthesis enzymes, and/or a mutant or deleted arginine repressor. In some embodiments, the genetically engineered bacteria comprise an arginine feedback resistant N-acetylglutamate synthase mutant, e.g., argA$^{fbr}$ and a mutant arginine regulon comprising one or more nucleic acid mutations in at least one ARG box for each of the operons that encode the arginine biosynthesis enzymes. In some embodiments, the genetically engineered bacteria comprise an arginine feedback resistant N-acetylglutamate synthase mutant, e.g., argA$^{fbr}$ and a mutant or deleted arginine repressor. In some embodiments, the mutant arginine regulon comprises an operon encoding wild-type N-acetylglutamate synthetase and one or more nucleic acid mutations in at least one ARG box for said operon. In some embodiments, the mutant arginine regulon comprises an operon encoding wild-type N-acetylglutamate synthetase and mutant or deleted arginine repressor. In some embodiments, the mutant arginine regulon comprises an operon encoding ornithine acetyltransferase (either in addition to or in lieu of N-acetylglutamate synthetase and/or N-acetylornithinase) and one or more nucleic acid mutations in at least one ARG box for said operon.

The ARG boxes overlap with the promoter in the regulatory region of each arginine biosynthesis operon. In the mutant arginine regulon, the regulatory region of one or more arginine biosynthesis operons is sufficiently mutated to disrupt the palindromic ARG box sequence and reduce ArgR binding, but still comprises sufficiently high homology to the promoter of the non-mutant regulatory region to be recognized as the native operon-specific promoter. The operon comprises at least one nucleic acid mutation in at least one ARG box such that ArgR binding to the ARG box and to the regulatory region of the operon is reduced or eliminated. In some embodiments, bases that are protected from DNA methylation and bases that are protected from hydroxyl radical attack during ArgR binding are the primary targets for mutations to disrupt ArgR binding (see, e.g., Table 3). The promoter of the mutated regulatory region retains sufficiently high homology to the promoter of the non-mutant regulatory region such that RNA polymerase binds to it with sufficient affinity to promote transcription of the operably linked arginine biosynthesis enzyme(s). In some embodiments, the G/C:A/T ratio of the promoter of the mutant differs by no more than 10% from the G/C:A/T ratio of the wild-type promoter.

In some embodiments, more than one ARG box may be present in a single operon. In one aspect of these embodiments, at least one of the ARG boxes in an operon is altered to produce the requisite reduced ArgR binding to the regulatory region of the operon. In an alternate aspect of these embodiments, each of the ARG boxes in an operon is altered to produce the requisite reduced ArgR binding to the regulatory region of the operon.

"Reduced" ArgR binding is used to refer to a reduction in repressor binding to an ARG box in an operon or a reduction in the total repressor binding to the regulatory region of said operon, as compared to repressor binding to an unmodified ARG box and regulatory region in bacteria of the same subtype under the same conditions. In some embodiments, ArgR binding to a mutant ARG box and regulatory region of an operon is at least about 50% lower, at least about 60% lower, at least about 70% lower, at least about 80% lower, at least about 90% lower, or at least about 95% lower than ArgR binding to an unmodified ARG box and regulatory region in bacteria of the same subtype under the same conditions. In some embodiments, reduced ArgR binding to a mutant ARG box and regulatory region results in at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold increased mRNA expression of the one or more genes in the operon.

"ArgR" or "arginine repressor" is used to refer to a protein that is capable of suppressing arginine biosynthesis by regulating the transcription of arginine biosynthesis genes in the arginine regulon. When expression of the gene that encodes for the arginine repressor protein ("argR") is increased in a wild-type bacterium, arginine biosynthesis is decreased. When expression of argR is decreased in a wild-type bacterium, or if argR is deleted or mutated to inactivate arginine repressor function, arginine biosynthesis is increased.

Bacteria that "lack any functional ArgR" and "ArgR deletion bacteria" are used to refer to bacteria in which each arginine repressor has significantly reduced or eliminated activity as compared to unmodified arginine repressor from bacteria of the same subtype under the same conditions. Reduced or eliminated arginine repressor activity can result in, for example, increased transcription of the arginine biosynthesis genes and/or increased concentrations of arginine and/or intermediate byproducts, e.g., citrulline. Bacteria in which arginine repressor activity is reduced or eliminated can be generated by modifying the bacterial argR gene or by modifying the transcription of the argR gene. For example, the chromosomal argR gene can be deleted, can be mutated, or the argR gene can be replaced with an argR gene that does not exhibit wild-type repressor activity.

"Operably linked" refers a nucleic acid sequence, e.g., a gene encoding feedback resistant ArgA, that is joined to a regulatory region sequence in a manner which allows expression of the nucleic acid sequence, e.g., acts in cis. A regulatory region is a nucleic acid that can direct transcription of a gene of interest and may comprise promoter sequences, enhancer sequences, response elements, protein recognition sites, inducible elements, promoter control elements, protein binding sequences, 5' and 3' untranslated regions, transcriptional start sites, termination sequences, polyadenylation sequences, and introns.

An "inducible promoter" refers to a regulatory region that is operably linked to one or more genes, wherein expression of the gene(s) is increased in the presence of an inducer of said regulatory region. In some embodiments, the genetically engineered bacteria of the invention comprise an oxygen level-dependent promoter induced by low-oxygen, microaerobic, or anaerobic conditions. In some embodiments, the genetically engineered bacteria comprise a promoter induced by a molecule or metabolite, for example, a tissue-specific molecule or metabolite or a molecule or metabolite indicative of liver damage. In some embodiments, the metabolites may be gut specific. In some embodiments, the metabolite may be associated with hepatic encephalopathy, e.g., bilirubin. Non-limiting examples of molecules or metabolites include, e.g., bilirubin, aspartate aminotransferase, alanine aminotransferase, blood coagulation factors II, VII, IX, and X, alkaline phosphatase, gamma glutamyl transferase, hepatitis antigens and antibodies, alpha fetoprotein, anti-mitochondrial, smooth muscle, and anti-nuclear antibodies, iron, transferrin, ferritin, copper, ceruloplasmin, ammonia, and manganese in their blood and intestines. Promoters that respond to one of these molecules or their metabolites may be used in the genetically engineered bacteria provided herein. In some embodiments, the genetically engineered bacteria comprise a promoter induced by inflammation or an inflammatory response, e.g., RNS or ROS promoter. In some embodiments, the genetically engineered bacteria comprise a promoter induced by a metabolite that may or may not be naturally present (e.g., can be exogenously added) in the gut, e.g., arabinose and tetracycline.

"Exogenous environmental condition(s)" refer to setting(s) or circumstance(s) under which the promoter described herein is induced. The phrase "exogenous environmental conditions" is meant to refer to the environmental conditions external to the engineered microorganism, but endogenous or native to the host subject environment. Thus, "exogenous" and "endogenous" may be used interchangeably to refer to environmental conditions in which the environmental conditions are endogenous to a mammalian body, but external or exogenous to an intact microorganism cell. In some embodiments, the exogenous environmental conditions are specific to the gut of a mammal. In some embodiments, the exogenous environmental conditions are specific to the upper gastrointestinal tract of a mammal. In some embodiments, the exogenous environmental conditions are specific to the lower gastrointestinal tract of a mammal. In some embodiments, the exogenous environmental conditions are specific to the small intestine of a mammal. In some embodiments, exogenous environmental conditions refer to the presence of molecules or metabolites that are specific to the mammalian gut in a healthy or disease state (e.g., HE). In some embodiments, the exogenous environmental conditions are low-oxygen, microaerobic, or anaerobic conditions, such as the environment of the mammalian gut. In some embodiments, exogenous environmental conditions are molecules or metabolites that are specific to the mammalian gut, e.g., propionate. In some embodiments, the exogenous environmental condition is a tissue-specific or disease-specific metabolite or molecule(s). In some embodiments, the exogenous environmental condition is a low-pH environment. In some embodiments, the genetically engineered microorganism of the disclosure comprises a pH-dependent promoter. In some embodiments, the genetically engineered microorganism of the disclosure comprise an oxygen level-dependent promoter. In some aspects, bacteria have evolved transcription factors that are capable of sensing oxygen levels. Different signaling pathways may be triggered by different oxygen levels and occur with different kinetics.

An "oxygen level-dependent promoter" or "oxygen level-dependent regulatory region" refers to a nucleic acid sequence to which one or more oxygen level-sensing transcription factors is capable of binding, wherein the binding and/or activation of the corresponding transcription factor activates downstream gene expression.

Examples of oxygen level-dependent transcription factors include, but are not limited to, FNR, ANR, and DNR. Corresponding FNR-responsive promoters, ANR-responsive promoters, and DNR-responsive promoters are known in the art (see, e.g., Castiglione et al., 2009; Eiglmeier et al., 1989; Galimand et al., 1991; Hasegawa et al., 1998; Hoeren et al., 1993; Salmon et al., 2003), and non-limiting examples are shown in Table 1.

In a non-limiting example, a promoter (PfnrS) was derived from the *E. coli* Nissle fumarate and nitrate reductase gene S (fnrS) that is known to be highly expressed under conditions of low or no environmental oxygen (Durand and Storz, 2010; Boysen et al, 2010). The PfnrS promoter is activated under anaerobic conditions by the global transcriptional regulator FNR that is naturally found in Nissle. Under anaerobic conditions, FNR forms a dimer and binds to specific sequences in the promoters of specific genes under its control, thereby activating their expression. However, under aerobic conditions, oxygen reacts with iron-sulfur clusters in FNR dimers and converts them to an inactive form. In this way, the PfnrS inducible promoter is adopted to modulate the expression of proteins or RNA. PfnrS is used interchangeably in this application as FNRS, fnrs, FNR, P-FNRS promoter and other such related designations to indicate the promoter PfnrS.

TABLE 1

Examples of transcription factors and
responsive genes and regulatory regions

| Transcription Factor | Exemplary responsive genes, promoters, and/or regulatory regions: |
|---|---|
| FNR | nirB, ydfZ, pdhR, focA, ndH, hlyE, narK, narX, narG, yfiD, tdcD |
| ANR | arcDABC |
| DNR | norb, norC |

As used herein, a "gene cassette" or "operon" encoding a biosynthetic pathway refers to the two or more genes that are required to produce a gut barrier function enhancer molecule, e.g., butyrate, propionate. In addition to encoding a set of genes capable of producing said molecule, the gene cassette or operon may also comprise additional transcription and translation elements, e.g., a ribosome binding site.

As used herein, a "non-native" nucleic acid sequence refers to a nucleic acid sequence not normally present in a bacterium, e.g., an extra copy of an endogenous sequence, or a heterologous sequence such as a sequence from a different species, strain, or substrain of bacteria, or a sequence that is modified and/or mutated as compared to the unmodified sequence from bacteria of the same subtype. In some embodiments, the non-native nucleic acid sequence is a synthetic, non-naturally occurring sequence (see, e.g., Purcell et al., 2013). The non-native nucleic acid sequence may be a regulatory region, a promoter, a gene, and/or one or more genes in gene cassette. In some embodiments, "non-native" refers to two or more nucleic acid sequences that are not found in the same relationship to each other in nature. The non-native nucleic acid sequence, e.g., gene or gene cassette, may be present on a plasmid or bacterial chromosome. In some embodiments, the genetically engineered bacteria of the invention comprise a gene cassette that is operably linked to a directly or indirectly inducible promoter that is not associated with said gene cassette in nature, e.g., a FNR-responsive promoter operably linked to a butyrogenic gene cassette, or an arginine production cassette. In addition, multiple copies of the gene, gene cassette, or regulatory region may be present in the bacterium, wherein one or more copies may be mutated or otherwise altered as described herein. In some embodiments, the genetically engineered bacteria are engineered to comprise multiple copies of the same non-native nucleic acid sequence, e.g., gene, gene cassette, or regulatory region, in order to enhance copy number or to comprise multiple different components of a gene cassette performing multiple different functions.

"Constitutive promoter" refers to a promoter that is capable of facilitating continuous transcription of a coding sequence or gene under its control and/or to which it is operably linked. Constitutive promoters and variants are well known in the art and include, but are not limited to, BBa_J23100, a constitutive *Escherichia coli* $\sigma^s$ promoter (e.g., an osmY promoter (International Genetically Engineered Machine (iGEM) Registry of Standard Biological Parts Name BBa_J45992; BBa_J45993)), a constitutive *Escherichia coli* $\sigma^{32}$ promoter (e.g., htpG heat shock promoter (BBa_J45504)), a constitutive *Escherichia coli* $\sigma^{70}$ promoter (e.g., lacq promoter (BBa_J54200; BBa_J56015), *E. coli* CreABCD phosphate sensing operon promoter (BBa_J64951), GlnRS promoter (BBa_K088007), lacZ promoter (BBa_K119000; BBa_K119001); M13K07 gene I promoter (BBa_M13101); M13K07 gene II promoter (BBa_M13102), M13K07 gene III promoter (BBa_M13103), M13K07 gene IV promoter (BBa_M13104), M13K07 gene V promoter (BBa_M13105), M13K07 gene VI promoter (BBa_M13106), M13K07 gene VIII promoter (BBa_M13108), M13110 (BBa_M13110)), a constitutive *Bacillus subtilis* $\sigma^A$ promoter (e.g., promoter veg (BBa_K143013), promoter 43 (BBa_K143013), $P_{liaG}$ (BBa_K823000), $P_{lepA}$ (BBa_K823002), $P_{veg}$ (BBa_K823003)), a constitutive *Bacillus subtilis* e promoter (e.g., promoter ctc (BBa_K143010), promoter gsiB (BBa_K143011)), a *Salmonella* promoter (e.g., Pspv2 from *Salmonella* (BBa_K112706), Pspv from *Salmonella* (BBa_K112707)), a bacteriophage T7 promoter (e.g., T7 promoter (BBa_I712074; BBa_I719005; BBa_J34814; BBa_J64997; BBa_K113010; BBa_K113011; BBa_K113012; BBa_R0085; BBa_R0180; BBa_R0181; BBa_R0182; BBa_R0183; BBa_Z0251; BBa_Z0252; BBa_Z0253)), a bacteriophage SP6 promoter (e.g., SP6 promoter (BBa_J64998)), and functional fragments thereof.

As used herein, genetically engineered bacteria that "overproduce" arginine or an intermediate byproduct, e.g., citrulline, refer to bacteria that comprise a mutant arginine regulon. For example, the engineered bacteria may comprise a feedback resistant form of ArgA, and when the arginine feedback resistant ArgA is expressed, are capable of producing more arginine and/or intermediate byproduct than unmodified bacteria of the same subtype under the same conditions. The genetically engineered bacteria may alternatively or further comprise a mutant arginine regulon comprising one or more nucleic acid mutations in at least one ARG box for each of the operons that encode the arginine biosynthesis enzymes. The genetically engineered bacteria may alternatively or further comprise a mutant or deleted arginine repressor. In some embodiments, the genetically engineered bacteria produce at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold more arginine than unmodified bacteria of the same subtype under the same conditions. In some embodiments, the genetically engineered bacteria produce at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold more citrulline or other intermediate byproduct than unmodified bacteria of the same subtype under the same conditions. In some embodiments, the mRNA transcript levels of one or more of the arginine biosynthesis genes in the genetically engineered bacteria are at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold higher than the mRNA transcript levels in unmodified bacteria of the same subtype under the same conditions. In certain embodiments, the unmodified bacteria will not have detectable levels of arginine, intermediate byproduct, and/or transcription of the gene(s) in such operons. However, protein and/or transcription levels of arginine and/or intermediate byproduct will be detectable in the corresponding genetically engineered bacterium having the mutant arginine regulon. Transcription levels may be detected by directly measuring mRNA levels of the genes. Methods of measuring arginine and/or intermediate byproduct levels, as well as the levels of transcript expressed from the arginine biosynthesis genes, are known in the art. Arginine and citrulline, for example, may be measured by mass spectrometry.

"Gut" refers to the organs, glands, tracts, and systems that are responsible for the transfer and digestion of food, absorption of nutrients, and excretion of waste. In humans, the gut comprises the gastrointestinal tract, which starts at the mouth and ends at the anus, and additionally comprises the esophagus, stomach, small intestine, and large intestine. The gut also comprises accessory organs and glands, such as the spleen, liver, gallbladder, and pancreas. The upper gastrointestinal tract comprises the esophagus, stomach, and duodenum of the small intestine. The lower gastrointestinal tract comprises the remainder of the small intestine, i.e., the jejunum and ileum, and all of the large intestine, i.e., the cecum, colon, rectum, and anal canal. Bacteria can be found throughout the gut, e.g., in the gastrointestinal tract, and particularly in the intestines.

As used herein, the term "gene sequence" is meant to refer to a genetic sequence, e.g., a nucleic acid sequence. The gene sequence or genetic sequence is meant to include a complete gene sequence or a partial gene sequence. The gene sequence or genetic sequence is meant to include sequence that encodes a protein or polypeptide and is also meant to include genetic sequence that does not encode a protein or polypeptide, e.g., a regulatory sequence, leader sequence, signal sequence, or other non-protein coding sequence.

"Microorganism" refers to an organism or microbe of microscopic, submicroscopic, or ultramicroscopic size that typically consists of a single cell. Examples of microorganisms include bacteria, viruses, parasites, fungi, certain algae, and protozoa. In some aspects, the microorganism is engineered ("engineered microorganism") to produce one or more therapeutic molecules. In certain aspects, the microorganism is engineered to import and/or catabolize certain toxic metabolites, substrates, or other compounds from its environment, e.g., the gut. In certain aspects, the microorganism is engineered to synthesize certain beneficial metabolites, molecules, or other compounds (synthetic or naturally occurring) and release them into its environment. In certain embodiments, the engineered microorganism is an engineered bacterium. In certain embodiments, the engineered microorganism is an engineered virus.

"Non-pathogenic bacteria" refer to bacteria that are not capable of causing disease or harmful responses in a host. In some embodiments, non-pathogenic bacteria are commensal bacteria. Examples of non-pathogenic bacteria include, but are not limited to *Bacillus, Bacteroides, Bifidobacterium, Brevibacteria, Clostridium, Enterococcus, Escherichia coli, Lactobacillus, Lactococcus, Saccharomyces,* and *Staphylococcus,* e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis,* and *Saccharomyces boulardii* (Sonnenborn et al., 2009; Dinleyici et al., 2014; U.S. Pat. Nos. 6,835,376; 6,203,797; 5,589,168; 7,731,976). Naturally pathogenic bacteria may be genetically engineered to provide reduce or eliminate pathogenicity.

As used herein, "payload" refers to one or more polynucleotides and/or polypeptides of interest to be produced by a genetically engineered microorganism, such as a bacteria or a virus. In some embodiments, the payload is encoded by a gene or multiple genes or an operon. In some embodiments, the one or more genes and/or operon(s) comprising the payload are endogenous to the microorganism. In some embodiments, the one or more elements of the payload is derived from a different microorganism and/or organism. In some embodiments, the payload is a therapeutic payload. In some embodiments, the payload is encoded by genes for the biosynthesis of a molecule. In some embodiments, the payload is encoded by genes for the metabolism, catabolism, or degradation of a molecule. In some embodiments, the payload is encoded by genes for the importation of a molecule. In some embodiments, the payload is encoded by genes for the exportation of a molecule. In some embodiments, the payload is a regulatory molecule(s), e.g., a transcriptional regulator such as FNR. In some embodiments, the payload comprises a regulatory element, such as a promoter or a repressor. In some embodiments, the payload comprises an inducible promoter, such as from FNRS. In some embodiments the payload comprises a repressor element, such as a kill switch. In alternate embodiments, the payload is produced by a biosynthetic or biochemical pathway, wherein the biosynthetic or biochemical pathway may optionally be endogenous to the microorganism. In some embodiments, the genetically engineered microorganism comprises two or more payloads. Non-limiting examples of payload(s) include one or more of the following: (1) ArgAfbr, (2) mutated ArgR, (3) mutated ArgG. Other exemplary payloads include mutated sequence(s) that result in an auxotrophy, e.g., thyA auxotrophy, kill switch circuit, antibiotic resistance circuits, transporter sequence for importing biological molecules or substrates, secretion circuit.

"Probiotic" is used to refer to live, non-pathogenic microorganisms, e.g., bacteria, which can confer health benefits to a host organism that contains an appropriate amount of the microorganism. In some embodiments, the host organism is a mammal. In some embodiments, the host organism is a human. Some species, strains, and/or subtypes of non-pathogenic bacteria are currently recognized as probiotic bacteria. Examples of probiotic bacteria include, but are not limited to, *Bifidobacteria, Escherichia coli, Lactobacillus,* and *Saccharomyces,* e.g., *Bifidobacterium bifidum, Enterococcus faecium, Escherichia coli* strain Nissle, *Lactobacillus acidophilus, Lactobacillus bulgaricus, Lactobacillus paracasei, Lactobacillus plantarum,* and *Saccharomyces boulardii* (Dinleyici et al., 2014; U.S. Pat. Nos. 5,589,168; 6,203,797; 6,835,376). The probiotic may be a variant or a mutant strain of bacterium (Arthur et al., 2012; Cuevas-Ramos et al., 2010; Olier et al., 2012; Nougayrede et al., 2006). Non-pathogenic bacteria may be genetically engineered to enhance or improve desired biological properties, e.g., survivability. Non-pathogenic bacteria may be genetically engineered to provide probiotic properties. Probiotic bacteria may be genetically engineered to enhance or improve probiotic properties.

E. Nissle is a probiotic which has been used for the treatment of various diseases of the gut, including diarrhea, diverticulitis and inflammatory bowel disease. *E. coli* Nissle 1917 has been shown to have anti-inflammatory effects in a number of studies. For example a reduction in the pro-inflammatory cytokine tumor necrosis factor-α both in the intestine from colitic rats, and in plasma and lungs in mice treated with LPS, resulting in a systemic beneficial effect, which was associated with inhibited production of the T cell cytokines and by down-regulation of IgG release from splenocyte-derived B cells (Arribas et al., A probiotic strain of *Escherichia coli,* Nissle 1917, given orally exerts local and systemic anti-inflammatory effects in lipopolysaccharide-induced sepsis in mice; Br J Pharmacol. 2009 July; 157(6): 1024-1033, and references therein).

As used herein, "stably maintained" or "stable" bacterium is used to refer to a bacterial host cell carrying non-native genetic material, e.g., a feedback resistant argA gene, mutant arginine repressor, and/or other mutant arginine regulon that is incorporated into the host genome or propagated on a self-replicating extra-chromosomal plasmid, such that the non-native genetic material is retained, expressed, and propagated. The stable bacterium is capable of survival and/or growth in vitro, e.g., in medium, and/or in vivo, e.g., in the gut. For example, the stable bacterium may be a genetically engineered bacterium comprising a gene encoding a feedback resistant ArgA, in which the plasmid or chromosome carrying the a feedback resistant ArgA gene is stably maintained in the bacterium, such that feedback resistant ArgA can be expressed in the bacterium, and the bacterium is capable of survival and/or growth in vitro and/or in vivo.

As used herein, the terms "modulate" and "treat" and their cognates refer to an amelioration of a disease, disorder, and/or condition, or at least one discernible symptom thereof. In another embodiment, "modulate" and "treat" refer to an amelioration of at least one measurable physical parameter, not necessarily discernible by the patient. In another embodiment, "modulate" and "treat" refer to inhibiting the progression of a disease, disorder, and/or condition, either physically (e.g., stabilization of a discernible symptom), physiologically (e.g., stabilization of a physical parameter), or both. In another embodiment, "modulate" and "treat" refer to slowing the progression or reversing the progression of a disease, disorder, and/or condition. As used herein, "prevent" and its cognates refer to delaying the onset or reducing the risk of acquiring a given disease, disorder and/or condition or a symptom associated with such disease, disorder, and/or condition.

Those in need of treatment may include individuals already having a particular medical disorder, as well as those at risk of having, or who may ultimately acquire the disorder. The need for treatment is assessed, for example, by the presence of one or more risk factors associated with the development of a disorder, the presence or progression of a disorder, or likely receptiveness to treatment of a subject having the disorder. Primary hyperammonemia is caused by UCDs, which are autosomal recessive or X-linked inborn errors of metabolism for which there are no known cures. Hyperammonemia can also be secondary to other disruptions of the urea cycle, e.g., toxic metabolites, infections, and/or substrate deficiencies. Hyperammonemia can also contribute to other pathologies. For example, Huntington's disease is an autosomal dominant disorder for which there are no known cures. Urea cycle abnormalities characterized by hyperammonemia, high blood citrulline, and suppression of urea cycle enzymes may contribute to the pathology of Huntington's disease, an autosomal dominant disorder for which there are no known cures. Treating hyperammonemia may encompass reducing or eliminating excess ammonia and/or associated symptoms, and does not necessarily encompass the elimination of the underlying hyperammonemia-associated disorder.

As used herein a "pharmaceutical composition" refers to a preparation of genetically engineered bacteria of the invention with other components such as a physiologically suitable carrier and/or excipient.

The phrases "physiologically acceptable carrier" and "pharmaceutically acceptable carrier" which may be used interchangeably refer to a carrier or a diluent that does not cause significant irritation to an organism and does not abrogate the biological activity and properties of the administered bacterial compound. An adjuvant is included under these phrases.

The term "excipient" refers to an inert substance added to a pharmaceutical composition to further facilitate administration of an active ingredient. Examples include, but are not limited to, calcium bicarbonate, calcium phosphate, various sugars and types of starch, cellulose derivatives, gelatin, vegetable oils, polyethylene glycols, and surfactants, including, for example, polysorbate 20.

The terms "therapeutically effective dose" and "therapeutically effective amount" are used to refer to an amount of a compound that results in prevention, delay of onset of symptoms, or amelioration of symptoms of a condition, e.g., hyperammonemia. A therapeutically effective amount may, for example, be sufficient to treat, prevent, reduce the severity, delay the onset, and/or reduce the risk of occurrence of one or more symptoms of a disorder associated with elevated ammonia concentrations. A therapeutically effective amount, as well as a therapeutically effective frequency of administration, can be determined by methods known in the art and discussed below.

As used herein, the term "polypeptide" includes "polypeptide" as well as "polypeptides," and refers to a molecule composed of amino acid monomers linearly linked by amide bonds (i.e., peptide bonds). The term "polypeptide" refers to any chain or chains of two or more amino acids, and does not refer to a specific length of the product. Thus, "peptides," "dipeptides," "tripeptides, "oligopeptides," "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including but not limited to glycosylation, acetylation, phosphorylation, amidation, derivatization, proteolytic cleavage, or modification by non-naturally occurring amino acids. A polypeptide may be derived from a natural biological source or produced by recombinant technology. In other embodiments, the polypeptide is produced by the genetically engineered bacteria or virus of the current invention. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides, which do not possess a defined three-dimensional structure, but rather can adopt a large number of different conformations, are referred to as unfolded. The term "peptide" or "polypeptide" may refer to an amino acid sequence that corresponds to a protein or a portion of a protein or may refer to an amino acid sequence that corresponds with non-protein sequence, e.g., a sequence selected from a regulatory peptide sequence, leader peptide sequence, signal peptide sequence, linker peptide sequence, and other peptide sequence.

An "isolated" polypeptide or a fragment, variant, or derivative thereof refers to a polypeptide that is not in its natural milieu. No particular level of purification is required. Recombinantly produced polypeptides and proteins expressed in host cells, including but not limited to bacterial or mammalian cells, are considered isolated for purposed of the invention, as are native or recombinant polypeptides which have been separated, fractionated, or partially or substantially purified by any suitable technique. Recombinant peptides, polypeptides or proteins refer to peptides, polypeptides or proteins produced by recombinant DNA techniques, i.e. produced from cells, microbial or mammalian, transformed by an exogenous recombinant DNA expression construct encoding the polypeptide. Proteins or peptides expressed in most bacterial cultures will typically be free of glycan. Fragments, derivatives, analogs or variants of the foregoing polypeptides, and any combination thereof are also included as polypeptides. The terms "fragment," "variant," "derivative" and "analog" include polypeptides having an amino acid sequence sufficiently similar to the amino acid sequence of the original peptide and include any polypeptides, which retain at least one or more properties of the corresponding original polypeptide. Fragments of polypeptides of the present invention include proteolytic fragments, as well as deletion fragments. Fragments also include specific antibody or bioactive fragments or immunologically active fragments derived from any polypeptides described herein. Variants may occur naturally or be non-naturally occurring. Non-naturally occurring variants may be produced using mutagenesis methods known in the art. Variant polypeptides may comprise conservative or non-conservative amino acid substitutions, deletions or additions.

Polypeptides also include fusion proteins. As used herein, the term "variant" includes a fusion protein, which comprises a sequence of the original peptide or sufficiently similar to the original peptide. As used herein, the term "fusion protein" refers to a chimeric protein comprising amino acid sequences of two or more different proteins. Typically, fusion proteins result from well known in vitro recombination techniques. Fusion proteins may have a similar structural function (but not necessarily to the same extent), and/or similar regulatory function (but not necessarily to the same extent), and/or similar biochemical function (but not necessarily to the same extent) and/or immunological activity (but not necessarily to the same extent) as the individual original proteins which are the components of the fusion proteins. "Derivatives" include but are not limited to peptides, which contain one or more naturally occurring amino acid derivatives of the twenty standard amino acids. "Similarity" between two peptides is determined by comparing the amino acid sequence of one peptide to the sequence of a second peptide. An amino acid of one peptide is similar to the corresponding amino acid of a second peptide if it is identical or a conservative amino acid substitution. Conservative substitutions include those described in Dayhoff, M. O., ed., The Atlas of Protein Sequence and Structure 5, National Biomedical Research Foundation, Washington, D.C. (1978), and in Argos, EMBO J. 8 (1989), 779-785. For example, amino acids belonging to one of the following groups represent conservative changes or substitutions: Ala, Pro, Gly, Gln, Asn, Ser, Thr; Cys, Ser, Tyr, Thr; Val, Ile, Leu, Met, Ala, Phe; Lys, Arg, His; Phe, Tyr, Trp, His; and Asp, Glu.

As used herein, the term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar. Preferably, variants will be sufficiently similar to the amino acid sequence of the peptides of the invention. Such variants generally retain the functional activity of the peptides of the present invention. Variants include peptides that differ in amino acid sequence from the native and wt peptide, respectively, by way of one or more amino acid deletion(s), addition(s), and/or substitution(s). These may be naturally occurring variants as well as artificially designed ones.

As used herein the term "linker", "linker peptide" or "peptide linkers" or "linker" refers to synthetic or non-native or non-naturally-occurring amino acid sequences that connect or link two polypeptide sequences, e.g., that link two polypeptide domains. As used herein the term "synthetic" refers to amino acid sequences that are not naturally occurring. Exemplary linkers are described herein. Additional exemplary linkers are provided in US 20140079701, the contents of which are herein incorporated by reference in its entirety.

As used herein the term "codon-optimized sequence" refers to a sequence, which was modified from an existing coding sequence, or designed, for example, to improve translation in an expression host cell or organism of a transcript RNA molecule transcribed from the coding sequence, or to improve transcription of a coding sequence. Codon optimization includes, but is not limited to, processes including selecting codons for the coding sequence to suit the codon preference of the expression host organism.

Many organisms display a bias or preference for use of particular codons to code for insertion of a particular amino acid in a growing polypeptide chain. Codon preference or codon bias, differences in codon usage between organisms, is allowed by the degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

As used herein, the terms "secretion system" or "secretion protein" refers to a native or non-native secretion mechanism capable of secreting or exporting the protein of interest or therapeutic protein from the microbial, e.g., bacterial cytoplasm. The secretion system may comprise a single protein or may comprise two or more proteins assembled in a complex e.g. HlyBD. Non-limiting examples of secretion systems for gram negative bacteria include the modified type III flagellar, type I (e.g., hemolysin secretion system), type II, type IV, type V, type VI, and type VII secretion systems, resistance-nodulation-division (RND) multi-drug efflux pumps, various single membrane secretion systems. Non-liming examples of secretion systems for gram positive bacteria include Sec and TAT secretion systems. In some embodiments, the protein(s) of interest or therapeutic protein(s) include a "secretion tag" of either RNA or peptide origin to direct the protein(s) of interest or therapeutic protein(s) to specific secretion systems. In some embodiments, the secretion system is able to remove this tag before secreting the protein(s) of interest or therapeutic protein(s) from the engineered bacteria. For example, in Type V auto-secretion-mediated secretion the N-terminal peptide secretion tag is removed upon translocation of the "passenger" peptide from the cytoplasm into the periplasmic compartment by the native Sec system. Further, once the auto-secretor is translocated across the outer membrane the C-terminal secretion tag can be removed by either an autocatalytic or protease-catalyzed e.g., OmpT cleavage thereby releasing the protein(s) of interest or therapeutic protein(s) into the extracellular milieu.

As used herein, the term "transporter" is meant to refer to a mechanism, e.g., protein or proteins, for importing a molecule, e.g., amino acid, toxin, metabolite, substrate, etc. into the microorganism from the extracellular milieu.

The articles "a" and "an," as used herein, should be understood to mean "at least one," unless clearly indicated to the contrary.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

The genetically engineered bacteria disclosed herein are capable of reducing excess ammonia and converting ammonia and/or nitrogen into alternate byproducts. In some embodiments, the genetically engineered bacteria are naturally non-pathogenic bacteria. In some embodiments, the genetically engineered bacteria are commensal bacteria. In some embodiments, the genetically engineered bacteria are probiotic bacteria. In some embodiments, the genetically engineered bacteria are naturally pathogenic bacteria that are modified or mutated to reduce or eliminate pathogenicity. Exemplary bacteria are described in US Patent Publication US20160333326 and International Patent Publication WO2017139697, the contents of which is herein incorporated by reference in its entirety.

In some embodiments, the genetically engineered bacteria comprise circuitry in which one or more genes are under control of an inducible promoter. In some embodiments, the inducible promoter is a low-oxygen inducible promoter. In some embodiments, the promoter is inducible by inflammatory molecules, e.g., reactive nitrogen or reactive oxygen species (RNS or ROS). In some embodiments, the promoters are inducible by one or more nutritional and/or chemical inducer(s) and/or metabolite(s). Non-limiting examples of inducers include tetracycline, arabinose, IPTG, lactose, rhamnose, propionate.

In some embodiments, the genes are under control of a constitutive promoter. Suitable inducible promoters/promoter systems, and constitutive promoters are described for example in co-owned US Patent Publication US20160333326 and International Patent Publication WO2017139697, the contents of each of which is herein incorporated by reference in its entirety. In some embodiments, it is desirable to pre-induce activity of one or more ammonia catabolism circuitry components and/or other protein(s) of interest prior to administration. In such situations, the strains are pre-loaded with active payload or protein of interest. In such instances, the genetically engineered bacteria of the invention express one or more ammonia catabolism circuitry and/or other protein(s) of interest, under conditions provided in bacterial culture during cell growth, expansion, purification, fermentation, and/or manufacture prior to administration in vivo. Such culture conditions can be provided in a flask, fermenter or other appropriate culture vessel, e.g., used during cell growth, cell expansion, fermentation, recovery, purification, formulation, and/or manufacture. As used herein, the term "bacterial culture" or "bacterial cell culture" or "culture" refers to bacterial cells or microorganisms, which are maintained or grown in vitro during several production processes, including cell growth, cell expansion, recovery, purification, fermentation, and/or manufacture. As used herein, the term "fermentation" refers to the growth, expansion, and maintenance of bacteria under defined conditions. Fermentation may occur under a number of different cell culture conditions, including anaerobic or low oxygen or oxygenated conditions, in the presence of inducers, nutrients, at defined temperatures, and the like. Methods for induction of ammonia strains are inter alia described in co-owned US Patent Publication US20160333326 and International Patent Publication WO2017139697, the contents of each of which is herein incorporated by reference in its entirety.

An auxotrophic modification is intended to cause bacteria to die in the absence of an exogenously added nutrient essential for survival or growth because they lack the gene(s) necessary to produce that essential nutrient. In some embodiments, any of the genetically engineered bacteria described herein also comprise a deletion or mutation in one or more gene(s) required for cell survival and/or growth. Auxotrophic mutations are described in co-owned US Patent Publication US20160333326 and International Patent Publication WO2017139697, the contents of each of which is herein incorporated by reference in its entirety.

In some embodiments, the genetically engineered bacteria comprise multi-layered genetic regulatory circuits for expressing the constructs described herein. The genetic regulatory circuits are useful to screen for mutant bacteria that produce a component of an ammonia consuming circuitry or rescue an auxotroph. In certain embodiments, the invention provides methods for selecting genetically engineered bacteria that produce one or more genes of interest. Such regulatory circuitry is described in described in co-owned International Patent Publications WO2016/210378, US Patent Publication US20160333326 and International Patent Publication WO2017139697, the contents of each of which is herein incorporated by reference in its entirety.

In some embodiments, the genetically engineered bacteria also comprise a kill switch. The kill switch is intended to actively kill engineered microbes in response to external stimuli. As opposed to an auxotrophic mutation where bacteria die because they lack an essential nutrient for survival, the kill switch is triggered by a particular factor in the environment that induces the production of toxic molecules within the microbe that cause cell death. Exemplary kill switches are described in co-owned International Patent Publications WO2016/210373, US Patent Publication US20160333326 and International Patent Publication WO2017139697, the contents of each of which is herein incorporated by reference in its entirety.

In some embodiments, the genetically engineered bacteria also comprise a plasmid that has been modified to create a host-plasmid mutual dependency. In certain embodiments, the mutually dependent host-plasmid platform. Examples of such platforms are described in Wright et al., 2015 GeneGuard: A Modular Plasmid System Designed for Biosafety; ACS Synth. Biol., 2015, 4 (3), pp 307-316, and in co-owned US Patent Publication US20160333326 and International Patent Publication WO2017139697, the contents of each of which is herein incorporated by reference in its entirety.

In some embodiments, any of the gene(s) or gene cassette(s) of the present disclosure may be integrated into the bacterial chromosome at one or more integration sites. One or more copies of the gene or gene cassette may be integrated into the bacterial chromosome. Having multiple copies of the gene or gene cassette integrated into the chromosome allows for greater production of the payload, and also permits fine-tuning of the level of expression. Alternatively, different circuits described herein, such as any of the kill-switch circuits, in addition to the therapeutic gene(s) or gene cassette(s) could be integrated into the bacterial chromosome at one or more different integration sites to perform multiple different functions. Exemplary integration sites, e.g. *E coli* Nissle integration sites are described in in co-owned US Patent Publication US20160333326 and International Patent Publication WO2017139697, the contents of each of which is herein incorporated by reference in its entirety.

In some embodiments, the genetically engineered bacteria further comprise a native secretion mechanism or non-native secretion mechanism that is capable of secreting a molecule from the bacterial cytoplasm in the extracellular environment. Many bacteria have evolved sophisticated secretion systems to transport substrates across the bacterial cell envelope. Substrates, such as small molecules, proteins, and DNA, may be released into the extracellular space or periplasm (such as the gut lumen or other space), injected into a target cell, or associated with the bacterial membrane. Exemplary native and non-native secretion systems, secretion tags, diffusible outer membrane mutations and phenotypes, and methods and compositions useful for the secretion of active proteins are described in co-owned US Patent Publication US20160333326 and International Patent Publication WO2017139697, the contents of each of which is herein incorporated by reference in its entirety.

Ammonia Consumption and Arginine Production Circuit

In the ammonia consumption/arginine production circuit described herein below and in more detail in PCT/US2016/034200, filed May 25, 2016 and Ser. No. 15/164,828 filed May 25, 2016, published as US20160333326, and PCT/US2015/064140, filed Dec. 4, 2015, and U.S. Pat. No. 9,487,764, filed Dec. 4, 2015, ammonia is taken up by a bacterium (e.g., *E. coli* Nissle), converted to glutamate, and glutamate is subsequently metabolized to arginine. Arginine then ultimately exits the bacterial cell. As such this circuit is suitable for the consumption of ammonia, reducing ammonia levels in the gut and in the blood, and at the same time producing arginine.

In some embodiments, the genetically engineered bacteria that produce L-Arginine and/or consume ammonia comprise one or more gene sequences encoding one or more enzymes of the L-Arginine biosynthetic pathway. In some embodiments, the genetically engineered bacteria comprise one or more gene sequences encoding one or more enzymes that are capable of incorporating ammonia into glutamate, and converting glutamate to arginine. In some embodiments, the genetically engineered bacteria comprise an Arginine operon. In some embodiments, the genetically engineered bacteria comprise the Arginine operon of *E. coli*. In some embodiments, the genetically engineered bacteria comprise the Arginine operon of another bacteria. In any of these embodiments, the arginine repressor (ArgR) optionally may be deleted, mutated, or modified so as to diminish or obliterate its repressor function.

"Arginine operon," "arginine biosynthesis operon," and "arg operon" are used interchangeably to refer to a cluster of one or more of the genes encoding arginine biosynthesis enzymes under the control of a shared regulatory region comprising at least one promoter and at least one ARG box. In some embodiments, the one or more genes are co-transcribed and/or co-translated.

"Mutant arginine regulon" or "mutated arginine regulon" is used to refer to an arginine regulon comprising one or more nucleic acid mutations that reduce or eliminate arginine-mediated repression of each of the operons that encode the enzymes responsible for converting glutamate to arginine in the arginine biosynthesis pathway, such that the mutant arginine regulon produces more arginine and/or intermediate byproduct than an unmodified regulon from the same bacterial subtype under the same conditions.

In bacteria such as *Escherichia coli* (*E. coli*), the arginine biosynthesis pathway is capable of converting glutamate to arginine in an eight-step enzymatic process described in in PCT/US2016/034200, filed May 25, 2016 and Ser. No. 15/164,828 filed May 25, 2016, published as US20160333326, and PCT/US2015/064140, filed Dec. 4, 2015, and U.S. Pat. No. 9,487,764, filed Dec. 4, 2015, the contents of each of which is herein incorporated by reference in its entirety. All of the genes encoding these enzymes are subject to repression by arginine via its interaction with ArgR to form a complex that binds to the regulatory region of each gene and inhibits transcription. N-acetylglutamate synthetase is also subject to allosteric feedback inhibition at the protein level by arginine alone.

In some engineered bacteria, the arginine regulon includes, but is not limited to, argA, encoding N-acetylglutamate synthetase; argB, encoding N-acetylglutamate kinase; argC, encoding N-acetylglutamylphosphate reductase; argD, encoding acetylornithine aminotransferase; argE, encoding N-acetylornithinase; argC, encoding argininosuccinate synthase; argH, encoding argininosuccinate lyase; one or both of argF and argI, each of which independently encodes ornithine transcarbamylase; carA, encoding the small subunit of carbamoylphosphate synthase; carB, encoding the large subunit of carbamoylphosphate synthase; operons thereof; operators thereof; promoters thereof; ARG boxes thereof; and/or regulatory regions thereof. In some embodiments, the arginine regulon comprises argJ, encoding ornithine acetyltransferase (either in addition to or in lieu of N-acetylglutamate synthetase and/or N-acetylornithinase), operons thereof, operators thereof, promoters thereof, ARG boxes thereof, and/or regulatory regions thereof.

In some embodiments, the genetically engineered bacteria comprise an arginine biosynthesis pathway and are capable of producing arginine and/or consuming ammonia. In a more specific aspect, the genetically engineered bacteria comprise a mutant arginine regulon in which one or more operons encoding arginine biosynthesis enzyme(s) is derepressed to produce more arginine than unmodified bacteria of the same subtype under the same conditions. In some embodiments, the genetically engineered bacteria overproduce arginine. In some embodiments, the genetically engineered bacteria consume ammonia. In some embodiments, the genetically engineered bacteria overproduce arginine and consume ammonia.

Each operon is regulated by a regulatory region comprising at least one promoter and at least one ARG box, which control repression and expression of the arginine biosynthesis genes in said operon. In some embodiments, the genetically engineered bacteria comprise an arginine regulon comprising one or more nucleic acid mutations that reduce or eliminate arginine-mediated repression of one or more of the operons that encode the enzymes responsible for converting glutamate to arginine in the arginine biosynthesis pathway. Reducing or eliminating arginine-mediated repression may be achieved by reducing or eliminating ArgR repressor binding (e.g., by mutating or deleting the arginine repressor or by mutating at least one ARG box for each of the operons that encode the arginine biosynthesis enzymes) and/or arginine binding to N-acetylglutamate synthetase (e.g., by mutating the N-acetylglutamate synthetase to produce an arginine feedback resistant N-acetylglutamate synthase mutant, e.g., argAfbr).

In some embodiments, the reduction or elimination of arginine-mediated repression may be achieved by reducing or eliminating ArgR repressor binding, e.g., by mutating at least one ARG box for one or more of the operons that encode the arginine biosynthesis enzymes or by mutating or deleting the arginine repressor and/or by reducing or eliminating arginine binding to N-acetylglutamate synthetase (e.g., by mutating the N-acetylglutamate synthetase to produce an arginine feedback resistant N-acetylglutamate synthase mutant, e.g., argAfbr).

"ArgR" or "arginine repressor" is used to refer to a protein that is capable of suppressing arginine biosynthesis by regulating the transcription of arginine biosynthesis genes in the arginine regulon. Bacteria that "lack any functional ArgR" and "ArgR deletion bacteria" are used to refer to bacteria in which each arginine repressor has significantly reduced or eliminated activity as compared to unmodified arginine repressor from bacteria of the same subtype under the same conditions. ARG box refers to an nucleic acid sequence which comprises a consensus sequence, and which is known to occur with high frequency in one or more of the regulatory regions of argR, argA, argB, argC, argD, argE, argF, argG, argH, argI, argJ, carA, and/or carB.

In some embodiments, the genetically engineered bacteria comprise a mutant arginine regulon comprising one or more nucleic acid mutations in at least one ARG box for one or more of the operons that encode the arginine biosynthesis enzymes N-acetylglutamate kinase, N-acetylglutamylphosphate reductase, acetylornithine aminotransferase, N-acetylornithinase, ornithine transcarbamylase, argininosuccinate synthase, argininosuccinate lyase, and carbamoylphosphate synthase, such that the arginine regulon is derepressed and biosynthesis of arginine and/or an intermediate byproduct, e.g., citrulline, is enhanced. Such genetically engineered bacteria, mutant Arg boxes and exemplary mutant arginine regulons are described in PCT/US2016/034200, filed May 25, 2016 and Ser. No. 15/164,828 filed May 25, 2016, published as US20160333326, and PCT/US2015/064140, filed Dec. 4, 2015, and U.S. Pat. No. 9,487,764, filed Dec. 4, 2015, the contents of each of which is herein incorporated by reference it its entirety.

In some embodiments, the genetically engineered bacteria lack a functional ArgR repressor and therefore ArgR repressor-mediated transcriptional repression of each of the arginine biosynthesis operons is reduced or eliminated. Genetically engineered bacteria according to the present disclosure that lack a functional ArgR repressor are described in PCT/US2016/034200, filed May 25, 2016 and Ser. No. 15/164,828 filed May 25, 2016, published as US20160333326, and PCT/US2015/064140, filed Dec. 4, 2015, and U.S. Pat. No. 9,487,764, filed Dec. 4, 2015, the contents of each of which is herein incorporated by reference it its entirety. In some embodiments, the engineered bacteria comprise a mutant arginine repressor comprising one or more nucleic acid mutations such that arginine repressor function is decreased or inactive. In some embodiments, the genetically engineered bacteria do not have an arginine repressor (e.g., the arginine repressor gene has been deleted), resulting in derepression of the regulon and enhancement of arginine and/or intermediate byproduct biosynthesis and/or increased ammonia consumption. Bacteria in which arginine repressor activity is reduced or eliminated can be generated by modifying the bacterial argR gene or by modifying the transcription of the argR gene. In some embodiments, each copy of a functional argR gene normally present in a corresponding wild-type bacterium is independently deleted or rendered inactive by one or more nucleotide deletions, insertions, or substitutions or is deleted.

In some embodiments, the genetically engineered bacteria comprise an arginine feedback resistant N-acetylglutamate synthase mutant, e.g., argA$^{fbr}$ (see, e.g., Eckhardt et al., 1975; Rajagopal et al., 1998). Genetically engineered bacteria according to the present disclosure comprising argAfbr are described in PCT/US2016/034200, filed May 25, 2016 and Ser. No. 15/164,828 filed May 25, 2016, published as US20160333326, and PCT/US2015/064140, filed Dec. 4, 2015, and U.S. Pat. No. 9,487,764, filed Dec. 4, 2015, the contents of each of which is herein incorporated by reference it its entirety. In some embodiments, the genetically engineered bacteria comprise a mutant arginine regulon comprising an arginine feedback resistant ArgA, and when the arginine feedback resistant ArgA is expressed, are capable of producing more arginine and/or an intermediate byproduct than unmodified bacteria of the same subtype under the same conditions. The feedback resistant argA gene can be present on a plasmid or chromosome, e.g., in one or more copies at one or more integration sites. Multiple distinct feedback resistant N-acetylglutamate synthetase proteins are known in the art and may be combined in the genetically engineered bacteria. In some embodiments, the argA$^{fbr}$ gene is expressed under the control of a constitutive promoter. In some embodiments, the argA$^{fbr}$ gene is expressed under the control of a promoter that is induced by tumor microenvironment. In some embodiments, the argA$^{fbr}$ gene is expressed under the control of a promoter that is induced under low oxygen conditions, e.g., an FNR promoter.

The nucleic acid sequence of an exemplary argAfbr sequence is shown in SEQ ID NO: 1. The polypeptide sequence of an exemplary argAfbr sequence is shown in SEQ ID NO: 2.

In any of these embodiments, the genetically engineered bacteria may further comprise a gene sequences encoding a butyrate biosynthetic pathway. Non limiting examples of such butyrate biosynthetic pathways are described in U.S. Pat. No. 9,688,967 and International Patent Application PCT/US2017/017552, filed Feb. 10, 2017, published as WO2017139697, the contents of each of which is herein incorporated by reference in its entirety.

Pharmaceutical Compositions

Pharmaceutical compositions comprising the genetically engineered microorganisms of the invention may be used to treat, manage, ameliorate, and/or prevent a disorder associated with hyperammonemia or symptom(s) associated with diseases or disorders associated with hyperammonemia. Pharmaceutical compositions of the invention comprising one or more genetically engineered bacteria, and/or one or more genetically engineered yeast or virus, alone or in combination with prophylactic agents, therapeutic agents, and/or pharmaceutically acceptable carriers are provided.

In certain embodiments, the pharmaceutical composition comprises one species, strain, or subtype of bacteria that are engineered to comprise one or more of the genetic modifications described herein, e.g., selected from expression of at least one ammonium consuming circuit component, auxotrophy, kill-switch, exporter knock-out, etc. In alternate embodiments, the pharmaceutical composition comprises two or more species, strains, and/or subtypes of bacteria that are each engineered to comprise the genetic modifications described herein, e.g., selected from expression of at least one ammonia consuming circuit, auxotrophy, kill-switch, exporter knock-out, etc.

The pharmaceutical compositions of the invention described herein may be formulated in a conventional manner using one or more physiologically acceptable carriers comprising excipients and auxiliaries, which facilitate processing of the active ingredients into compositions for pharmaceutical use. Methods of formulating pharmaceutical compositions are known in the art (see, e.g., "Remington's Pharmaceutical Sciences," Mack Publishing Co., Easton, Pa.). In some embodiments, the pharmaceutical compositions are subjected to tabletting, lyophilizing, direct compression, conventional mixing, dissolving, granulating, levigating, emulsifying, encapsulating, entrapping, or spray drying to form tablets, granulates, nanoparticles, nanocapsules, microcapsules, microtablets, pellets, or powders, which may be enterically coated or uncoated. Appropriate formulation depends on the route of administration.

The genetically engineered microorganisms may be formulated into pharmaceutical compositions in any suitable dosage form (e.g., liquids, capsules, sachet, hard capsules, soft capsules, tablets, enteric coated tablets, suspension powders, granules, or matrix sustained release formations for oral administration) and for any suitable type of administration (e.g., oral, topical, injectable, intravenous, subcutaneous, immediate-release, pulsatile-release, delayed-release, or sustained release). Suitable dosage amounts for the genetically engineered bacteria may range from about $10^4$ to $10^{12}$ bacteria. The composition may be administered once or more daily, weekly, or monthly. The composition may be administered before, during, or following a meal. In one embodiment, the pharmaceutical composition is administered before the subject eats a meal. In one embodiment, the pharmaceutical composition is administered currently with a meal. In on embodiment, the pharmaceutical composition is administered after the subject eats a meal. Suitable pharmaceutical compositions and methods of administration are for example described in in co-owned US Patent Publication US20160333326 and International Patent Publication WO2017139697, the contents of each of which is herein incorporated by reference in its entirety. Methods of Screening, including Generation of Bacterial Strains with Enhance Ability to consume ammonia, are for example described in in co-owned US Patent Publication US20160333326 and International Patent Publication WO2017139697, the contents of each of which is herein incorporated by reference in its entirety.

Strains comprising Feedback Resistant N-acetylglutamate Synthetase, inducible constructs thereof, and sequences are described in US Patent Publication US20160333326 and International Patent Publication WO2017139697, the contents of which is herein incorporated by reference in its entirety. Mutations and or deletions in ArgR are described in in US Patent Publication US20160333326 and International Patent Publication WO2017139697, the contents of which is herein incorporated by reference in its entirety. Such constructs mutations, and deletions may be used in strains of the current disclosure.

Methods of Treatment

The disclosure provides genetically engineered bacteria that are capable of reducing excess ammonia and converting ammonia and/or nitrogen into alternate byproducts. In some embodiments, the genetically engineered bacteria are capable of converting ammonia into arginine, i.e., arginine is the alternate byproduct.

Another aspect of the invention provides methods of treating a disease or disorder associated with hyperammonemia. In some embodiments, the invention provides methods for reducing, ameliorating, or eliminating one or more symptom(s) associated with these diseases or disorders. In some embodiments, the disorder is a urea cycle disorder such as argininosuccinic aciduria, arginase deficiency, carbamoylphosphate synthetase deficiency, citrullinemia, N-acetylglutamate synthetase deficiency, and ornithine transcarbamylase deficiency. In alternate embodiments, the disorder is a liver disorder such as hepatic encephalopathy, acute liver failure, HCV, NASH, NAFLD, other liver disease or chronic liver failure; organic acid disorders; isovaleric aciduria; 3-methylcrotonylglycinuria; methylmalonic acidemia; propionic aciduria; fatty acid oxidation defects; carnitine cycle defects; carnitine deficiency; β-oxidation deficiency; lysinuric protein intolerance; pyrroline-5-carboxylate synthetase deficiency; pyruvate carboxylase deficiency; ornithine aminotransferase deficiency; carbonic anhydrase deficiency; hyperinsulinism-hyperammonemia syndrome; mitochondrial disorders; valproate therapy; asparaginase therapy; total parenteral nutrition; cystoscopy with glycine-containing solutions; post-lung/bone marrow transplantation; portosystemic shunting; urinary tract infections; ureter dilation; multiple myeloma; chemotherapy; infection; neurogenic bladder; or intestinal bacterial overgrowth. In some embodiments, the symptom(s) associated thereof include, but are not limited to, seizures, ataxia, stroke-like lesions, coma, psychosis, vision loss, acute encephalopathy, cerebral edema, as well as vomiting, respiratory alkalosis, and hypothermia.

The method may comprise preparing a pharmaceutical composition with at least one genetically engineered species, strain, or subtype of bacteria described herein, and administering the pharmaceutical composition to a subject in a therapeutically effective amount. In some embodiments, the genetically engineered bacteria of the invention are administered orally, e.g., in a liquid suspension. In some embodiments, the genetically engineered bacteria of the invention are lyophilized in a gel cap and administered orally. In some embodiments, the genetically engineered bacteria of the invention are administered via a feeding tube or gastric shunt. In some embodiments, the genetically engineered bacteria of the invention are administered rectally, e.g., by enema. In some embodiments, the genetically engineered bacteria of the invention are administered topically, intraintestinally, intrajejunally, intraduodenally, intraileally, and/or intracolically.

In certain embodiments, administering the pharmaceutical composition to the subject reduces ammonia concentrations in a subject, e.g., in the blood of the subject. In some embodiments, the methods of the present disclosure may reduce the ammonia concentration in a subject by at least about 10%, 20%, 25%, 30%, 40%, 50%, 60%, 70%, 75%, 80%, 85%, 90%, 95%, or more as compared to levels in an untreated or control subject. In some embodiments, reduction is measured by comparing the ammonia concentration in a subject before and after administration of the pharmaceutical composition. In some embodiments, the method of treating or ameliorating hyperammonemia allows one or more symptoms of the condition or disorder to improve by at least about 10%, 20%, 30%, 40%, 50%, 60%, 70%, 80%, 90%, 95%, or more.

Before, during, and after the administration of the pharmaceutical composition, ammonia concentrations in the subject may be measured in a biological sample, such as blood, serum, plasma, urine, fecal matter, peritoneal fluid, intestinal mucosal scrapings, a sample collected from a tissue, and/or a sample collected from the contents of one or more of the following: the stomach, duodenum, jejunum, ileum, cecum, colon, rectum, and anal canal. In some embodiments, the methods may include administration of the compositions of the invention to reduce ammonia concentrations in a subject to undetectable levels, or to less than about 1%, 2%, 5%, 10%, 20%, 25%, 30%, 40%, 50%, 60%, 70%, 75%, or 80% of the subject's ammonia concentrations prior to treatment.

In some embodiments, the methods may include administration of the compositions of the invention resulting in the production of arginine concentrations of at least about 1.2 to 1.4-fold, at least about 1.4 to 1.6-fold, at least about 1.6 to 1.8-fold, at least about 1.8 to 2-fold, or at least about 2 to 3-fold, at least about 3 to 4-fold, at least about 4 to 5-fold, at least about 5 to 6-fold, at least about 6 to 7-fold, or at least about 7 to 8-fold more arginine (e.g., in the blood or the liver) than the subject's arginine concentrations prior to treatment.

In any of these embodiments, the genetically engineered bacteria may produce at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70% to 80%, at least about 80% to 90%, or at least about 90% to 100% more arginine than bacteria that do not comprise gene sequences encoding ammonia consumption and/or arginine production circuitry, e.g., as described herein, of the same bacterial subtype under the same conditions. In yet another embodiment, the genetically engineered bacteria comprising gene sequences encoding ammonia consumption and/or arginine production circuitry, e.g., as described herein, may produce at least about 1.0 to 1.2-fold, at least about 1.2 to 1.4-fold, at least about 1.4 to 1.6-fold, at least about 1.6 to 1.8-fold, at least about 1.8 to 2-fold, or at least about two-fold more D-arginine than bacteria that do not comprise gene sequences encoding ammonia consumption and/or arginine production circuitry, e.g., as described herein, of the same bacterial subtype under the same conditions. In yet another embodiment, the genetically engineered bacteria comprising gene sequences encoding an ammonia consumption and/or arginine production circuitry, e.g., as described herein, produce at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, at least about 40 to 50-fold, at least about 50 to 100-fold, 100 to 500 hundred-fold, or at least about 500 to 1000-fold more arginine than bacteria that do not comprise gene sequences encoding an ammonia consumption and/or arginine production circuitry, e.g., as described herein, of the same bacterial subtype under the same conditions. In some embodiments, the conditions are in vitro conditions, e.g., during bacterial growth in culture. In some embodiments, the conditions are in vivo conditions, e.g., in the gut after administration of the bacteria to a subject (e.g., a human subject, mouse or non-human primate).

In any of these embodiments, at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70%, at least about 70% to 80%, at least about 80% to 90%, or at least about 90% to 100% more arginine is detected in the plasma of a subject (e.g., human, mouse or non-human primate) upon administration of the genetically engineered bacteria comprising gene sequences encoding an ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions. In yet another embodiment, at least about 1.0-1.2-fold, at least about 1.2-1.4-fold, at least about 1.4-1.6-fold, at least about 1.6-1.8-fold, at least about 1.8-2-fold, or at least about two-fold or more arginine is detected in the plasma upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions. In yet another embodiment, at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, or at least about 40 to 50-fold, at least about 50 to 100-fold, at least about 100 to 500-hundred-fold, or at least about 500 to 1000-fold more arginine is detected in the plasma upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions. In one embodiment, about 2-fold more plasma Arginine is detected in the plasma upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions, e.g., after 1, 2, 3, 4, 5, and/or 6 hours.

In some embodiments, the area under the curve is calculated after plasma arginine is measured over a timeframe. In some embodiments, the AUC is at least about 1 to 2-fold, at least about 2 to 3-fold, at least about 3 to 4-fold, or at least about 4 to 5-fold higher upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, of the same bacterial subtype under the same conditions. In one embodiment, the time frame is 6 hours. In one embodiment, the AUC is at least about 2 to 3 fold higher upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry of the same bacterial subtype under the same conditions.

In some embodiments, the plasma arginine levels are measured about 10, about 20, about 30, about 40, about 50 and/or about 60 minutes after administration of the genetically engineered bacteria. In some embodiments, the plasma arginine levels are measured about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, and/or about 24 hours after administration of the genetically engineered bacteria. In some embodiments, the plasma arginine levels are measured between about 1 and 2, about 2 and 3, about 3 and 4, about 4 and 5, about 5 and 6, and/or about 6 and 7 hours after administration of the genetically engineered bacteria. In some embodiments, the plasma arginine levels are measured about 1, about 2, about 3, about 4, about 5, about 6, and/or about 7 days, or after about 1, about 2, about 3, and/or about 4 weeks, or after about 1, about 2, about 3, about 4, about 5, about 6, about 7, about 8, about 9, about 10, about 11, about 12 months after administration of the genetically engineered bacteria. In some embodiments, the plasma arginine levels are measured after one or more years after administration of the genetically engineered bacteria. In one embodiment, the plasma arginine levels are measured after about 1, 2, 3, 4, 5, and 6 hours after administration of the genetically engineered bacteria.

In any of these embodiments, the genetically engineered bacteria can be administered once or multiple times daily or multiple times weekly, or multiple times monthly. In one example, the bacteria are administered once daily. In one example, the bacteria are administered twice daily. In one example, the bacteria are administered three times daily. In one example, the bacteria are administered daily over one week to a month. In one example, the bacteria are administered daily over one month to a year. In one example, the bacteria are administered daily for a time period greater than one year. In one example, the bacteria are administered once or more weekly over one week to a month. In one example, the bacteria are administered once or more weekly over one month to a year. In one example, the bacteria are administered once or more weekly for a time period greater than one year.

In any of these embodiments, at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70%, at least about 70% to 80%, at least about 80% to 90%, or at least about 90% to 100% more arginine is detected in the liver of a subject (e.g., human, mouse or non-human primate) upon administration of the genetically engineered bacteria comprising gene sequences encoding an ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions. In yet another embodiment, at least about 1.0-1.2-fold, at least about 1.2-1.4-fold, at least about 1.4-1.6-fold, at least about 1.6-1.8-fold, at least about 1.8-2-fold, or at least about two-fold or more arginine is detected in the liver upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions. In yet another embodiment, at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, or at least about 40 to 50-fold, at least about 50 to 100-fold, at least about 100 to 500-hundred-fold, or at least about 500 to 1000-fold more arginine is detected in the liver upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions. In one embodiment, about 2-fold more liver arginine is detected in the liver upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions, e.g., after 1, 2, 3, 4, 5, and/or 6 hours.

In some embodiments, the area under the curve is calculated after liver arginine is measured over a timeframe. In some embodiments, the AUC is at least about 1 to 2-fold, at least about 2 to 3-fold, at least about 3 to 4-fold, or at least about 4 to 5-fold higher upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, of the same bacterial subtype under the same conditions. In one embodiment, the time frame is 6 hours. In one embodiment, the AUC is at least about 2 to 3 fold higher upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry of the same bacterial subtype under the same conditions.

In some embodiments, the liver arginine levels are measured about 10, about 20, about 30, about 40, about 50 and/or about 60 minutes after administration of the genetically engineered bacteria. In some embodiments, the liver arginine levels are measured about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, and/or about 24 hours after administration of the genetically engineered bacteria. In some embodiments, the liver arginine levels are measured between about 1 and 2, about 2 and 3, about 3 and 4, about 4 and 5, about 5 and 6, and/or about 6 and 7 hours after administration of the genetically engineered bacteria. In some embodiments, the liver arginine levels are measured about 1, about 2, about 3, about 4, about 5, about 6, and/or about 7 days, or after about 1, about 2, about 3, and/or about 4 weeks, or after about 1, about 2, about 3, about 4, about 5, about 6, about 7, about 8, about 9, about 10, about 11, about 12 months after administration of the genetically engineered bacteria. In some embodiments, the liver arginine levels are measured after one or more years after administration of the genetically engineered bacteria. In one embodiment, the liver arginine levels are measured after about 1, 2, 3, 4, 5, and 6 hours after administration of the genetically engineered bacteria.

In any of these embodiments, the genetically engineered bacteria can be administered once or multiple times daily or multiple times weekly, or multiple times monthly. In one example, the bacteria are administered once daily. In one example, the bacteria are administered twice daily. In one example, the bacteria are administered three times daily. In one example, the bacteria are administered daily over one week to a month. In one example, the bacteria are administered daily over one month to a year. In one example, the bacteria are administered daily for a time period greater than one year. In one example, the bacteria are administered once or more weekly over one week to a month. In one example, the bacteria are administered once or more weekly over one month to a year. In one example, the bacteria are administered once or more weekly for a time period greater than one year.

In any of these embodiments, at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70%, at least about 70% to 80%, at least about 80% to 90%, or at least about 90% to 100% more arginine is detected in the urine of a subject (e.g., human, mouse or non-human primate) upon administration of the genetically engineered bacteria comprising gene sequences encoding ammonia consumption and/or arginine production circuitry than upon administration of bacteria that do not comprise gene sequences encoding ammonia consumption and/or arginine production circuitry of the same bacterial subtype under the same conditions. In yet another embodiment, at least about 1.0-1.2-fold, at least about 1.2-1.4-fold, at least about 1.4-1.6-fold, at least about 1.6-1.8-fold, at least about 1.8-2-fold, or at least about two-fold or more arginine is detected in the urine upon administration of the genetically engineered bacteria comprising gene sequences encoding ammonia consumption and/or arginine production circuitry than upon administration of bacteria that do not comprise gene sequences encoding ammonia consumption and/or arginine production circuitry of the same bacterial subtype under the same conditions. In yet another embodiment, at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, or at least about 40 to 50-fold, at least about 50 to 100-fold, at least about 100 to 500-hundred-fold, or at least about 500 to 1000-fold more arginine is detected in the urine upon administration of the genetically engineered bacteria comprising gene sequences encoding a racemase than upon administration of bacteria that do not comprise gene sequences encoding ammonia consumption and/or arginine production circuitry of the same bacterial subtype under the same conditions. In one embodiment, about 6 to 7-fold more urine Arginine is detected in the urine upon administration of the genetically engineered bacteria comprising gene sequences encoding ammonia consumption and/or arginine production circuitry than upon administration of bacteria that do not comprise gene sequences encoding an ammonia consumption and/or arginine production circuitry of the same bacterial subtype under the same conditions, e.g., after 6 hours.

In some embodiments, the area under the curve is calculated after urine arginine is measured over a timeframe. In some embodiments, the AUC is at least about 1 to 2-fold, at least about 2 to 3-fold, at least about 3 to 4-fold, or at least about 4 to 5-fold higher upon administration of the genetically engineered bacteria comprising gene sequences encoding a racemase than upon administration of bacteria that do not comprise gene sequences encoding an ammonia consumption and/or arginine production circuitry of the same bacterial subtype under the same conditions. In one embodiment, the time frame is 6 hours. In one embodiment, the AUC is at least about 2 to 3-fold higher upon administration of the genetically engineered bacteria comprising gene sequences encoding a racemase than upon administration of bacteria that do not comprise gene sequences encoding ammonia consumption and/or arginine production circuitry of the same bacterial subtype under the same conditions.

In some embodiments, the urine arginine levels are measured after about 10, about 20, about 30, about 40, about 50 and/or about 60 minutes. In some embodiments, the urine arginine levels are measured after about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, and/or about 24 hours. In some embodiments, the urine arginine levels are measured between about 1 and 2, about 2 and 3, about 3 and 4, about 4 and 5, about 5 and 6, and/or about 6 and 7 hours. In some embodiments, the urine D-arginine levels are measured after about 1, about 2, about 3, about 4, about 5, about 6, and/or about 7 days, or after about 1, about 2, about 3, and/or about 4 weeks, or after about 1, about 2, about 3, about 4, about 5, about 6, about 7, about 8, about 9, about 10, about 11, about 12 months after administration. In some embodiments, the urine arginine levels are measured after one or more years after administration. In one embodiment, the urine D-arginine levels are measured after about 1, 2, 3, 4, 5, and 6 hours.

In any of these embodiments, the genetically engineered bacteria may reduce inflammation in the gut, e.g., the colon, of a subject by at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70% to 80%, at least about 80% to 90%, or at least about 90% to 100% more as compared to bacteria that do not comprise gene sequences encoding ammonia consumption and/or arginine production circuitry, e.g., as described herein, of the same bacterial subtype under the same conditions.

In any of these embodiments, the genetically engineered bacteria may reduce inflammation in the gut, e.g., the colon, of a subject by at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70% to 80%, at least about 80% to 90%, or at least about 90% to 100% as compared to inflammation prior to administration of the bacteria (or as compared to a subject treated with a vehicle control).

In yet another embodiment, the genetically engineered bacteria comprising gene sequences encoding ammonia consumption and/or arginine production circuitry, e.g., as described herein, may reduce inflammation in the colon by at least about 1.0 to 1.2-fold, at least about 1.2 to 1.4-fold, at least about 1.4 to 1.6-fold, at least about 1.6 to 1.8-fold, at least about 1.8 to 2-fold, or at least about two-fold more than bacteria that do not comprise gene sequences encoding ammonia consumption and/or arginine production circuitry, e.g., as described herein, of the same bacterial subtype under the same conditions.

In yet another embodiment, the genetically engineered bacteria comprising gene sequences encoding ammonia consumption and/or arginine production circuitry, e.g., as described herein, may reduce inflammation in the colon by at least about 1.0 to 1.2-fold, at least about 1.2 to 1.4-fold, at least about 1.4 to 1.6-fold, at least about 1.6 to 1.8-fold, at least about 1.8 to 2-fold, or at least about two-fold as compared to inflammation prior to administration of the bacteria (or as compared to a subject treated with a vehicle control).

In yet another embodiment, the genetically engineered bacteria comprising gene sequences encoding an ammonia consumption and/or arginine production circuitry, e.g., as described herein, reduce inflammation in the gut, e.g., the colon, by at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, at least about 40 to 50-fold, at least about 50 to 100-fold, 100 to 500 hundred-fold, or at least about 500 to 1000-fold more than bacteria that do not comprise gene sequences encoding an ammonia consumption and/or arginine production circuitry, e.g., as described herein, of the same bacterial subtype under the same conditions. In some embodiments, the conditions are in vivo conditions, e.g., in the gut after administration of the bacteria to a subject (e.g., a human subject, mouse or non-human primate).

In yet another embodiment, the genetically engineered bacteria comprising gene sequences encoding an ammonia consumption and/or arginine production circuitry, e.g., as described herein, reduce inflammation in the gut, e.g., the colon, by at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, at least about 40 to 50-fold, at least about 50 to 100-fold, 100 to 500 hundred-fold, or at least about 500 to 1000-fold as compared to inflammation prior to administration of the bacteria (or as compared to a subject treated with a vehicle control).

In any of these embodiments, at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70%, at least about 70% to 80%, at least about 80% to 90%, or at least about 90% to 100% less inflammation is detected in the gut, e.g., the colon, of a subject (e.g., human, mouse or non-human primate) upon administration of the genetically engineered bacteria comprising gene sequences encoding an ammonia consumption and/or arginine production circuitry, e.g., as described herein, than upon administration of bacteria that do not comprise gene sequences encoding ammonia consumption and/or arginine production circuitry, of the same bacterial subtype under the same conditions.

In any of these embodiments, at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70%, at least about 70% to 80%, at least about 80% to 90%, or at least about 90% to 100% less inflammation is detected in the gut, e.g., the colon, of a subject (e.g., human, mouse or non-human primate) upon administration of the genetically engineered bacteria comprising gene sequences encoding an ammonia consumption and/or arginine production circuitry, e.g., as described herein, as compared to before the administration (or as compared to a subject treated with a vehicle control).

In yet another embodiment, at least about 1.0-1.2-fold, at least about 1.2-1.4-fold, at least about 1.4-1.6-fold, at least about 1.6-1.8-fold, at least about 1.8-2-fold, or at least about two-fold less inflammation is detected in the gut, e.g., the colon, upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions.

In yet another embodiment, at least about 1.0-1.2-fold, at least about 1.2-1.4-fold, at least about 1.4-1.6-fold, at least about 1.6-1.8-fold, at least about 1.8-2-fold, or at least about two-fold less inflammation is detected in the gut, e.g., the colon upon administration of the genetically engineered bacteria comprising gene sequences encoding ammonia consumption and/or arginine production circuitry, e.g., as described herein, as compared to before the administration (or as compared to a subject treated with a vehicle control).

In yet another embodiment, at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, or at least about 40 to 50-fold, at least about 50 to 100-fold, at least about 100 to 500-hundred-fold, or at least about 500 to 1000-fold less inflammation is detected in the gut, e.g., the colon, upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions.

In yet another embodiment, at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, or at least about 40 to 50-fold, at least about 50 to 100-fold, at least about 100 to 500-hundred-fold, or at least about 500 to 1000-fold less inflammation is detected in the gut, e.g., the colon, upon administration of the genetically engineered bacteria comprising gene sequences encoding ammonia consumption and/or arginine production circuitry, e.g., as described herein, as compared to before the administration (or as compared to a subject treated with a vehicle control).

In some embodiments, inflammation in the gut, e.g., the colon, is measured about 10, about 20, about 30, about 40, about 50 and/or about 60 minutes after administration of the genetically engineered bacteria. In some embodiments, the gut inflammation is measured about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, and/or about 24 hours after administration of the genetically engineered bacteria. In some embodiments, the gut inflammation levels are measured between about 1 and 2, about 2 and 3, about 3 and 4, about 4 and 5, about 5 and 6, and/or about 6 and 7 hours after administration of the genetically engineered bacteria. In some embodiments, the gut inflammation are measured about 1, about 2, about 3, about 4, about 5, about 6, and/or about 7 days, or after about 1, about 2, about 3, and/or about 4 weeks, or after about 1, about 2, about 3, about 4, about 5, about 6, about 7, about 8, about 9, about 10, about 11, about 12 months after administration of the genetically engineered bacteria. In some embodiments, the gut inflammation levels are measured after one or more years after administration of the genetically engineered bacteria. In one embodiment, the gut inflammation levels are measured after about 1, 2, 3, 4, 5, and 6 hours after administration of the genetically engineered bacteria.

Gut inflammation may be measured using various methods described in the art. In one non-limiting example, levels of various inflammatory markers or anti-inflammatory markers may be measured using techniques known in the art. Non-limiting examples of such markers include IL-6, IL-2, IL-1b, Occludin, TNF-alpha, and Claudin3.

In one non-limiting example levels of the pro-inflammatory cytokine IL-6 may be measured, e.g., by assessing mRNA levels, e.g., using qPCR methods known in the art.

Accordingly, in some of these embodiments, at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70%, at least about 70% to 80%, at least about 80% to 90%, or at least about 90% to 100% less IL-6, e.g., IL-6 mRNA, is detected in the gut, e.g., the colon tissue, of a subject (e.g., human, mouse or non-human primate) upon administration of the genetically engineered bacteria comprising gene sequences encoding an ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions.

In any of these embodiments, at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70%, at least about 70% to 80%, at least about 80% to 90%, or at least about 90% to 100% less IL-6, e.g., IL-6 mRNA, is detected in the gut, e.g., the colon tissue, of a subject (e.g., human, mouse or non-human primate) upon administration of the genetically engineered bacteria comprising gene sequences encoding an ammonia consumption and/or arginine production circuitry, e.g., as described herein, as compared to before the administration (or as compared to a subject treated with a vehicle control).

In yet another embodiment, at least about 1.0-1.2-fold, at least about 1.2-1.4-fold, at least about 1.4-1.6-fold, at least about 1.6-1.8-fold, at least about 1.8-2-fold, or at least about two-fold less IL-6, e.g., IL-6 mRNA, is detected in the gut, e.g., the colon tissue, upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions.

In yet another embodiment, at least about 1.0-1.2-fold, at least about 1.2-1.4-fold, at least about 1.4-1.6-fold, at least about 1.6-1.8-fold, at least about 1.8-2-fold, or at least about two-fold less IL-6, e.g., IL-6 mRNA, is detected in the gut, e.g., the colon tissue upon administration of the genetically engineered bacteria comprising gene sequences encoding ammonia consumption and/or arginine production circuitry, e.g., as described herein, as compared to before the administration. In one embodiment, at least about 1.4-1.6-fold less IL-6 mRNA, is detected in the colon tissue upon administration of the genetically engineered bacteria comprising gene sequences encoding ammonia consumption and/or arginine production circuitry, as compared to before the administration (or as compared to a subject treated with a vehicle control).

In yet another embodiment, at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, or at least about 40 to 50-fold, at least about 50 to 100-fold, at least about 100 to 500-hundred-fold, or at least about 500 to 1000-fold less IL-6, e.g., IL-6 mRNA, is detected in the gut, e.g., the colon tissue, upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions.

In yet another embodiment, at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, or at least about 40 to 50-fold, at least about 50 to 100-fold, at least about 100 to 500-hundred-fold, or at least about 500 to 1000-fold less IL-6, e.g., IL-6 mRNA, is detected in the gut, e.g., the colon tissue, upon administration of the genetically engineered bacteria comprising gene sequences encoding ammonia consumption and/or arginine production circuitry, e.g., as described herein, as compared to before the administration. In one embodiment, at least about 2.5 to 2.8-fold less IL-6 mRNA is detected in the colon tissue upon administration of the genetically engineered bacteria comprising gene sequences encoding ammonia consumption and/or arginine production circuitry, as compared to before the administration (or as compared to a subject treated with a vehicle control).

In some embodiments, IL-6, e.g., IL-6 mRNA, in the gut, e.g., the colon tissue, is measured about 10, about 20, about 30, about 40, about 50 and/or about 60 minutes after administration of the genetically engineered bacteria. In some embodiments, the gut IL-6, e.g., IL-6 mRNA, is measured about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, and/or about 24 hours after administration of the genetically engineered bacteria. In some embodiments, the gut IL-6, e.g., IL-6 mRNA, levels are measured between about 1 and 2, about 2 and 3, about 3 and 4, about 4 and 5, about 5 and 6, and/or about 6 and 7 hours after administration of the genetically engineered bacteria. In some embodiments, the gut IL-6, e.g., IL-6 mRNA, are measured about 1, about 2, about 3, about 4, about 5, about 6, and/or about 7 days, or after about 1, about 2, about 3, and/or about 4 weeks, or after about 1, about 2, about 3, about 4, about 5, about 6, about 7, about 8, about 9, about 10, about 11, about 12 months after administration of the genetically engineered bacteria. In some embodiments, the gut IL-6, e.g., IL-6 mRNA, levels are measured after one or more years after administration of the genetically engineered bacteria. In one embodiment, the gut inflammation levels are measured after about 1, 2, 3, 4, 5, and 6 hours after administration of the genetically engineered bacteria.

In one non-limiting example levels of the pro-inflammatory cytokine TNF-alpha may be measured, e.g., by assessing mRNA levels, e.g., using qPCR methods known in the art.

Accordingly, in some of these embodiments, at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70%, at least about 70% to 80%, at least about 80% to 90%, or at least about 90% to 100% less TNF-alpha, e.g., TNF-alpha mRNA, is detected in the gut, e.g., the colon tissue, of a subject (e.g., human, mouse or non-human primate) upon administration of the genetically engineered bacteria comprising gene sequences encoding an ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions.

In any of these embodiments, at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70%, at least about 70% to 80%, at least about 80% to 90%, or at least about 90% to 100% less TNF-alpha, e.g., TNF-alpha mRNA, is detected in the gut, e.g., the colon tissue, of a subject (e.g., human, mouse or non-human primate) upon administration of the genetically engineered bacteria comprising gene sequences encoding an ammonia consumption and/or arginine production circuitry, e.g., as described herein, as compared to before the administration (or as compared to a subject treated with a vehicle control).

In yet another embodiment, at least about 1.0-1.2-fold, at least about 1.2-1.4-fold, at least about 1.4-1.6-fold, at least about 1.6-1.8-fold, at least about 1.8-2-fold, or at least about two-fold less TNF-alpha, e.g., TNF-alpha mRNA, is detected in the gut, e.g., the colon tissue, upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions. In one embodiment, at least about 1.1-1.3-fold less TNF-alpha mRNA, is detected in the colon tissue, upon administration of the genetically engineered bacteria comprising gene sequences encoding ammonia consumption and/or arginine production circuitry than upon administration of bacteria that do not comprise gene sequences encoding ammonia consumption and/or arginine production circuitry of the same bacterial subtype under the same conditions.

In yet another embodiment, at least about 1.0-1.2-fold, at least about 1.2-1.4-fold, at least about 1.4-1.6-fold, at least about 1.6-1.8-fold, at least about 1.8-2-fold, or at least about two-fold less TNF-alpha, e.g., TNF-alpha mRNA, is detected in the gut, e.g., the colon tissue, upon administration of the genetically engineered bacteria comprising gene sequences encoding ammonia consumption and/or arginine production circuitry, e.g., as described herein, as compared to before the administration (or as compared to a subject treated with a vehicle control).

In yet another embodiment, at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, or at least about 40 to 50-fold, at least about 50 to 100-fold, at least about 100 to 500-hundred-fold, or at least about 500 to 1000-fold less TNF-alpha, e.g., TNF-alpha mRNA, is detected in the gut, e.g., the colon tissue, upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions.

In yet another embodiment, at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, or at least about 40 to 50-fold, at least about 50 to 100-fold, at least about 100 to 500-hundred-fold, or at least about 500 to 1000-fold less TNF-alpha, e.g., TNF-alpha mRNA, is detected in the gut, e.g., the colon tissue, upon administration of the genetically engineered bacteria comprising gene sequences encoding ammonia consumption and/or arginine production circuitry, e.g., as described herein, as compared to before the administration (or as compared to a subject treated with a vehicle control).

In some embodiments, TNF-alpha, e.g., TNF-alpha mRNA, in the gut, e.g., the colon tissue, is measured about 10, about 20, about 30, about 40, about 50 and/or about 60 minutes after administration of the genetically engineered bacteria. In some embodiments, the gut TNF-alpha, e.g., TNF-alpha mRNA, is measured about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, and/or about 24 hours after administration of the genetically engineered bacteria. In some embodiments, the gut TNF-alpha, e.g., TNF-alpha mRNA, levels are measured between about 1 and 2, about 2 and 3, about 3 and 4, about 4 and 5, about 5 and 6, and/or about 6 and 7 hours after administration of the genetically engineered bacteria. In some embodiments, the gut TNF-alpha, e.g., TNF-alpha mRNA, are measured about 1, about 2, about 3, about 4, about 5, about 6, and/or about 7 days, or after about 1, about 2, about 3, and/or about 4 weeks, or after about 1, about 2, about 3, about 4, about 5, about 6, about 7, about 8, about 9, about 10, about 11, about 12 months after administration of the genetically engineered bacteria. In some embodiments, the gut TNF-alpha, e.g., TNF-alpha mRNA, levels are measured after one or more years after administration of the genetically engineered bacteria. In one embodiment, the gut inflammation levels are measured after about 1, 2, 3, 4, 5, and 6 hours after administration of the genetically engineered bacteria.

In any of these embodiments, the genetically engineered bacteria may reduce inflammation in the liver of a subject by at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70% to 80%, at least about 80% to 90%, or at least about 90% to 100% more as compared to bacteria that do not comprise gene sequences encoding ammonia consumption and/or arginine production circuitry, e.g., as described herein, of the same bacterial subtype under the same conditions.

In any of these embodiments, the genetically engineered bacteria may reduce inflammation in the liver of a subject by at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70% to 80%, at least about 80% to 90%, or at least about 90% to 100% as compared to inflammation prior to administration of the bacteria (or as compared to a subject treated with a vehicle control).

In yet another embodiment, the genetically engineered bacteria comprising gene sequences encoding ammonia consumption and/or arginine production circuitry, e.g., as described herein, may reduce inflammation in the liver by at least about 1.0 to 1.2-fold, at least about 1.2 to 1.4-fold, at least about 1.4 to 1.6-fold, at least about 1.6 to 1.8-fold, at least about 1.8 to 2-fold, or at least about two-fold more than bacteria that do not comprise gene sequences encoding ammonia consumption and/or arginine production circuitry, e.g., as described herein, of the same bacterial subtype under the same conditions.

In yet another embodiment, the genetically engineered bacteria comprising gene sequences encoding ammonia consumption and/or arginine production circuitry, e.g., as described herein, may reduce inflammation in the liver by at least about 1.0 to 1.2-fold, at least about 1.2 to 1.4-fold, at least about 1.4 to 1.6-fold, at least about 1.6 to 1.8-fold, at least about 1.8 to 2-fold, or at least about two-fold as compared to inflammation prior to administration of the bacteria (or as compared to a subject treated with a vehicle control).

In yet another embodiment, the genetically engineered bacteria comprising gene sequences encoding an ammonia consumption and/or arginine production circuitry, e.g., as described herein, reduce inflammation in the liver by at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, at least about 40 to 50-fold, at least about 50 to 100-fold, 100 to 500 hundred-fold, or at least about 500 to 1000-fold more than bacteria that do not comprise gene sequences encoding an ammonia consumption and/or arginine production circuitry, e.g., as described herein, of the same bacterial subtype under the same conditions. In some embodiments, the conditions are in vivo conditions, e.g., in the liver after administration of the bacteria to a subject (e.g., a human subject, mouse or non-human primate).

In yet another embodiment, the genetically engineered bacteria comprising gene sequences encoding an ammonia consumption and/or arginine production circuitry, e.g., as described herein, reduce inflammation in the liver by at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, at least about 40 to 50-fold, at least about 50 to 100-fold, 100 to 500 hundred-fold, or at least about 500 to 1000-fold as compared to inflammation prior to administration of the bacteria (or as compared to a subject treated with a vehicle control).

In any of these embodiments, at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70%, at least about 70% to 80%, at least about 80% to 90%, or at least about 90% to 100% less inflammation is detected in the liver of a subject (e.g., human, mouse or non-human primate) upon administration of the genetically engineered bacteria comprising gene sequences encoding an ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions.

In any of these embodiments, at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70%, at least about 70% to 80%, at least about 80% to 90%, or at least about 90% to 100% less inflammation is detected in the liver of a subject (e.g., human, mouse or non-human primate) upon administration of the genetically engineered bacteria comprising gene sequences encoding an ammonia consumption and/or arginine production circuitry, e.g., as described herein, as compared to before the administration (or as compared to a subject treated with a vehicle control).

In yet another embodiment, at least about 1.0-1.2-fold, at least about 1.2-1.4-fold, at least about 1.4-1.6-fold, at least about 1.6-1.8-fold, at least about 1.8-2-fold, or at least about two-fold less inflammation is detected in the liver upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions.

In yet another embodiment, at least about 1.0-1.2-fold, at least about 1.2-1.4-fold, at least about 1.4-1.6-fold, at least about 1.6-1.8-fold, at least about 1.8-2-fold, or at least about two-fold less inflammation is detected in the liver upon administration of the genetically engineered bacteria comprising gene sequences encoding ammonia consumption and/or arginine production circuitry, e.g., as described herein, as compared to before the administration (or as compared to a subject treated with a vehicle control).

In yet another embodiment, at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, or at least about 40 to 50-fold, at least about 50 to 100-fold, at least about 100 to 500-hundred-fold, or at least about 500 to 1000-fold less inflammation is detected in the liver upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions.

In yet another embodiment, at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, or at least about 40 to 50-fold, at least about 50 to 100-fold, at least about 100 to 500-hundred-fold, or at least about 500 to 1000-fold less inflammation is detected in the liver upon administration of the genetically engineered bacteria comprising gene sequences encoding ammonia consumption and/or arginine production circuitry, e.g., as described herein, as compared to before the administration (or as compared to a subject treated with a vehicle control).

In some embodiments, inflammation in the liver is measured about 10, about 20, about 30, about 40, about 50 and/or about 60 minutes after administration of the genetically engineered bacteria. In some embodiments, the liver inflammation is measured about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, and/or about 24 hours after administration of the genetically engineered bacteria. In some embodiments, the liver inflammation levels are measured between about 1 and 2, about 2 and 3, about 3 and 4, about 4 and 5, about 5 and 6, and/or about 6 and 7 hours after administration of the genetically engineered bacteria. In some embodiments, the liver inflammation is measured about 1, about 2, about 3, about 4, about 5, about 6, and/or about 7 days, or after about 1, about 2, about 3, and/or about 4 weeks, or after about 1, about 2, about 3, about 4, about 5, about 6, about 7, about 8, about 9, about 10, about 11, about 12 months after administration of the genetically engineered bacteria. In some embodiments, the liver inflammation levels are measured after one or more years after administration of the genetically engineered bacteria. In one embodiment, the liver inflammation levels are measured after about 1, 2, 3, 4, 5, and 6 hours after administration of the genetically engineered bacteria.

Liver inflammation may be measured using various methods described in the art. In one non-limiting example, levels of various inflammatory markers or anti-inflammatory markers may be measured using techniques known in the art. Non-limiting examples of such markers include IL6, IL-1b, Bax, Bcl2, GSSG, GSH, TNF-alpha, MDA, Citrulline, Ornithine, Creatinine, and TGF-B1.

In one non-limiting example levels of the pro-inflammatory cytokine IL-6 may be measured, e.g., by assessing mRNA levels, e.g., using qPCR methods known in the art.

In any of these embodiments, at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70%, at least about 70% to 80%, at least about 80% to 90%, or at least about 90% to 100% less IL-6, e.g., IL-6 mRNA, is detected in the liver tissue of a subject (e.g., human, mouse or non-human primate) upon administration of the genetically engineered bacteria comprising gene sequences encoding an ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions.

In any of these embodiments, at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70%, at least about 70% to 80%, at least about 80% to 90%, or at least about 90% to 100% less IL-6, e.g., IL-6 mRNA, is detected in the liver tissue of a subject (e.g., human, mouse or non-human primate) upon administration of the genetically engineered bacteria comprising gene sequences encoding an ammonia consumption and/or arginine production circuitry, e.g., as described herein, as compared to before the administration (or as compared to a subject treated with a vehicle control).

In yet another embodiment, at least about 1.0-1.2-fold, at least about 1.2-1.4-fold, at least about 1.4-1.6-fold, at least about 1.6-1.8-fold, at least about 1.8-2-fold, or at least about two-fold less IL-6, e.g., IL-6 mRNA, is detected in the liver upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions. In one embodiment, at least about 1.7-2.0-fold less IL-6 mRNA, is detected in the liver upon administration of the genetically engineered bacteria comprising gene sequences encoding ammonia consumption and/or arginine production circuitry than upon administration of bacteria that do not comprise gene sequences encoding ammonia consumption and/or arginine production circuitry of the same bacterial subtype under the same conditions.

In yet another embodiment, at least about 1.0-1.2-fold, at least about 1.2-1.4-fold, at least about 1.4-1.6-fold, at least about 1.6-1.8-fold, at least about 1.8-2-fold, or at least about two-fold less IL-6, e.g., IL-6 mRNA, is detected in the liver upon administration of the genetically engineered bacteria comprising gene sequences encoding ammonia consumption and/or arginine production circuitry, e.g., as described herein, as compared to before the administration. In one embodiment, at least about 1.5-1.8-fold less IL-6 mRNA, is detected in the liver upon administration of the genetically engineered bacteria comprising gene sequences encoding ammonia consumption and/or arginine production circuitry, e.g., as described herein, as compared to before the administration (or as compared to a subject treated with a vehicle control).

In yet another embodiment, at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, or at least about 40 to 50-fold, at least about 50 to 100-fold, at least about 100 to 500-hundred-fold, or at least about 500 to 1000-fold less IL-6, e.g., IL-6 mRNA, is detected in the liver upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions.

In yet another embodiment, at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, or at least about 40 to 50-fold, at least about 50 to 100-fold, at least about 100 to 500-hundred-fold, or at least about 500 to 1000-fold less IL-6, e.g., IL-6 mRNA, is detected in the liver upon administration of the genetically engineered bacteria comprising gene sequences encoding ammonia consumption and/or arginine production circuitry, e.g., as described herein, as compared to before the administration (or as compared to a subject treated with a vehicle control).

In some embodiments, IL-6, e.g., IL-6 mRNA, in the liver is measured about 10, about 20, about 30, about 40, about 50 and/or about 60 minutes after administration of the genetically engineered bacteria. In some embodiments, the liver IL-6, e.g., IL-6 mRNA, is measured about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, and/or about 24 hours after administration of the genetically engineered bacteria. In some embodiments, the liver IL-6, e.g., IL-6 mRNA, levels are measured between about 1 and 2, about 2 and 3, about 3 and 4, about 4 and 5, about 5 and 6, and/or about 6 and 7 hours after administration of the genetically engineered bacteria. In some embodiments, the liver IL-6, e.g., IL-6 mRNA, is measured about 1, about 2, about 3, about 4, about 5, about 6, and/or about 7 days, or after about 1, about 2, about 3, and/or about 4 weeks, or after about 1, about 2, about 3, about 4, about 5, about 6, about 7, about 8, about 9, about 10, about 11, about 12 months after administration of the genetically engineered bacteria. In some embodiments, the liver IL-6, e.g., IL-6 mRNA, levels are measured after one or more years after administration of the genetically engineered bacteria. In one embodiment, the liver IL-6, e.g., IL-6 mRNA, levels are measured after about 1, 2, 3, 4, 5, and 6 hours after administration of the genetically engineered bacteria.

In any of these embodiments, at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70%, at least about 70% to 80%, at least about 80% to 90%, or at least about 90% to 100% less TNF-alpha, e.g., TNF-alpha mRNA, is detected in the liver tissue of a subject (e.g., human, mouse or non-human primate) upon administration of the genetically engineered bacteria comprising gene sequences encoding an ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions.

In any of these embodiments, at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70%, at least about 70% to 80%, at least about 80% to 90%, or at least about 90% to 100% less TNF-alpha, e.g., TNF-alpha mRNA, is detected in the liver tissue of a subject (e.g., human, mouse or non-human primate) upon administration of the genetically engineered bacteria comprising gene sequences encoding an ammonia consumption and/or arginine production circuitry, e.g., as described herein, as compared to before the administration (or as compared to a subject treated with a vehicle control).

In yet another embodiment, at least about 1.0-1.2-fold, at least about 1.2-1.4-fold, at least about 1.4-1.6-fold, at least about 1.6-1.8-fold, at least about 1.8-2-fold, or at least about two-fold less TNF-alpha, e.g., TNF-alpha mRNA, is detected in the liver upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions. In one embodiment, at least about 1.2-1.4-fold less TNF-alpha mRNA, is detected in the liver upon administration of the genetically engineered bacteria comprising gene sequences encoding ammonia consumption and/or arginine production circuitry than upon administration of bacteria that do not comprise gene sequences encoding ammonia consumption and/or arginine production circuitry of the same bacterial subtype under the same conditions.

In yet another embodiment, at least about 1.0-1.2-fold, at least about 1.2-1.4-fold, at least about 1.4-1.6-fold, at least about 1.6-1.8-fold, at least about 1.8-2-fold, or at least about two-fold less TNF-alpha, e.g., TNF-alpha mRNA, is detected in the liver upon administration of the genetically engineered bacteria comprising gene sequences encoding ammonia consumption and/or arginine production circuitry, e.g., as described herein, as compared to before the administration (or as compared to a subject treated with a vehicle control).

In yet another embodiment, at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, or at least about 40 to 50-fold, at least about 50 to 100-fold, at least about 100 to 500-hundred-fold, or at least about 500 to 1000-fold less TNF-alpha, e.g., TNF-alpha mRNA, is detected in the liver upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions.

In yet another embodiment, at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, or at least about 40 to 50-fold, at least about 50 to 100-fold, at least about 100 to 500-hundred-fold, or at least about 500 to 1000-fold less TNF-alpha, e.g., TNF-alpha mRNA, is detected in the liver upon administration of the genetically engineered bacteria comprising gene sequences encoding ammonia consumption and/or arginine production circuitry, e.g., as described herein, as compared to before the administration (or as compared to a subject treated with a vehicle control).

In some embodiments, TNF-alpha, e.g., TNF-alpha mRNA, in the liver is measured about 10, about 20, about 30, about 40, about 50 and/or about 60 minutes after administration of the genetically engineered bacteria. In some embodiments, the liver TNF-alpha, e.g., TNF-alpha mRNA, is measured about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, and/or about 24 hours after administration of the genetically engineered bacteria. In some embodiments, the liver TNF-alpha, e.g., TNF-alpha mRNA, levels are measured between about 1 and 2, about 2 and 3, about 3 and 4, about 4 and 5, about 5 and 6, and/or about 6 and 7 hours after administration of the genetically engineered bacteria. In some embodiments, the liver TNF-alpha, e.g., TNF-alpha mRNA, is measured about 1, about 2, about 3, about 4, about 5, about 6, and/or about 7 days, or after about 1, about 2, about 3, and/or about 4 weeks, or after about 1, about 2, about 3, about 4, about 5, about 6, about 7, about 8, about 9, about 10, about 11, about 12 months after administration of the genetically engineered bacteria. In some embodiments, the liver TNF-alpha, e.g., TNF-alpha mRNA, levels are measured after one or more years after administration of the genetically engineered bacteria. In one embodiment, the liver TNF-alpha, e.g., TNF-alpha mRNA, levels are measured after about 1, 2, 3, 4, 5, and 6 hours after administration of the genetically engineered bacteria.

In any of these embodiments, at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70%, at least about 70% to 80%, at least about 80% to 90%, or at least about 90% to 100% less TGF-beta, e.g., TGF-beta mRNA, is detected in the liver of a subject (e.g., human, mouse or non-human primate) upon administration of the genetically engineered bacteria comprising gene sequences encoding an ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions.

In any of these embodiments, at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70%, at least about 70% to 80%, at least about 80% to 90%, or at least about 90% to 100% less TGF-beta, e.g., TGF-beta mRNA, is detected in the liver of a subject (e.g., human, mouse or non-human primate) upon administration of the genetically engineered bacteria comprising gene sequences encoding an ammonia consumption and/or arginine production circuitry, e.g., as described herein, as compared to before the administration (or as compared to a subject treated with a vehicle control).

In yet another embodiment, at least about 1.0-1.2-fold, at least about 1.2-1.4-fold, at least about 1.4-1.6-fold, at least about 1.6-1.8-fold, at least about 1.8-2-fold, or at least about two-fold less TGF-beta, e.g., TGF-beta mRNA, is detected in the liver upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions. In one embodiment, at least about 1.1-1.3-fold less TGF-beta mRNA is detected in the liver upon administration of the genetically engineered bacteria comprising gene sequences encoding ammonia consumption and/or arginine production circuitry than upon administration of bacteria that do not comprise gene sequences encoding ammonia consumption and/or arginine production circuitry of the same bacterial subtype under the same conditions.

In yet another embodiment, at least about 1.0-1.2-fold, at least about 1.2-1.4-fold, at least about 1.4-1.6-fold, at least about 1.6-1.8-fold, at least about 1.8-2-fold, or at least about two-fold less TGF-beta, e.g., TGF-beta mRNA, is detected in the liver upon administration of the genetically engineered bacteria comprising gene sequences encoding ammonia consumption and/or arginine production circuitry, e.g., as described herein, as compared to before the administration. In one embodiment, at least about 1.2-1.4-fold less TGF-beta mRNA is detected in the liver upon administration of the genetically engineered bacteria comprising gene sequences encoding ammonia consumption and/or arginine production circuitry as compared to before the administration (or as compared to a subject treated with a vehicle control).

In yet another embodiment, at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, or at least about 40 to 50-fold, at least about 50 to 100-fold, at least about 100 to 500-hundred-fold, or at least about 500 to 1000-fold less TGF-beta, e.g., TGF-beta mRNA, is detected in the liver upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions.

In yet another embodiment, at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, or at least about 40 to 50-fold, at least about 50 to 100-fold, at least about 100 to 500-hundred-fold, or at least about 500 to 1000-fold less TGF-beta, e.g., TGF-beta mRNA, is detected in the liver upon administration of the genetically engineered bacteria comprising gene sequences encoding ammonia consumption and/or arginine production circuitry, e.g., as described herein, as compared to before the administration (or as compared to a subject treated with a vehicle control).

In some embodiments, TGF-beta, e.g., TGF-beta mRNA, in the liver is measured about 10, about 20, about 30, about 40, about 50 and/or about 60 minutes after administration of the genetically engineered bacteria. In some embodiments, the liver TGF-beta, e.g., TGF-beta mRNA, is measured about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, and/or about 24 hours after administration of the genetically engineered bacteria. In some embodiments, the liver TGF-beta, e.g., TGF-beta mRNA, levels are measured between about 1 and 2, about 2 and 3, about 3 and 4, about 4 and 5, about 5 and 6, and/or about 6 and 7 hours after administration of the genetically engineered bacteria. In some embodiments, the liver TGF-beta, e.g., TGF-beta mRNA, is measured about 1, about 2, about 3, about 4, about 5, about 6, and/or about 7 days, or after about 1, about 2, about 3, and/or about 4 weeks, or after about 1, about 2, about 3, about 4, about 5, about 6, about 7, about 8, about 9, about 10, about 11, about 12 months after administration of the genetically engineered bacteria. In some embodiments, the liver TGF-beta, e.g., TGF-beta mRNA, levels are measured after one or more years after administration of the genetically engineered bacteria. In one embodiment, the liver TGF-beta, e.g., TGF-beta mRNA, levels are measured after about 1, 2, 3, 4, 5, and 6 hours after administration of the genetically engineered bacteria.

In any of these embodiments, at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70%, at least about 70% to 80%, at least about 80% to 90%, or at least about 90% to 100% less alpha-SMA e.g., alpha-SMA mRNA, is detected in the liver of a subject (e.g., human, mouse or non-human primate) upon administration of the genetically engineered bacteria comprising gene sequences encoding an ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions.

In any of these embodiments, at least about 0% to 2%, at least about 2% to 4%, at least about 4% to 6%, at least about 6% to 8%, at least about 8% to 10%, at least about 10% to 12%, at least about 12% to 14%, at least about 14% to 16%, at least about 16% to 18%, at least about 18% to 20%, at least about 20% to 25%, at least about 25% to 30%, at least about 30% to 35%, at least about 35% to 40%, at least about 40% to 45%, at least about 45% to 50%, at least about 50% to 55%, at least about 55% to 60%, at least about 60% to 65%, at least about 65% to 70%, at least about 70% to 80%, at least about 80% to 90%, or at least about 90% to 100% less alpha-SMA e.g., alpha-SMA mRNA, is detected in the liver of a subject (e.g., human, mouse or non-human primate) upon administration of the genetically engineered bacteria comprising gene sequences encoding an ammonia consumption and/or arginine production circuitry, e.g., as described herein, as compared to before the administration (or as compared to a subject treated with a vehicle control).

In yet another embodiment, at least about 1.0-1.2-fold, at least about 1.2-1.4-fold, at least about 1.4-1.6-fold, at least about 1.6-1.8-fold, at least about 1.8-2-fold, or at least about two-fold less alpha-SMA e.g., alpha-SMA mRNA, is detected in the liver upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions.

In yet another embodiment, at least about 1.0-1.2-fold, at least about 1.2-1.4-fold, at least about 1.4-1.6-fold, at least about 1.6-1.8-fold, at least about 1.8-2-fold, or at least about two-fold less alpha-SMA e.g., alpha-SMA mRNA, is detected in the liver upon administration of the genetically engineered bacteria comprising gene sequences encoding ammonia consumption and/or arginine production circuitry, e.g., as described herein, as compared to before the administration. In one embodiment, at least about 1.9-2.1-fold less alpha-SMA mRNA is detected in the liver upon administration of the genetically engineered bacteria comprising gene sequences encoding ammonia consumption and/or arginine production circuitry as compared to before the administration (or as compared to a subject treated with a vehicle control).

In yet another embodiment, at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, or at least about 40 to 50-fold, at least about 50 to 100-fold, at least about 100 to 500-hundred-fold, or at least about 500 to 1000-fold less alpha-SMA e.g., alpha-SMA mRNA, is detected in the liver upon administration of the genetically engineered bacteria comprising gene sequences encoding ammonia consumption and/or arginine production circuitry, e.g., as described herein, than upon administration of bacteria that do not comprise gene sequences encoding ammonia consumption and/or arginine production circuitry, e.g., as described herein, of the same bacterial subtype under the same conditions.

In yet another embodiment, at least about 2 to 3-fold, at least about 3 to 4-fold, at least about 4 to 5-fold, at least about 5 to 6-fold, at least about 6 to 7-fold, at least about 7 to 8-fold, at least about 8 to 9-fold, at least about 9 to 10-fold, at least about 10 to 15-fold, at least about 15 to 20-fold, at least about 20 to 30-fold, at least about 30 to 40-fold, or at least about 40 to 50-fold, at least about 50 to 100-fold, at least about 100 to 500-hundred-fold, or at least about 500 to 1000-fold less alpha-SMA e.g., alpha-SMA mRNA, is detected in the liver upon administration of the genetically engineered bacteria comprising gene sequences encoding ammonia consumption and/or arginine production circuitry, e.g., as described herein, as compared to before the administration (or as compared to a subject treated with a vehicle control).

In some embodiments, alpha-SMA e.g., alpha-SMA mRNA, in the liver is measured about 10, about 20, about 30, about 40, about 50 and/or about 60 minutes after administration of the genetically engineered bacteria. In some embodiments, the liver alpha-SMA e.g., alpha-SMA mRNA, is measured about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, and/or about 24 hours after administration of the genetically engineered bacteria. In some embodiments, the liver alpha-SMA e.g., alpha-SMA mRNA, levels are measured between about 1 and 2, about 2 and 3, about 3 and 4, about 4 and 5, about 5 and 6, and/or about 6 and 7 hours after administration of the genetically engineered bacteria. In some embodiments, the liver alpha-SMA e.g., alpha-SMA mRNA, is measured about 1, about 2, about 3, about 4, about 5, about 6, and/or about 7 days, or after about 1, about 2, about 3, and/or about 4 weeks, or after about 1, about 2, about 3, about 4, about 5, about 6, about 7, about 8, about 9, about 10, about 11, about 12 months after administration of the genetically engineered bacteria. In some embodiments, the liver alpha-SMA e.g., alpha-SMA mRNA, levels are measured after one or more years after administration of the genetically engineered bacteria. In one embodiment, the liver alpha-SMA e.g., alpha-SMA mRNA, levels are measured after about 1, 2, 3, 4, 5, and 6 hours after administration of the genetically engineered bacteria.

In some embodiments, the genetically engineered bacteria comprising gene sequences encoding ammonia consumption and/or arginine production circuitry are administered once. In some embodiments, the genetically engineered bacteria comprising gene sequences encoding ammonia consumption and/or arginine production circuitry are administered more than once (e.g., more than once daily, more than once weekly, more than once monthly). In some embodiments, the genetically engineered bacteria comprising gene sequences encoding ammonia consumption and/or arginine production circuitry are administered more than once (e.g., twice daily or more, or 2, 3, 4, 5, 6, 7, 8, 9, 10, 11, 12, 13, 14 times or more weekly. In some embodiments, the genetically engineered bacteria comprising gene sequences encoding ammonia consumption and/or arginine production circuitry are administered once, twice or more daily for one or more months. In some embodiments, the genetically engineered bacteria comprising gene sequences encoding ammonia consumption and/or arginine production circuitry are administered once, twice or more daily for one or more years.

In certain embodiments, the genetically engineered bacteria comprising circuitry for the expression of arginine and optionally the mutant arginine regulon is *E. coli* Nissle. The genetically engineered bacteria may be destroyed, e.g., by defense factors in the gut or blood serum (Sonnenborn et al., 2009), or by activation of a kill switch, several hours or days after administration. Thus, the pharmaceutical composition comprising the mutant arginine regulon may be re-administered at a therapeutically effective dose and frequency. In alternate embodiments, the genetically engineered bacteria are not destroyed within hours or days after administration and may propagate and colonize the gut.

The pharmaceutical composition may be administered alone or in combination with one or more additional therapeutic agents, including but not limited to, sodium phenylbutyrate, sodium benzoate, and glycerol phenylbutyrate. An important consideration in the selection of the one or more additional therapeutic agents is that the agent(s) should be compatible with the genetically engineered bacteria of the invention, e.g., the agent(s) must not kill the bacteria.

In one embodiment, the genetically engineered bacteria are administered for prevention, treatment or management of HE. In some embodiments, the genetically engineered bacteria are administered in combination with another therapeutic approach to prevent HE reoccurrence. In one embodiment, the genetically engineered bacteria are administered in combination with branched-chain amino acid supplementation. In one embodiment, the genetically engineered bacteria are administered in combination with acetyl-1-carnitine and/or sodium benzoate and/or zinc and/or acarbose and/or ornithine aspartate. In one embodiment, the genetically engineered bacteria are administered in combination with non-absorbable disaccharides, which are commonly applied to both treat and prevent HE in patients. In one embodiment, the genetically engineered bacteria are administered in combination with lactulose and/or lactitol.

In one embodiment, the genetically engineered bacteria are administered in combination with one or more antibiotics, for example for the treatment of HE. Examples of such antibiotics include, but are not limited to, non-absorbable antibiotics, such as aminoglicosides, e.g., neomycin and/or paramomycin. In one embodiment, the antibiotic is rifamycin. In one embodiment, the antibiotic is a rifamycin derivative, e.g., a synthetic derivative, including but not limited to, rifaximin.

Rifaximin has been shown to significantly reduce the risk of an episode of hepatic encephalopathy, as compared with placebo, over a 6-month period (Bass et a., Rifaximin Treatment in Hepatic Encephalopathy; N Engl J Med 2010; 362:1071-1081). Rifaximin is a semi-synthetic derivative of rifampin and acts by binding to the beta-subunit of bacterial DNA-dependent RNA polymerase, and thereby blocking transcription. As a result, bacterial protein synthesis and growth is inhibited.

Rifaximin has been shown to be active against *E. coli* both in vitro and in clinical studies. It therefore is understood that, for a combination treatment with rifaximin to be effective, the genetically engineered bacteria must further comprise a rifaximin resistance.

Resistance to rifaximin is caused primarily by mutations in the rpoB gene. This changes the binding site on DNA dependent RNA polymerase and decreases rifaximin binding affinity, thereby reducing efficacy. In one embodiment, the rifaximin resistance is a mutation in the rpoB gene. Non-limiting examples of such mutations are described in e.g., Rodriguez-Verdugo, Evolution of *Escherichia coli* rifampicin resistance in an antibiotic-free environment during thermal stress. BMC Evol Biol. 2013 Feb. 22; 13:50. Of note, mutations in the same three codons of the rpoB consensus sequence occur repeatedly in unrelated rifaximin-resistant clinical isolates of several different bacterial species (as reviewed in Goldstein, Resistance to rifampicin: a review; The Journal of Antibiotics (2014), 1-6, the contents of which is herein incorporated by reference in its entirety. In some embodiments, the genetically engineered bacteria comprise a known rifaximin resistance mutation, e.g., in the rpoB gene. In other embodiments, a screen can be employed, exposing the genetically engineered bacteria to increasing amounts of rifaximin, to identify a useful mutation which confers rifaximin resistance.

The methods disclosed herein may comprise administration of a composition alone or in combination with one or more additional therapies, e.g., pioglitazone, which has been shown to improve steatosis, inflammation, and fibrosis; vitamin E, which has been shown to improve steatohepatitis; or orlistat, which has been shown to improve alanine transaminase and steatosis (see, for example, Dyson et al., Frontline Gastroenterology, 5(4):277-286, 2014). The pharmaceutical composition may be administered alone or in combination with one or more additional therapeutic agents. In another embodiment, the methods disclosed herein may comprise a caloric restricted diet (600 calories less than the daily requirement), exercise, or bariatric surgery.

In some embodiments, the pharmaceutical composition is administered with food. In alternate embodiments, the pharmaceutical composition is administered before or after eating food. The pharmaceutical composition may be administered in combination with one or more dietary modifications, e.g., low-protein diet and amino acid supplementation. The dosage of the pharmaceutical composition and the frequency of administration may be selected based on the severity of the symptoms and the progression of the disorder. The appropriate therapeutically effective dose and/or frequency of administration can be selected by a treating clinician.

Treatment In Vivo

The genetically engineered bacteria of the invention may be evaluated in vivo, e.g., in an animal model. Any suitable animal model of a disease or condition associated with hyperammonemia may be used (see, e.g., Deignan et al., 2008; Nicaise et al., 2008), for example, a mouse model of acute liver failure and hyperammonemia. This acute liver failure and hyperammonemia may be induced by treatment with thiol acetamide (TAA) (Basile et al., 1990; Nicaise et al., 2008). Alternatively, liver damage may be modeled using physical bile duct ligation (Rivera-Mancia et al., 2012). Hyperammonemia may also be induced by oral supplementation with ammonium acetate and/or magnesium chloride (Azorin et al., 1989; Rivera-Mancia et al., 2012).

Additionally, CCl4 is often used to induce hepaticfibrosis and cirrhosis in animals (Nhung et al., Establishment of a standardized mouse model of hepatic fibrosis for biomedical research; Biomedical Research and Therapy 2014, 1(2):43-49).

The genetically engineered bacteria of the invention may be administered to the animal, e.g., by oral gavage, and treatment efficacy determined, e.g., by measuring ammonia in blood samples and/or arginine, citrulline, or other byproducts in fecal samples.

Full citations for the references cited throughout the specification include:

1. Alifano et al. Histidine biosynthetic pathway and genes: structure, regulation, and evolution. Microbiol Rev. 1996 March; 60(1):44-69. PMID: 8852895.
2. Altenhoefer et al. The probiotic *Escherichia coli* strain Nissle 1917 interferes with invasion of human intestinal epithelial cells by different enteroinvasive bacterial pathogens. FEMS Immunol Med Microbiol. 2004 Apr. 9; 40(3):223-229. PMID: 15039098.
3. Andersen et al. Uracil uptake in *Escherichia coli* K-12: isolation of uraA mutants and cloning of the gene. J Bacteriol. 1995 April; 177(8):2008-2013. PMID: 7721693.
4. Arthur et al. Intestinal inflammation targets cancer-inducing activity of the microbiota. Science. 2012 Oct. 5; 338(6103):120-123. PMID: 22903521.
5. Aoyagi et al. Gastrointestinal urease in man. Activity of mucosal urease. Gut. 1966 December; 7(6):631-635. PMID: 5957514.
6. Arai et al. Expression of the nir and nor genes for denitrification of *Pseudomonas aeruginosa* requires a novel CRP/FNR-related transcriptional regulator, DNR, in addition to ANR. FEBS Lett. 1995 Aug. 28; 371(1):73-76. PMID: 7664887.
7. Aschner et al. Manganese uptake and distribution in the central nervous system (CNS). Neurotoxicology. 1999 April-June; 20(2-3):173-180. PMID: 10385881.
8. Azorin et al. A simple animal model of hyperammonemia. Hepatology. 1989 September; 10(3):311-314. PMID: 2759549.
9. Bansky et al. Reversal of hepatic coma by benzodiazepene antagonists (Ro15-1788). Lancet. 1985; 1:1324-1325.
10. Basile et al. Brain concentrations of benzodiazepines are elevated in an animal model of hepatic encephalopathy. Proc Natl Acad Sci USA. 1990 July; 87(14):5263-5267. PMID: 1973539.
11. Bearden S W, Perry R D. The Yfe system of *Yersinia pestis* transports iron and manganese and is required for full virulence of plague. Mol Microbiol. 1999 April; 32(2):403-414. PMID: 10231495.
12. Berk D P, Chalmers T. Deafness complicating antibiotic therapy of hepatic encephalopathy. Ann Intern Med. 1970 September; 73(3):393-396. PMID: 5455989.
13. Blanc et al. Lactitol or lactulose in the treatment of chronic hepatic encephalopathy: results of a meta-analysis. Hepatology. 1992 February; 15(2):222-228. PMID: 1531204.
14. Caldara et al. The arginine regulon of *Escherichia coli*: whole-system transcriptome analysis discovers new genes and provides an integrated view of arginine regulation. Microbiology. 2006 November; 152(Pt 11):3343-3354. PMID: 17074904.
15. Caldara et al. Arginine biosynthesis in *Escherichia coli*: experimental perturbation and mathematical modeling. J Biol Chem. 2008 Mar. 7; 283(10):6347-6358. PMID: 18165237.
16. Caldovic et al. N-acetylglutamate synthase: structure, function and defects. Mol Genet Metab. 2010; 100 Suppl 1:S13-S19. Review. PMID: 20303810.
17. Callura et al. Tracking, tuning, and terminating microbial physiology using synthetic riboregulators. Proc Natl Acad Sci USA. 2010 Sep. 7; 107(36):15898-15903. PMID: 20713708.
18. Cash et al. Current concepts in the assessment and treatment of hepatic encephalopathy. Q J M. 2010 January; 103(1):9-16. PMID: 19903725.
19. Castiglione et al. The transcription factor DNR from *Pseudomonas aeruginosa* specifically requires nitric oxide and haem for the activation of a target promoter in *Escherichia coli*. Microbiology. 2009 September; 155(Pt 9):2838-2844. PMID: 19477902.
20. Cellier et al. Resistance to intracellular infections: comparative genomic analysis of Nramp. Trends Genet. 1996 June; 12(6):201-204. PMID: 8928221.
21. Charlier et al. Arginine regulon of *Escherichia coli* K-12. A study of repressor-operator interactions and of in vitro binding affinities versus in vivo repression. J Mol Biol. 1992 Jul. 20; 226(2):367-386. PMID: 1640456.
22. Chiang et al. Dysregulation of C/EBPalpha by mutant Huntingtin causes the urea cycle deficiency in Huntington's disease. Hum Mol Genet. 2007 Mar. 1; 16(5):483-498. PMID: 17213233.
23. Collinson et al. Channel crossing: how are proteins shipped across the bacterial plasma membrane? Philos Trans R Soc Lond B Biol Sci. 2015; 370:20150025. PMID: 26370937.
24. Cordoba J, Mínguez B. Hepatic Encephalopathy. Semin Liver Dis. 2008; 28(1):70-80. PMID: 18293278.
25. Costa et al. Secretion systems in Gram-negative bacteria: structural and mechanistic insights. Nat Rev Microbiol. 2015; 13(6):343-359. PMID: 25978706.
26. Crabeel et al. Characterization of the *Saccharomyces cerevisiae* ARG7 gene encoding ornithine acetyltransferase, an enzyme also endowed with acetylglutamate synthase activity. Eur J Biochem. 1997 Dec. 1; 250(2):232-241. PMID: 9428669.
27. Cuevas-Ramos et al. *Escherichia coli* induces DNA damage in vivo and triggers genomic instability in mammalian cells. Proc Natl Acad Sci USA. 2010 Jun. 22; 107(25):11537-42. PMID: 20534522.
28. Cunin et al. Molecular basis for modulated regulation of gene expression in the arginine regulon of *Escherichia coli* K-12. Nucleic Acids Res. 1983 Aug. 11; 11(15):5007-5019. PMID: 6348703.
29. Cunin et al. Biosynthesis and metabolism of arginine in bacteria. Microbiol Rev. 1986 September; 50(3):314-52. Review. Erratum in: Microbiol Rev. 1987 March; 51(1): 178. PMID: 3534538.
30. Danino et al. Programmable probiotics for detection of cancer in urine. Sci Transl Med. 2015 May 27; 7(289): 289ra84. PMID: 26019220.
31. Deignan et al. Contrasting features of urea cycle disorders in human patients. Mol Genet Metab. 2008 January; 93(1):7-14. PMID: 17933574.

32. Deutscher. The mechanisms of carbon catabolite repression in bacteria. Curr Opin Microbiol. 2008 April; 11(2): 87-93. PMID: 18359269.
33. Diaz et al Ammonia control and neurocognitive outcome among urea cycle disorder patients treated with glycerol phenylbutyrate. Hepatology. 2013 June; 57(6):2171-9. PMID: 22961727.
34. Dinleyici et al. *Saccharomyces boulardii* CNCM 1-745 in different clinical conditions. Expert Opin Biol Ther. 2014 November; 14(11):1593-609. PMID: 24995675.
35. Doolittle. A new allele of the sparse fur gene in the mouse. J Hered. 1974 May-June; 65(3):194-5. PMID: 4603259.
36. Eckhardt et al. Isolation and characterization of mutants with a feedback resistant N-acetylglutamate synthase in *Escherichia coli* K 12. Mol Gen Genet. 1975 Jun. 19; 138(3):225-32. PMID: 1102931.
37. Eiglmeier et al. Molecular genetic analysis of FNR-dependent promoters. Mol Microbiol. 1989 July; 3(7): 869-78. PMID: 2677602.
38. Fraga et al. (2008). Real-Time PCR. *Current Protocols Essential Laboratory Techniques* (10.3.1-10.3.33). John Wiley & Sons, Inc.
39. Galimand et al. Positive FNR-like control of anaerobic arginine degradation and nitrate respiration in *Pseudomonas aeruginosa*. J Bacteriol. 1991 March; 173(5):1598-606. PMID: 1900277.
40. Gamper et al. Anaerobic regulation of transcription initiation in the arcDABC operon of *Pseudomonas aeruginosa*. J Bacteriol. 1991 August; 173(15):4742-50. PMID: 1906871.
41. Gardner et al. Construction of a genetic toggle switch in *Escherichia coli*. Nature. 2000; 403:339-42. PMID: 10659857.
42. Gorke B et al. Carbon catabolite repression in bacteria—many ways to make the most out of nutrients. Nat Rev Microbiol. 2008 August; 6(8):613-24. PMID: 18628769.
43. Haberle et al. Suggested guidelines for the diagnosis and management of urea cycle disorders. Orphanet J Rare Dis. 2012 May 29; 7:32. Review. PMID: 22642880.
44. Haberle J. Clinical and biochemical aspects of primary and secondary hyperammonemic disorders. Arch Biochem Biophys. 2013 Aug. 15; 536(2):101-8. Review. PMID: 23628343.
45. Hasegawa et al. Activation of a consensus FNR-dependent promoter by DNR of *Pseudomonas aeruginosa* in response to nitrite. FEMS Microbiol Lett. 1998 Sep. 15; 166(2):213-7. PMID: 9770276.
46. Hodges et al. The spfash mouse: a missense mutation in the ornithine transcarbamylase gene also causes aberrant mRNA splicing. Proc Natl Acad Sci USA. 1989 June; 86(11):4142-6. PMID: 2471197.
47. Hoeren et al. Sequence and expression of the gene encoding the respiratory nitrous-oxide reductase from *Paracoccus denitrificans*. Eur J Biochem. 1993 Nov. 15; 218(1):49-57. PMID: 8243476.
48. Hoffmann et al. Defects in amino acid catabolism and the urea cycle. Handb Clin Neurol. 2013; 113:1755-73. Review. PMID: 23622399.
49. Hosseini et al. Proprionate as a health-promoting microbial metabolite in the human gut. Nutr Rev. 2011 May; 69(5):245-58. PMID: 21521227.
50. Isabella et al. Deep sequencing-based analysis of the anaerobic stimulon in *Neisseria gonorrhoeae*. BMC Genomics. 2011 Jan. 20; 12:51. PMID: 21251255.
51. Konieczna et al. Bacterial urease and its role in long-lasting human diseases. Curr Protein Pept Sci. 2012 December; 13(8):789-806. Review. PMID: 23305365.
52. Lazier et al. Hyperammonemic encephalopathy in an adenocarcinoma patient managed with carglumic acid. Curr Oncol. 2014 October; 21(5):e736-9. PMID: 25302046.
53. Leonard (2006). Disorders of the urea cycle and related enzymes. *Inborn Metabolic Diseases*, 4$^{th}$ ed (pp. 263-272). Springer Medizin Verlag Heidelberg.
54. Lim et al. Nucleotide sequence of the argR gene of *Escherichia coli* K-12 and isolation of its product, the arginine repressor. Proc Natl Acad Sci USA. 1987 October; 84(19):6697-701. PMID: 3116542.
55. Makarova et al. Conservation of the binding site for the arginine repressor in all bacterial lineages. Genome Biol. 2001; 2(4). PMID: 11305941.
56. Maas et al. Studies on the mechanism of repression of arginine biosynthesis in *Escherichia coli*. Dominance of repressibility in diploids. J Mol Biol. 1964 March; 8:365-70. PMID: 14168690.
57. Maas. The arginine repressor of *Escherichia coli*. Microbiol Rev. 1994 December; 58(4):631-40. PMID: 7854250.
58. Meng et al. Nucleotide sequence of the *Escherichia coli* cad operon: a system for neutralization of low extracellular pH. J Bacteriol. 1992 April; 174(8):2659-69. PMID: 1556085.
59. Moore et al. Regulation of FNR dimerization by subunit charge repulsion. J Biol Chem. 2006 Nov. 3; 281(44): 33268-75. PMID: 16959764.
60. Mountain et al. Cloning of a *Bacillus subtilis* restriction fragment complementing auxotrophic mutants of eight *Escherichia coli* genes of arginine biosynthesis. Mol Gen Genet. 1984; 197(1):82-9. PMID: 6096675.
61. Nagamani et al. Optimizing therapy for argininosuccinic aciduria. Mol Genet Metab. 2012 September; 107(1-2): 10-4. Review. PMID: 22841516.
62. Nicaise et al. Control of acute, chronic, and constitutive hyperammonemia by wild-type and genetically engineered *Lactobacillus plantarum* in rodents. Hepatology. 2008 October; 48(4):1184-92. PMID: 18697211.
63. Nicoloff et al. Two arginine repressors regulate arginine biosynthesis in *Lactobacillus plantarum*. J Bacteriol. 2004 September; 186(18):6059-69. PMID: 15342575.
64. Nougayrede et al. *Escherichia coli* induces DNA double-strand breaks in eukaryotic cells. Science. 2006 Aug. 11; 313(5788):848-51. PMID: 16902142.
65. Olier et al. Genotoxicity of *Escherichia coli* Nissle 1917 strain cannot be dissociated from its probiotic activity. Gut Microbes. 2012 November-December; 3(6):501-9. PMID: 22895085.
66. Pham et al. Multiple myeloma-induced hyperammonemic encephalopathy: an entity associated with high in-patient mortality. Leuk Res. 2013 October; 37(10):1229-32. Review. PMID: 23932549.
67. Raj agopal et al. Use of inducible feedback-resistant N-acetylglutamate synthetase (argA) genes for enhanced arginine biosynthesis by genetically engineered *Escherichia coli* K-12 strains. Appl Environ Microbiol. 1998 May; 64(5):1805-11. PMID: 9572954.
68. Ray et al. The effects of mutation of the anr gene on the aerobic respiratory chain of *Pseudomonas aeruginosa*. FEMS Microbiol Lett. 1997 Nov. 15; 156(2):227-32. PMID: 9513270.
69. Reister et al. Complete genome sequence of the Gram-negative probiotic *Escherichia coli* strain Nissle 1917. J Biotechnol. 2014 Oct. 10; 187:106-7. PMID: 25093936.

70. Rembacken et al. Non-pathogenic *Escherichia coli* versus mesalazine for the treatment of ulcerative colitis: a randomised trial. Lancet. 1999 Aug. 21; 354(9179):635-9. PMID: 10466665.
71. Remington's Pharmaceutical Sciences, 22$^{nd}$ ed. Mack Publishing Co.
72. Salmon et al. Global gene expression profiling in *Escherichia coli* K12. The effects of oxygen availability and FNR. J Biol Chem. 2003 Aug. 8; 278(32):29837-55. PMID: 12754220.
73. Sat et al. The *Escherichia coli* mazEF suicide module mediates thymineless death. J Bacteriol. 2003 March; 185(6):1803-7. PMID: 12618443.
74. Sawers. Identification and molecular characterization of a transcriptional regulator from *Pseudomonas aeruginosa* PAO1 exhibiting structural and functional similarity to the FNR protein of *Escherichia coli*. Mol Microbiol. 1991 June; 5(6):1469-81. PMID: 1787797.
75. Schneider et al. Arginine catabolism and the arginine succinyltransferase pathway in *Escherichia coli*. J Bacteriol. 1998 August; 180(16): 4278-86. PMID: 9696779.
76. Schultz. Clinical use of *E. coli* Nissle 1917 in inflammatory bowel disease. Inflamm Bowel Dis. 2008 July; 14(7):1012-8. Review. PMID: 18240278.
77. Sonnenborn et al. The non-pathogenic *Escherichia coli* strain Nissle 1917—features of a versatile probiotic. Microbial Ecology in Health and Disease. 2009; 21:122-58.
78. Suiter et al. Fitness consequences of a regulatory polymorphism in a seasonal environment. Proc Natl Acad Sci USA. 2003 Oct. 28; 100(22):12782-6. PMID: 14555766.
79. Summerskill. On the origin and transfer of ammonia in the human gastrointestinal tract. Medicine (Baltimore). 1966 November; 45(6):491-6. PMID: 5925900.
80. Szwajkajzer et al. Quantitative analysis of DNA binding by the *Escherichia coli* arginine repressor. J Mol Biol. 2001 Oct. 5; 312(5):949-62. PMID: 11580241.
81. Tian et al. Binding of the arginine repressor of *Escherichia coli* K12 to its operator sites. J Mol Biol. 1992 Jul. 20; 226(2):387-97. PMID: 1640457.
82. Tian et al. Explanation for different types of regulation of arginine biosynthesis in *Escherichia coli* B and *Escherichia coli* K12 caused by a difference between their arginine repressors. J Mol Biol. 1994 Jan. 7; 235(1):221-30. PMID: 8289243.
83. Tones-Vega et al. Delivery of glutamine synthetase gene by baculovirus vectors: a proof of concept for the treatment of acute hyperammonemia. Gene Ther. 2014 Oct. 23; 22(1):58-64. PMID: 25338921.
84. Trunk et al. Anaerobic adaptation in *Pseudomonas aeruginosa*: definition of the Anr and Dnr regulons. Environ Microbiol. 2010 June; 12(6):1719-33. PMID: 20553552.
85. Tuchman et al. Enhanced production of arginine and urea by genetically engineered *Escherichia coli* K-12 strains. Appl Environ Microbiol. 1997 January; 63(1):33-8. PMID: 8979336.
86. Ukena et al. Probiotic *Escherichia coli* Nissle 1917 inhibits leaky gut by enhancing mucosal integrity. PLoS One. 2007 Dec. 12; 2(12):e1308. PMID: 18074031.
87. Unden et al. Alternative respiratory pathways of *Escherichia coli*: energetics and transcriptional regulation in response to electron acceptors. Biochim Biophys Acta. 1997 Jul. 4; 1320(3):217-34. Review. PMID: 9230919.
88. Vander Wauven et al. *Pseudomonas aeruginosa* mutants affected in anaerobic growth on arginine: evidence for a four-gene cluster encoding the arginine deiminase pathway. J Bacteriol. 1984 December; 160(3):928-34. PMID: 6438064.
89. Walker. Severe hyperammonaemia in adults not explained by liver disease. Ann Clin Biochem. 2012 May; 49(Pt 3):214-28. Review. PMID: 22349554.
90. Winteler et al. The homologous regulators ANR of *Pseudomonas aeruginosa* and FNR of *Escherichia coli* have overlapping but distinct specificities for anaerobically inducible promoters. Microbiology. 1996 March; 142 (Pt 3):685-93. PMID: 8868444.
91. Wu et al. Direct regulation of the natural competence regulator gene tfoX by cyclic AMP (cAMP) and cAMP receptor protein in Vibrios. Sci Rep. 2015 Oct. 7; 5:14921. PMID: 26442598.
92. Zimmermann et al. Anaerobic growth and cyanide synthesis of *Pseudomonas aeruginosa* depend on anr, a regulatory gene homologous with fnr of *Escherichia coli*. Mol Microbiol. 1991 June; 5(6):1483-90. PMID: 1787798.
93. Wright O, Delmans M, Stan G B, Ellis T. GeneGuard: A modular plasmid system designed for biosafety. ACS Synth Biol. 2015 Mar. 20; 4(3):307-16. PMID: 24847673.
94. Liu Y, White R H, Whitman W B. Methanococci use the diaminopimelate aminotransferase (DapL) pathway for lysine biosynthesis. J Bacteriol. 2010 July; 192(13):3304-10. PMID: 20418392.
95. Dogovski et al. (2012) Enzymology of Bacterial Lysine Biosynthesis, Biochemistry, Prof. Deniz Ekinci (Ed.), ISBN: 978-953-51-0076-8, InTech, Available from:
96. http://www.intechopen.com/books/biochemistry/enzymology-of-bacterial-lysine-biosynthesis.
97. Feng et al. Role of phosphorylated metabolic intermediates in the regulation of glutamine synthetase synthesis in *Escherichia coli*. J Bacteriol. 1992 October; 174(19): 6061-70. PMID: 1356964.
98. Lodeiro et al. Robustness in *Escherichia coli* glutamate and glutamine synthesis studied by a kinetic model. J Biol Phys. 2008 April; 34(1-2):91-106. PMID: 19669495.
99. Reboul et al. Structural and dynamic requirements for optimal activity of the essential bacterial enzyme dihydrodipicolinate synthase. PLoS Comput Biol. 2012; 8(6): e1002537. PMID: 22685390.
100. Saint-Girons et al. Structure and autoregulation of the metJ regulatory gene in *Escherichia coli*. J Biol Chem. 1984 Nov. 25; 259(22):14282-5. PMID: 6094549.
101. Shoeman et al. Regulation of methionine synthesis in *Escherichia coli*: Effect of metJ gene product and S-adenosylmethionine on the expression of the metF gene. Proc Natl Acad Sci USA. 1985 June; 82(11):3601-5. PMID: 16593564.
102. van Heeswijk et al. Nitrogen assimilation in *Escherichia coli*: putting molecular data into a systems perspective. Microbiol Mol Biol Rev. 2013 December; 77(4): 628-95. PMID: 24296575.

EXAMPLES

The following examples provide illustrative embodiments of the disclosure. One of ordinary skill in the art will recognize the numerous modifications and variations that may be performed without altering the spirit or scope of the disclosure. Such modifications and variations are encompassed within the scope of the disclosure. The Examples do not in any way limit the disclosure.

Construction of plasmids encoding ammonia consuming circuits, including circuits comprising ΔArgR, ArgAfbr, and/or ΔThyA are inter alia described in the Examples of co-owned WO2017139697 and US20160333326, the contents of which is herein incorporated by reference in its entirety. A Functional Assay Demonstrating that the Recombinant Bacterial Cells disclosed herein consume ammonia and produce arginine is inter alia described in the Examples of U.S. Pat. Nos. 9,487,764 and 9,688,967 and International Patent Application Publication WO2017139697, the contents of which is herein incorporated by reference in its entirety. The in vitro activity of various strains (i.e., including ΔArgR and ArgA$^{fbr}$ plus or minus ΔThyA) is described in the Examples of co-owned WO2017139697 and US20160333326. In vivo activity assays which may be used to determine in vivo efficacy for any of the strains described herein, e, are described in Examples of WO2017139697 and US20160333326 the contents of which is herein incorporated by reference in its entirety. Integration of constructs into the genome, e.g., using lambda red recombination is also described in WO2017139697 and US20160333326.

Example 1. Inflammatory Exploration of TAA Model Treated with SYN-UCD305

To study the preventative effect of strain SYN-UCD305 (comprising ΔArgR, PfnrS-ArgAfbr integrated into the chromosome at malEK locus, and ΔThyA (thymidine auxotrophy)) and streptomycin resistant E. coli Nissle (E.cNStr) in inflammation and gut leakiness in the Balb/cJ TAA-inducible mouse model. FITC-Dextran analysis of serum from treated mice was used to determine the inflammatory effects of chronic dose administration in the TAA Balb/CJ model.

This study used 40 female Balb/CJ mice received from Jackson Laboratories that were fed normal chow (Picolab Diet 5083) and normal water (InnoVive). The 40 mice were separated into 4 groups of 10 mice each Animals in Groups 2, 3, & 4 were administered 100 uL of 150 mg/kg solution of Thioacetamide (TAA) injections intraperitoneally (IP) on three times weekly for 20 weeks prior to the start of the study and continued to be dosed for the duration of the study. All groups received 100 uL oral gavage (PO) dose of treatment (bacterial strains or vehicle control) twice daily (BID) for 9 days. Group 1 mice received only vehicle (15% glycerol in PBS) for treatment. Group 2 mice received vehicle and TAA injections. Group 3 mice received E.cNStr at 1e10 and TAA injections. Group 4 mice received SYN-UCD305 at 1e10 and TAA injections.

Figure 5A:
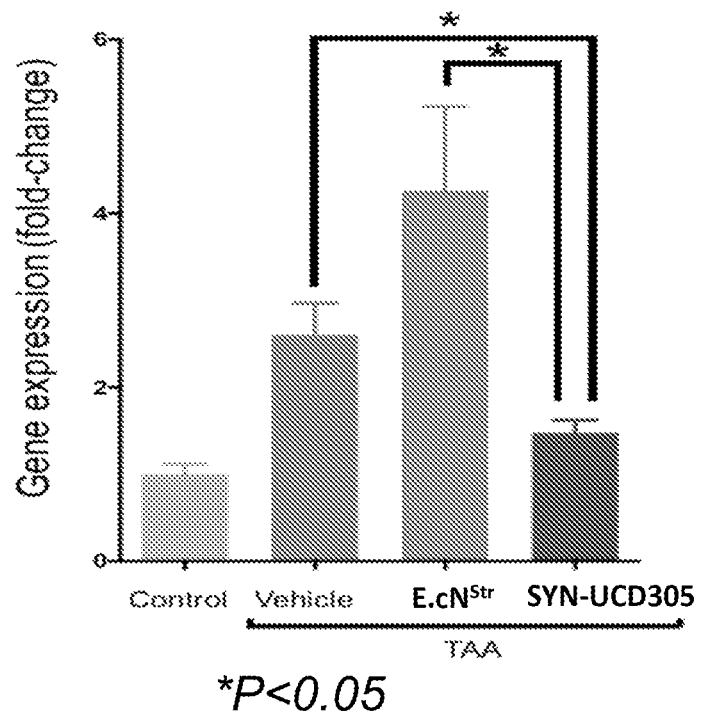
FIGS. 5A and 5B depicts graphs showing levels of IL-6 mRNA (FIG. 5A) and levels of TNF-alpha mRNA (FIG. 5B) in the colon ammonia observed in a liver fibrosis study in which the mice were treated with TAA three times weekly for 20 weeks prior to the study and throughout the 9-day study. During the study, mice (n=10) were either gavaged with vehicle control, streptomycin resistant *E. coli* Nissle (1e10 CFU) or SYN-UCD305 (1e10 CFU) twice daily (BID) for 9 days.
Figure 5B:
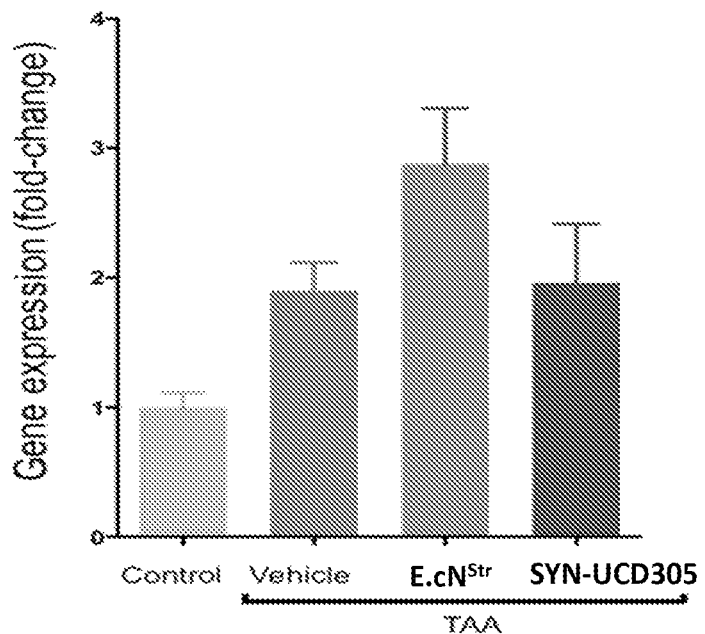

At the end of the study, serum was collected for FITC dextran and colon tissue was collected to assess levels of IL-6, and TNF-α mRNA according to standard qPCR protocols. Results are shown in FIG. 5A and FIG. 5B. mRNA levels of proinflammatory cytokine IL-6 are reduced in the SYN-UCD305 treated mice relative to vehicle controls and mice treated with E.cNStr. A trend is seen with TNF-alpha levels.

As shown in 4A, TAA-induced liver injury results in elevated expression of the pro-fibrotic markers TGF-beta and alphaSMA in the liver. Treatment with SYN094 attenuates the elevated TGF-beta mRNA expression, while SYN-UCD305 treatment further suppresses TGF-beta mRNA levels compared to SYN094 treatment. Similar trend was observed following treatment with alphaSMA.

Collection Process:

On day 9 of the study all mice were fasted after their 4:30 pm PO dose and left without food overnight. On day 10 mice were PO dosed at 6:30 am with 200 uL of 50 mg/ml FITC-Dextran. The food was returned to the mice at 10:50 am. At 7 hours post FITC-Dextran the mice were euthanized and both blood and colons were collected. An extra 10 naïve age matched Balb/CJ mice were euthanized, and blood collected for use as a standard curve.

The blood was collected by cardiac puncture using 26 g needle attached to 1 mL syringe. Blood was placed into serum tubes and allowed to clot for ~30 minutes. Once clotted, blood was spun down to serum using a centrifuge at 10000 rcf for ~7 minutes and placed into 2 mL centrifuge tubes (Fisher Scientific, 05-408-138). Serum was then stored overnight at 4 C in light protected containers. The GI tract from the cecum to the rectum was harvested from each mouse. The colon was clipped at the cecum junction and contents removed by gently squeezing the tissue with tweezers (not flushed). Mid-colon was collected by removing ~2 cm of the proximal end and ~2 cm of the distal end of the colon. Tissue was placed in 800 ul RNase later within a deep 96 well plate.

The day after euthanization/collection 50 uL of serum was plated onto a flat bottom black plate (Corning CLS3694 or CLS3650). Each well had 50 uL of 1×PBS added and mixed. This totaled 100 uL per well. The last row of the plate contained 12 wells of serum from the naïve mice. A second flat black bottom plate was created as a duplicate and 50 uL of serum/PBS mixture was removed from the original plate and added to the duplicate plate. For the standard curve a serial dilution of stock FITC-Dextran was created starting at 200 ug/mL, with a 1:2 dilution within 12 wells. In the last row the naïve mouse serum well #1 was given 50 uL of 200 ug/mL FITC-Dextran. From this well 50 uL was removed and mixed with well #2, then 50 uL from well #2 was removed and mixed with well #3. This continued until well #11, leaving well #12 with only serum and PBS, no FITC-Dextran.

Example 2. Liver Fibrosis Study in TAA Treated Mice Comparing E.cNStr and SYN-UCD305

A liver fibrosis study was conducted to determine the preventative effect of strain SYN-UCD305 and E.cN$^{Str}$ treatment on liver disease, inflammation, fibrosis/necrosis/apoptosis and signaling in Balb/cJ mice treated with short term TAA.

This study used 40 female Balb/CJ mice received from Jackson Laboratories that were fed normal chow (Picolab Diet 5083) and normal water (InnoVive). The 40 mice were separated into 4 groups of 10 mice each Animals in Groups 2, 3, & 4 were administered 100 uL of 150 mg/kg solution of Thioacetamide (TAA) injections intraperitoneally (IP) three times weekly for three weeks prior to the start of the study and continue to be dosed for the duration of the study. All groups received 100 uL oral gavage (PO) dose of treatment twice daily (BID) for 21 days. Group 1 mice received only vehicle (15% glycerol in PBS) for treatment. Group 2 mice received vehicle and TAA injections. Group 3 mice received E.cN$^{Str}$ at 1e10 and TAA injections. Group 4 mice received SYN-UCD305 at 1e10 and TAA injections. The end of study had plasma collected for NH3, ALT, & AST, brains were collected for LCMS/MS analysis, and liver tissues were collected for qPCR and pathology. Tissues were processed for pPCR analysis, and mRNA levels of IL-6, TNF-α, TGF-B1 and αSMA (smooth muscle specific actin).

As shown in 5A, TAA-induced liver injury results in elevated expression of the proinflammatory cytokines il-6 and TNF alpha in the colon. Treatment with SYN094 attenuates the elevated il-6 mRNA expression, while SYN-UCD305 treatment further suppresses il-6 mRNA levels compared to SYN094 treatment. Similar trend was observed following treatment with TNF alpha.

Collection Process

On day 21 of the study all mice were PO dosed at 11:02 am according to their treatment group. At 2:00 pm (3 hours post dose) the mice were euthanized and both blood and livers were collected. Mice were euthanized and blood collected by cardiac puncture using 26 g needle attached to 1 mL syringe and placed into lithium heparinized tubes (Microvette CB300, Sarstedt). Blood was initially tested for ammonia immediately after collection using 20 uL pipetted onto ammonia analyzer strips (Arkray, Pocketchem BA), incubated for 3 minutes before being read on the ammonia chemical analyzer (Arkray, Pocketchem BA, dist. Woodley Equipment, UK). Remaining blood was centrifuged (2000 g @4 C for 10 mins) and separated plasma was pipetted off and plated on 96-well conical bottom plates (Fisher Scientific, 12-565-438) awaiting analysis. Samples were kept on ice then stored at −80 C until thawed for sample analysis via LCMS/MS. Liver was collected and separated into two lobes. One lobe of the liver was be placed into 2 mL tube and flash frozen to be homogenized. Brains were collected and the Hippocampus removed and placed into 2 mL tubes and flash frozen to be homogenized.

| | Sequences |
|---|---|
| fbr ArgA SEQ ID NO: 1 | ATGGTAAAGGAACGTAAAACCGAGTTGGTCGAGGGATTCC GCCATTCGGTTCCCTGTATCAATACCCACCGGGGAAAAAC GTTTGTCATCATGCTCGGCGGTGAAGCCATTGAGCATGAG AATTTCTCCAGTATCGTTAATGATATCGGGTTGTTGCACA GCCTCGGCATCCGTCTGGTGGTGGTCTATGGCGCACGTCC GCAGATCGACGCAAATCTGGCTGCGCATCACCACGAACCG CTGTATCACAAGAATATACGTGTGACCGACGCCAAAACAC TGGAACTGGTGAAGCAGGCTGCGGGAACATTGCAACTGGA TATTACTGCTCGCCTGTCGATGAGTCTCAATAACACGCCG CTGCAGGGCGCGCATATCAACGTCGTCAGTGGCAATTTTA TTATTGCCCAGCCGCTGGGCGTCGATGACGGCGTGGATTA CTGCCATAGCGGGCGTATCCGGCGGATTGATGAAGACGCG ATCCATCGTCAACTGGACAGCGGTGCAATAGTGCTAATGG GGCCGGTCGCTGTTTCAGTCACTGGCGAGAGCTTTAACCT GACCTCGGAAGAGATTGCCACTCAACTGGCCATCAAACTG AAAGCTGAAAAGATGATTGGTTTTTGCTCTTCCCAGGGCG TCACTAATGACGACGGTGATATTGTCTCCGAACTTTTCCC TAACGAAGCGCAAGCGCGGGTAGAAGCCCAGGAAGAGAAA GGCGATTACAACTCCGGTACGGTGCGCTTTTTGCGTGGCG CAGTGAAAGCCTGCCGCAGCGGCGTGCGTCGCTGTCATTT AATCAGTTATCAGGAAGATGGCGCGCTGTTGCAAGAGTTG TTCTCACGCGACGGTATCGGTACGCAGATTGTGATGGAAA GCGCCGAGCAGATTCGTCGCGCAACAATCAACGATATTGG CGGTATTCTGGAGTTGATTCGCCCACTGGAGCAGCAAGGT ATTCTGGTACGCCGTTCTCGCGAGCAGCTGGAGATGGAAA TCGACAAATTCACCATTATTCAGCGCGATAACACGACTAT TGCCTGCGCCGCGCTCTATCCGTTCCCGGAAGAGAAGATT GGGGAAATGGCCTGTGTGGCAGTTCACCCGGATTACCGCA GTTCATCAAGGGGTGAAGTTCTGCTGGAACGCATTGCCGC TCAGGCTAAGCAGAGCGGCTTAAGCAAATTGTTTGTGCTG ACCACGCGCAGTATTCACTGGTTCCAGGAACGTGGATTTA CCCCAGTGGATATTGATTTACTGCCCGAGAGCAAAAAGCA GTTGTACAACTACCAGCGTAAATCCAAAGTGTTGATGGCG GATTTAGGGTAA |
| fbr ArgA SEQ ID NO: 2 | MVKERKTELVEGFRHSVPCINTHRGKTFVIMLGGEAIEHE NFSSIVNDIGLLHSLGIRLVVVYGARPQIDANLAAHHHEP LYHKNIRVTDAKTLELVKQAAGTLQLDITARLSMSLNNTP LQGAHINVVSGNFIIAQPLGVDDGVDYCHSGRIRRIDEDA IHRQLDSGAIVLMGPVAVSVTGESFNLTSEEIATQLAIKL KAEKMIGFCSSQGVTNDDGDIVSELFPNEAQARVEAQEEK GDYNSGTVRFLRGAVKACRSGVRRCHLISYQEDGALLQEL FSRDGIGTQIVMESAEQIRRATINDIGGILELIRPLEQQG ILVRRSREQLEMEIDKFTIIQRDNTTIACAALYPFPEEKI GEMACVAVHPDYRSSSRGEVLLERIAAQAKQSGLSKLFVL TTRSIHWFQERGFTPVDIDLLPESKKQLYNYQRKSKVLMA DLG* |

What is claimed is:

1. A method for treating a subject having liver disease, the method comprising:

administering an engineered bacterium, or a pharmaceutical composition comprising the engineered bacterium, to the subject, and measuring gene expression in the colon and/or liver before the administering, and/or measuring gene expression in the colon and/or liver after administering, wherein the administering:

i) reduces IL-6 gene expression in the liver by at least 10% as compared to IL-6 gene expression in the liver before the administering;

ii) reduces TNFα gene expression in the liver by at least 10% as compared to TNFα gene expression in the liver before the administering;

iii) reduces TGFβ gene expression in the liver by at least 10% as compared to TGFβ gene expression in the liver before the administering;

iv) reduces αSMA gene expression in the liver by at least 10% as compared to αSMA gene expression in the liver before the administering;
v) reduces IL-6 gene expression in the colon by at least 10% as compared to IL-6 gene expression in the colon before the administering; and/or
vi) wherein blood ammonia levels are decreased by at least 5% after administering as compared to blood ammonia levels before the administering.

2. The method of claim 1, wherein the administering reduces IL-6 gene expression in the liver by at least 15%, 20%, 25%, 30%, 35%, 40%, 45%, or 50% as compared to IL-6 gene expression in the liver before the administering.

3. The method of claim 1, wherein administering reduces TGFβ gene expression in the liver by at least 15% or 20% as compared to TGFβ gene expression in the liver before the administering.

4. The method of claim 1, wherein administering reduces αSMA gene expression in the liver by at least 15%, 20%, 25%, 30%, 35%, 40%, 45%, or 50% as compared to αSMA gene expression in the liver before the administering.

5. The method of claim 2, wherein administering reduces IL-6 gene expression in the colon by at least 15% or 20% as compared to IL-6 gene expression in the colon before the administering.

6. The method of claim 1, wherein blood ammonia levels are decreased by at least 10%, 15%, 20%, 25%, 30%, 35%, 40%, 45%, or 50% as compared to blood ammonia levels before the administering.

7. The method of claim 1, further comprising measuring blood ammonia levels before the administering and/or further comprising measuring blood ammonia levels after the administering.

8. The method of claim 1, wherein the engineered bacterium reduces inflammation in the colon of the subject.

9. The method of claim 1, wherein the engineered bacterium reduces inflammation in the liver of the subject.

10. The method of claim 1, wherein the bacterium comprises one or more gene sequences encoding an ammonia consumption circuit.

11. The method of claim 1, wherein the bacterium comprises one or more gene sequences encoding an arginine production circuit.

12. The method of claim 1, wherein the bacterium comprises a gene encoding an arginine feedback resistant N-acetylglutamate synthetase (ArgAfbr), wherein the ArgAfbr has reduced arginine feedback inhibition as compared to a wild-type N-acetylglutamate synthetase from the same bacterial subtype under the same conditions and wherein expression of the gene encoding ArgAfbr is controlled by a promoter that is induced by low-oxygen or anaerobic conditions; and wherein the bacterium has been genetically engineered to lack a functional ArgR.

13. The method of claim 1, wherein each copy of a functional argR gene normally present in a corresponding wild-type bacterium has been deleted.

14. The method of claim 1, wherein under low-oxygen or anaerobic conditions, the transcription of each gene in the engineered bacterium that is present in an operon comprising a functional ARG box and which encodes an arginine biosynthesis enzyme is increased as compared to a corresponding gene in a wild-type bacterium under the same conditions.

15. The method of claim 1, wherein the bacterium comprises a gene sequence encoding a biosynthetic pathway for producing butyrate.

16. The method of claim 12, wherein the promoter that is induced under low-oxygen or anaerobic conditions is an FNR promoter.

17. The method of claim 1, wherein the bacterium is a non-pathogenic bacterium and/or a probiotic bacterium.

18. The method of claim 1, wherein the bacterium is selected from the group consisting of *Bacteroides, Bifidobacterium, Clostridium, Escherichia, Lactobacillus*, and *Lactococcus*.

19. The method of claim 18, wherein the bacterium is *Escherichia coli* strain Nissle.

20. The method of claim 1, wherein the bacterium is a thyA or dapB auxotroph.

21. The method of claim 1, wherein the liver disease is selected from NASH, NAFLD, and hepatic encephalopathy.

22. The method of claim 1, wherein administering reduces TGFα gene expression in the liver by at least 15% or 20% as compared to TGFα gene expression in the liver before the administering.

* * * * *